US006787542B2

(12) United States Patent
Wang et al.

(10) Patent No.: US 6,787,542 B2
(45) Date of Patent: Sep. 7, 2004

(54) ARYL PHENYLHETEROCYCLYL SULFIDE DERIVATIVES AND THEIR USE AS CELL ADHESION-INHIBITING ANTI-INFLAMMATORY AND IMMUNE-SUPPRESSIVE AGENTS

(75) Inventors: Gary T. Wang, Niles, IL (US); Sheldon Wang, Carmel, IN (US); Robert Gentles, Libertyville, IL (US)

(73) Assignee: ICOS Corporation, Bothell, WA (US)

(*) Notice: Subject to any disclaimer, the term of this patent is extended or adjusted under 35 U.S.C. 154(b) by 0 days.

(21) Appl. No.: 09/888,840

(22) Filed: Jun. 25, 2001

(65) Prior Publication Data

US 2002/0132807 A1 Sep. 19, 2002

Related U.S. Application Data

(60) Provisional application No. 60/214,983, filed on Jun. 29, 2000.

(51) Int. Cl.[7] .................... C07D 401/14; C07D 401/04; C07D 403/04; A61K 31/506
(52) U.S. Cl. .................... 514/235.8; 544/296; 544/327; 544/122; 544/331; 544/332; 514/256; 514/275
(58) Field of Search ............... 544/296, 327, 544/122, 331, 332; 514/256, 235.8, 275

(56) References Cited

U.S. PATENT DOCUMENTS

| | | | |
|---|---|---|---|
| 4,973,599 A | 11/1990 | Gilman et al. | |
| 5,028,629 A | 7/1991 | Hite et al. | |
| 5,776,951 A | 7/1998 | Arrowsmith et al. | |
| 5,883,106 A | 3/1999 | Stevens et al. | |
| 5,883,133 A | 3/1999 | Schwark et al. | |
| 5,912,266 A | 6/1999 | Perez | |
| 6,110,922 A | 8/2000 | Link et al. | |
| 6,110,992 A | 8/2000 | Wada et al. | |
| 6,211,215 B1 | 4/2001 | Momose et al. ............ 514/374 |

FOREIGN PATENT DOCUMENTS

| | | |
|---|---|---|
| AT | 392788 | 11/1990 |
| DE | 2123383 | 12/1971 |
| EP | 0219756 | 10/1986 |
| EP | 0262845 | 6/1988 |
| EP | 0455356 | 11/1991 |
| EP | 0710654 | 5/1996 |
| EP | 1052238 | 11/2000 |
| GB | 2 117 760 A | 10/1993 |
| JP | 12072766 | 3/2000 |
| WO | 9626921 | 9/1996 |
| WO | WO98/13347 | 4/1998 |
| WO | WO98/39303 | 9/1998 |
| WO | WO99/11258 | 3/1999 |
| WO | WO99/20617 | 4/1999 |
| WO | WO99/20618 | 4/1999 |
| WO | WO99/49856 | 10/1999 |
| WO | WO00/15604 | 3/2000 |
| WO | WO00/15645 | 3/2000 |
| WO | WO00/21920 | 4/2000 |
| WO | WO01/27102 | 4/2000 |
| WO | WO39081 | 7/2000 |
| WO | WO00/48989 | 8/2000 |
| WO | WO00/59878 | 10/2000 |
| WO | WO59880 | 10/2000 |
| WO | WO00/60355 | 10/2000 |
| WO | WO01/06984 | 2/2001 |
| WO | WO01/07052 | 2/2001 |

OTHER PUBLICATIONS

Springer, T.A., 1994, *Traffic Signals for Lymphocyte Recirculation and Leykocyte Emigration: The Multistep Paradigm*, Cell, 76:301–314.

Lawrence, MB. et al., 1991, *Leukocytes Roll on a Selectin at Physiologic Flow Rates: Distinction from and Prerequisite for Adhesion Through Integrins*, Cell, 65:859–873.

von Adrian, et al., 1991, *Two–Step Model of Leukocyte–Endothelial Cell Interaction in Inflammation: Distinct roles for LECAM–1 and the leukocyte $\beta_2$ integrins in vivo*, Proc. Nat'l Acad. Sci. USA, 88:7538–7542.

Prescott, Ed., *Methods in Cell Biology*, Vol. XIV, Academic Press, New York, NY (1976), p. 33 et seq.

Ley, K. et al., 1991, *Lectin–Like Cell Adhesion Molecule 1 Mediates Rolling in Mesenteric Venues in vivo*, Blood, 77:2553–2555.

Berge, S.M. et al., Pharmaceutical Sciences, *Pharmaceutical Salts*, 1977, 66: 1 et seq..

Kakimoto, et al., Cell Immunol., *The Effect of Anti–Adhesion Molecule Antibody on the Development of Collagen–Induced Arthritis*, 142:326–337, 1992.

Knoerzer, et al., Toxicol Pathol., *Clinical and Histological Assessment of Collagen–Induced Arthritis Progression in the Diabetes–Resistant BB/Wor Rat*, 25:13–19, 1997.

Halloran, et al., *Cellular Adhesion Molecules in Rat Adjuvant Arthritis*, Arthritis Rheum 39:810–819, 1996.

Schimmer, et al., J. Immunol, *Streptococcal Cell Well–Induced Arthritis: Requirements for IL–4, IL–10, IFN–$_\gamma$, and Monocyte Chemoattractant Protein–1*, 160:1466–1477, 1998.

Oppenheimer–Marks et al., *Interleukin 15 Is Produced by Endothelial Cells and Increases the Transendothelial Migration of T Cells In Vitro and in the SCID Mouse–Human Rheumatoid Arthritis Model In Vivo*, J. Clin Invest 101:1261–1272, 1998.

(List continued on next page.)

Primary Examiner—Mukund J. Shah
Assistant Examiner—Kahsay Habte
(74) Attorney, Agent, or Firm—Finnegan, Henderson, Farabow, Garrett & Dunner

(57) ABSTRACT

The present invention relates to novel heterocyclyl-containing diaryl sulfide compounds that are useful for treating inflammatory and immune diseases, to pharmaceutical compositions comprising these compounds, and to methods of inhibiting inflammation or suppressing immune response in a mammal.

27 Claims, No Drawings

OTHER PUBLICATIONS

Gross et al., *Identification of LFA–1 as a Candidate Autoantigen in Treatment–Resistant Lyme Arthritis*, Science 281, 703–706, 1998.

Wegner et al., *Intercellular Adhesion Molecule–1 (ICAM–1) in the Pathogenesis of Asthma*, Science 247;456–459, 1990.

Bloemen et al., *LFA–1, and not Mac–1, is Crucial for the Development of Hyperreactivity in a Murine Model of Nonallergic Asthma*, Am. J. Respir. Crit Care Med 153:521–529, 1996.

Mulligan et al., J. Immunol, *Compartmentalized Roles for Leukocyctic Adhesion Molecules in Lung Inflammatory Injury*, 154:1350–1363, 1995.

Nagase, et al., Am. J. Respir Crit Care Med, *Intercellular Adhesion Molecule–1 Mediates Acid Aspiration–induced Lung Injury*, 154:504–510, 1996.

Bennet et al., *An ICAM–1 Antisense Oligonucleotide Prevents and Reverses Dextran Sulfate Sodium–Induced Colitis in Mica*, J. Pharmacol Exp. Ther 280:988–1000, 1997.

Hasagawa et al., *Prevention of autoimmune insulin–dependent diabetes in non–obese diabetic mice by anti–LFA–1 and anti–ICAM–1 mAb*, Int. Immunol 6:831–838, 1994.

Herrold et al., *Prevention of Autoimmune Diabetes by Treatment with Anti–LFA–1 and anti–ICAM–1 Monoclonal Antibodies*, Cell Immunol 157:489–500, 1994.

Tanaka et al., J. Immunol, *Inhibition of Inflammatory Liver Injury by a Monoclonal Antibody against Lymphocyte Function–Associated Antigen–1*, 151:5088–5095, 1993.

Kawasaki, et al., *Antibodies against Intercellular Adhesion Molecule–1 and Lymphocyte Function–Associated Antigen–1 Prevent Glomerular Injury In Rat Experimental Crescentic Glomerulonephritis*, J. Immunol. 150:1074–1083, 1993.

Panes et al., Gastroenterology, *Role of Leukocyte–Endothelial Cell Adhesion in Radiation–Induced Microvascular Dysfunction in Rats*, 108:1761–1769, 1995.

Hallahan et al., *Intercellular adhesion molecule 1 knockout abrogates radiation induced pulmonary inflammation*, Proc. Natl Acad Sci USA 94:6432–6437, 1997.

Tamiya et al., Immunopharmacology, *Protective effect of monoclonal antibodies against LFA–1 and ICAM–1 on myocardial reperfusion injury following global ischemia in rat hearts*, 29(1): 53–63, 1995.

Hartman et al., *Protection of ischmemic/reperfused canine myocardium by CL18/6, a monoclonal antibody to adhesion molecule ICAM–1*, Cardiovasc. Res. 30(1):47–54, 1995.

DeMeester et al., *Attenuation of Rat Lung Isograft Reperfusion Injury with a Combination of Anti–ICAM–1 and Anti–β$_2$ Integrin Monoclonal Antibodies*, Transplantation 62(10):1477–1485, 1996.

Horgan et al., *Role of ICAM–1 in Neutrophil–Mediated Lung Vascular injury after occlusion and Reperfusion*, Am. J. Physio. 261(5):H1578–H1584, 1991.

Bowes et al., *Monoclonal Antibody to the ICAM–1 Adhesion Site Reduces Neurological Damage in a Rabbit Cerebral Embolism Stroke Model*, Exp. Neurol 119(2): 215–219, 1993.

Chopp et al., *Postischemic Administration of an Anti–Mac–1 Antibody Reduces Ischemic Cell Damage After Transient Middle Cerebral Artery Occlusion in Rats*, Stroke 25(4): 869–875, 1994.

Clark et al., *Reduction of central nervous system ischemic injury by monoclonal antibody to intercellular adhesion molecule*, Neurosurg 75(4): 623–627, 1991.

Gute et al., *Inflammatory responses to ischemic and reperfusion in skeletal muscle*, Mol. Cell Biochem 179:169–187, 1998.

Isobe et al., *Specific Acceptance of Cardiac Allograft After Treatment with Antibodies to ICAM–1 and LFA–1*, Science 255:1125–1127, 1992.

Talento et al., *A Single Administration of LFA–1 Antibody Confers Prolonged Allograft Survival*, Transplantation 55:418–422, 1993.

Cosimi et al., In Vivo *Effects of Monoclonal Antibody to ICAM–1 (CD54) In Nonhuman Primates with Renal Allografts*, J. Immunol 144:4604–4612, 1990.

Nakao et al., *Monoclonal Antibodies Against ICAM–1 and LFA–1 Prolong Nerve Allograft Survival*, Muscle Nerve 18:93–102, 1995.

Gorezynski et al., *A Role for Nonspecific (Cyclosporin A) or Specific (Monoclonal Antibodies to ICAM–1, LFA–1, and IL–10) Immunomodulation in the Prolongation of Skin Allografts after Antigen–Specific Pretransplant Immunization or Transfusion*, J. Immunol 152:2011–2019, 1994.

He et al., *Effect of LFA–1 and ICAM–1 Antibody Treatment on Murine Corneal Allograft Survival*, Opthalmol Vis. Sci 35:3218–3225, 1994.

Zeng et al., *Inhibition of Transplant Rejection by Pretreatment of Xenogeneic Pancreative Islet Cells with Anti–ICAM–1 Antibodies*, Transplantation, 58:681–689, 1994.

Harning et al., *Reduction In the Severity of Graft–Versus–Host Disease and Increased Survival in Allogeneic Mice By Treatment With Monoclonal Antibodies to Cell Adhesion Antigens LFA–1α and MALA–2*, Transplantation, 52:842–845, 1991.

Higuchi et al., *Prodrugs as Novel Delivery Systems*, vol. 14 of the A.C.S. Symposium Series.

Roche, Edward, *Bioreversible Carriers in Drug Design*, American Pharmaceutical Association and Pergamon Press, 1987.

Aoudjit et al., *Protection from Lymphoma Cell Metastasis in ICAM–1 Mutant Mice: A Posthoming Event*, J. Immunol. 161:2333–2338, 1998.

Wegner et al., *Intercellular Adhesion Molecule–1 Contributes to Pulmonary Oxygen Toxicity in Mice: Role of Leukocytes Revised*, J. Immunol 154:1350–1363.

U.S. patent application Ser. No. 09/285,477.

U.S. patent application Ser. No. 09/285,325.

Ali, H. et al., *Mechanisms of Inflammation and Leukocyte Activation*, Med. Clin. North America (1997) 81:1–28.

Bella, J., et al. *The Structure of the Two Amino–terminal Domains of Human ICAM–1 Suggests How it Functions as a Rhinovirus Receptor and As An LFA–1 Integrin Ligand.* (1998) Proc. Natl. Acad. Sci. USA 95:4140–4145.

Binnerts, M.E., et al. *How LFA–1 Binds to Different Ligands.* (1999) Immunol Today 20:240–245.

Boschelli, D.H., et al. *Inhibition of E–Selectin–, ICAM–1–, and VCAM–1–Mediated Cell Adhesion by Benzo[b]thiophene–, Benzofuran–, Indole–, and Naphthalene–2–Carboxamides: Identification of PD 144795 as an Antiinflammatory Agent.* ((1995) J. Med. Chem. 38:4597–4614.

Carlos, T.M., *Leukocyte–Endothelial Adhesion Molecules.* Blood (1994) 84:2068–2101.

Edwards, C.P. et al., *Mapping the Intercellular Adhesion Molecule–1 and –2 Binding Site on the Inserted Domain of Leukocyte Function–associated Antigen–1.* (1998) J. Biol. Chem. 273:28937–28944.

Fisher, K.L., et al., *Identification of the Binding Site in Intercellular Adhesion Molecule 1 for its Receptor, Leukocyte Function–associated Antigen 1*. (1997) Mol. Biol. Cell 8:501–515.

Gadek, T.R., et al., *Identification and Characterization of Antagonists of the LFA–1/ICAM–1 Protein–Protein Interaction as Novel Immunomodulatory Agents*. 220th ACS National Meeting, Washington, D.C., USA (2000) MEDI 177.

Gahmberg, C.G., *Leukocyte Adhesion: CD11/CD18 Integrins and Intercullular Adhesion Molecules*, Curr. Opin. Cell Biol. (1997) 9:643–650.

Gahmberg, C.G., *Leukocyte Adhesion: Structure and Function of Human Leukocyte $\beta_2$–integrins and Their Cellular Ligands*. (1997) Eur. J. Biochem. 245:215–232.

Green, J.M., *T Cell Receptor Stimulation, But Not CD28 Costimulation, Is Dependent on LFA–1–Mediated Events*, Eur.. J. Immunology (1994) 24:265–272.

Hamilton, G.S., et al., *Fluorenylalkanoic and Benzoic Acids as Novel Inhibitors of Cell Adhesion Processes in Leukocytes*. (1995) 38:1650–1656.

Henricks, P.A., *Pharmacological modulation of cell adhesion molecules*, Eur. J. Pharmacol. (1998) 344:1–13.

Huang, C., *A Binding Interface on the I Domain of Lymphocyte Function–associated Antigen–1 (LFA–1) Required for Specific Interaction with Intercellular Adhesion Molecule 1 (ICAM–1)*, (1995) 270:19008–19016.

Huth, J.R., *NMR and Mutagenesis Evidence for an I Domain Allosteric Site That Regulates Lymphocyte Function–associated Antigen 1 Ligand Binding*. Proc. Natl. Acad. Sci, USA (2000) 97:5231–5236.

Kallen, J., et al., *Structural Basis for LFA–1 Inhibition upon Lovastatin Binding to the CD11a I–Domain*, J. Mol. Biol. (1999) 292–1–9.

Kelly, T.A., *Cutting Edge: A Small Molecule Antagonist of LFA–1–Mediated Cell Adhesion*, J. Immunol. (1999) 163:5173–5177.

Kishimoto, T.K., *Integrins, ICAMs and Selectins: Role and Regulation of Adhesion Molecules in Neutrophil Recruitment to Inflammatory Sites*, Adv. Pharmacol. (1994) 25:117–169.

Landis, R.C. *Involvement of The "I" domain of LFA–1 in Selective Binding to Ligands ICAM–1 and ICAM–3*, J. Cell Biol. (1994) 126:529–537.

Link, J.T., et al., *Discovery and SAR of Diarylsulfide Cyclopropylamide LFA–1/ICAM–1 Interaction Antagonists*. Bioorg. Med. Cehm Lett. (2001) 11:973–976.

Liu, G., *Small Molecule Antagonists of the LFA–1/ICAM–1 Interactions as Potential Therapeutic Agents*, Expert Opin. Ther.Patents (2001) 11(9) 1383–1393.

Liu, G., et al., *Discovery of Novel P–arylthio Cinnamides as Antogonists of Leukocyte Function–associated Antigen–1/intracellular Adhesion Molecule–1 Interaction, 1. Identification of an Additional Binding Pocket Based on an Anilino Diaryl Sulfide Lead*. J. Med. Chem. (2000) 43:4025–4040.

Liu, G., et al., *Novel P–arylthio Cinnamides as Antagonists of Leukocyte Function–associated Antigen–1/intracellular Adhesion Molecule–1 Interaction. 2. Mechanism of Inhibition and Structure–based Improvement of Pharmaceutical Properties*. (2001) J. Med. Chem. 44:1202–1210.

Lu, C., et al., *An Isolated, Surface–expressed I Domain of the Integrin Al$\beta$2 Is Sufficient for Strong Adhesive Function When Locked in the Open Conformation with a Disulfide Bond*. Proc. Natl. Acad. Sci. USA (2001) 98–2387–2392.

Nakano, T., et al., *Adxanthromyclns A and B, New Inhibitors of ICAM–1/ILFA–1 Mediated Cell Adhesion Molecule from Streptomyces sp NA–148*, J. Antibos. (Tokyo) (2000) 53:12–18.

Pei, Z., et al., *Discovery of Potent Antagonists of Leukocyte Function–associated Antigen–1/intercellular Adhesion Molecule–1 Interaction. 3. Amide (C–ring) Structure–activity Relationship and Improvement of Overall Properties of Arylthio Cinnamides*. J. Med. Chem. (2001) In press.

Qu, A., et al., *The Role of the Divalent Cation in the Structure of the I Domain from the CD11a/CD18 Integrin*. (1996) Structure 4:931–942.

Sanfilippo, P.J. *Novel Thiazole Based Heterocycles as Inhibitors of LFA–1/ICAM–1 Mediated Cell Adhesion*, J. Med. Chem. (1995) 38:1057–1059.

Springer, T.A., *Adhesion Receptors of the Immune System*, Nature (1990) 346:425–434.

Stanley, P., et al., *The I Domain of Integrin LFA–1 interacts with ICAM–1 Domain 1 at Residue Glu–34 But Not Gln–73*, (1998) J. Biol. Chem. 273:3358–3362.

ARYL PHENYLHETEROCYCLYL SULFIDE DERIVATIVES AND THEIR USE AS CELL ADHESION-INHIBITING ANTI-INFLAMMATORY AND IMMUNE-SUPPRESSIVE AGENTS

CROSS REFERENCE TO RELATED APPLICATION

This application claims the benefit of provisional U.S. patent application Serial No. 60/214,983 filed Jun. 29, 2000.

TECHNICAL FIELD

The present invention relates to compounds that are useful for treating inflammatory and immune diseases, to pharmaceutical compositions comprising these compounds, and to methods of inhibiting inflammation or suppressing immune response in a mammal.

BACKGROUND OF THE INVENTION

Inflammation results from a cascade of events that includes vasodilation accompanied by increased vascular permeability and exudation of fluid and plasma proteins. This disruption of vascular integrity precedes or coincides with an infiltration of inflammatory cells. Inflammatory mediators generated at the site of the initial lesion serve to recruit inflammatory cells to the site of injury. These mediators (chemokines such as IL-8, MCP-1, MIP-1, and RANTES, complement fragments and lipid mediators) have chemotactic activity for leukocytes and attract the inflammatory cells to the inflamed lesion. These chemotactic mediators which cause circulating leukocytes to localize at the site of inflammation require the cells to cross the vascular endothelium at a precise location. This leukocyte recruitment is accomplished by a process called cell adhesion.

Cell adhesion occurs through a coordinately regulated series of steps that allow the leukocytes to first adhere to a specific region of the vascular endothelium and then cross the endothelial barrier to migrate to the inflamed tissue (Springer, T. A., 1994, "Traffic Signals for Lymphocyte Recirculation and Leukocyte Emigration: The Multistep Paradigm", *Cell,* 76: 301–314; Lawrence, M. B., and Springer, T. A., 1991, "Leukocytes' Roll on a Selectin at Physiologic Flow Rates: Distinction from and Prerequisite for Adhesion Through Integrins", *Cell,* 65: 859–873; von Adrian, U., Chambers, J. D., McEnvoy, L. M., Bargatze, R. F., Arfos, K. E, and Butcher, E. C., 1991, "Two-Step Model of Leukocyte-Endothelial Cell Interactions in Inflammation", *Proc. Nat'l. Acad. Sci. USA,* 88: 7538–7542; and Ley, K., Gaehtgens, P., Fennie, C., Singer, M. S., Lasky, L. H. and Rosen, S. D.,1991, "Lectin-Like Cell Adhesion Molecule 1 Mediates Rolling in Mesenteric Venules in vivo", *Blood* 77: 2553–2555). These steps are mediated by families of adhesion molecules such as integrins, Ig supergene family members, and selectins which are expressed on the surface of the circulating leukocytes and on the vascular endothelial cells. The first step consists of leukocytes rolling along the vascular endothelial cell lining in the region of inflammation. The rolling step is mediated by an interaction between a leukocyte surface oligosaccharide, such as Sialylated Lewis-X antigen (SLe$^x$), and a selectin molecule expressed on the surface of the endothelial cell in the region of inflammation. The selectin molecule is not normally expressed on the surface of endothelial cells but rather is induced by the action of inflammatory mediators such as TNF-α and interleukin-1. Rolling decreases the velocity of the circulating leukocyte in the region of inflammation and allows the cells to more firmly adhere to the endothelial cell. The firm adhesion is accomplished by the interaction of integrin molecules that are present on the surface of the rolling leukocytes and their counter-receptors (the Ig superfamily molecules) on the surface of the endothelial cell. The Ig superfamily molecules or CAMs (Cell Adhesion Molecules) are either not expressed or are expressed at low levels on normal vascular endothelial cells. The CAM's, like the selecting, are induced by the action of inflammatory mediators like TNF-alpha and IL-1. The final event in the adhesion process is the extravasation of leukocytes through the endothelial cell barrier and their migration along a chemotactic gradient to the site of inflammation. This transmigration is mediated by the conversion of the leukocyte integrin from a low avidity state to a high avidity state. The adhesion process relies on the induced expression of selectins and CAM's on the surface of vascular endothelial cells to mediate the rolling and firm adhesion of leukocytes to the vascular endothelium.

The interaction of the intercellular adhesion molecule ICAM-1 (cd54) on endothelial cells with the integrin LFA-1 on leukocytes plays an important role in endothelial-leukocyte contact. Leukocytes bearing high-affinity LFA-1 adhere to endothelial cells through interaction with ICAM-1, initiating the process of extravasation from the vasculature into the surrounding tissues. Thus, an agent which blocks the ICAM-1/LFA-1 interaction suppresses these early steps in the inflammatory response. Consistent with this background, ICAM-1 knockout mice have numerous abnormalities in their inflammatory responses.

The present invention discloses compounds which bind to the interaction-domain (I-domain) of LFA-1, thus interrupting endothelial cell-leukocyte adhesion by blocking the interaction of LFA-1 with ICAM-1, ICAM-3, and other adhesion molecules. These compounds are useful for the treatment or prophylaxis of diseases in which leukocyte trafficking plays a role, notably acute and chronic inflammatory diseases, autoimmune diseases, tumor metastasis, allograft rejection, and reperfusion injury.

SUMMARY OF THE INVENTION

The present invention is directed to compounds of Formula I

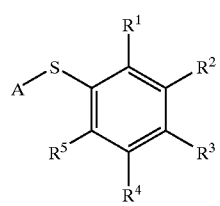

Formula I or pharmaceutically acceptable salts, optical isomers, or prodrugs thereof, wherein $R^1$, $R^2$, $R^3$, $R^4$ and $R^5$ are each independently selected from the group consisting of hydrogen, halogen, alkyl, haloalkyl, alkoxy, cyano, nitro, cycloalkyl and carboxaldehyde, or a group of Formula II defined as

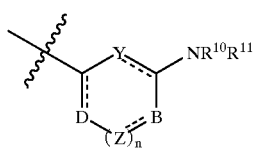

Formula II subject to the proviso that one or more than one of $R^1$ or $R^3$ is a group of Formula II as defined above;

wherein D, B, Y and Z at each occurrence are independently selected from the group consisting of —$CR^6$=, —$CR^7R^8$—, C(O)—, —O—, —$SO_2$—, —S—, —N=, and —$NR^9$—;

n is an integer of zero to three;

$R^6$, $R^7$, $R^8$, and $R^9$, at each occurrences are each independently selected from the group consisting of hydrogen, alkyl, carboxy, hydroxyalkyl, alkylaminocarbonylalkyl dialkylaminocarbonylalkyl and carboxyalkyl; and $R^{10}$ and $R^{11}$ are each independently selected from the group consisting of hydrogen, alkyl, cycloalkyl, alkoxyalkyl, alkoxycarbonylalkyl, carboxyalkyl, hydroxyalkyl, heterocyclyl, heterocyclylalkyl and heterocyclylamino; or $R^{10}$ and $R^{11}$ are taken together with N to form a three to seven membered unsubstituted heterocyclyl ring, or a three to seven membered substituted heterocyclyl ring substituted with one or more than one substituent $R^{13}$, wherein $R^{13}$, at each occurrence is independently selected from the group consisting of alkyl, alkylene, alkoxy, alkoxyalkyl, cycloalkyl, aryl, heterocyclyl, heterocyclylalkyl, heterocyclylcarbonyl, heterocyclylalkylaminocarbonyl, hydroxy, hydroxyalkyl, hydroxyalkoxyalkyl, carboxy, carboxyalkyl, carboxycarbonyl, carboxaldehyde, alkoxycarbonyl, arylalkoxycarbonyl, aminoalkyl, aminoalkanoyl, aminocarbonyl, carboxamido, alkoxycarbonylalkyl, carboxamidoalkyl, cyano tetrazolyl, alkanoyl, hydroxyalkanoyl, alkanoyloxy, alkanoylamino, alkanoyloxyalkyl, alkanoylaminoalkyl, sulfonate, alkylsulfonyl, alkylsulfonylaminocarbonyl, arylsulfonylaminocarbonyl and hererocyclylsulfonylaminocarbonyl;

wherein A is an unsubstituted aryl group, an unsubstituted heterocyclyl group, a substituted aryl group, or a substituted heterocyclyl group, substituted with one or more than one substituent $R^{12}$, wherein $R^{12}$, at each occurrence, is independently selected from the group consisting of halogen, alkyl, aryl, haloalkyl, hydroxy, alkoxy, alkoxyalkyl, alkoxycarbonyl, alkoxyalkoxy, hydroxyalkyl, aminoalkyl, aminocarbonyl, alkyl (alkoxycarbonylalkyl) aminoalkyl, heterocyclyl, heterocyclylalkyl, carboxaldehyde, carboxaldehyde hydrazone, carboxamide, alkoxycarbonylalkyl, carboxy, carboxyalkyl, carboxyalkoxy, carboxythioalkoxy, carboxycycloalkoxy, thioalkoxy, carboxyalkylamino, trans-cinnamyl, hydroxyalkylaminocarbonyl, cyano, heterocyclylalkylamino, and heterocyclylalkylaminocarbonyl; and wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are unsubstituted or substituted with at least one electron donating or electron withdrawing group.

Presently preferred compounds of Formula I have $R^3$ as Formula II (shown above), with substituents defined as above, $R^1$ and $R^2$ each independently as hydrogen, halogen, haloalkyl or nitro; and $R^4$ and $R^5$ each independently as hydrogen or alkyl.

The present invention is also directed to compounds of Formula III

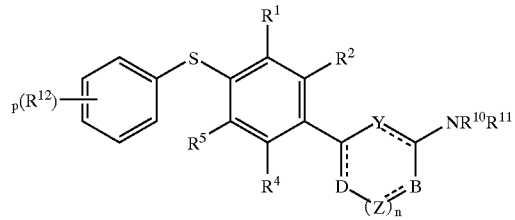

Formula III wherein $R^1$, $R^2$, $R^3$, $R^4$ and $R^5$ are each independently selected from the group consisting of hydrogen, halogen, alkyl, haloalkyl, alkoxy, cyano, nitro, cycloalkyl and carboxaldehyde;

D, B, Y and Z are as defined above for Formula I;

$R^{12}$, at each occurrence, is independently selected from die group consisting of halogen, alkyl, haloalkyl, alkoxy, carboxyalkoxy, carboxyalkyl and heterocyclyl;

p is an integer of zero to five; and wherein $R^1$, $R^2$, $R^4$, $R^5$, $R^{10}$, $R^{11}$ and $R^{12}$ are unsubstituted or substituted with at least one electron donating group or electron withdrawing group.

Presently most preferred, but not required, compounds of Formula III have p as one; $R^4$ and $R^5$ as hydrogen; $R^{12}$ as halogen, alkyl, carboxyalkoxy, carboxyalkyl or heterocyclyl; and $R^{10}$ and $R^{11}$ are taken together with N to form a three to seven membered unsubstituted heterocyclyl ring, or a three to seven membered substituted heterocyclyl ring; said ring being piperidine, piperazine, morpholine, pyrrolidine or azetidine.

Presently most preferred, but not required, compounds are of Formula IV

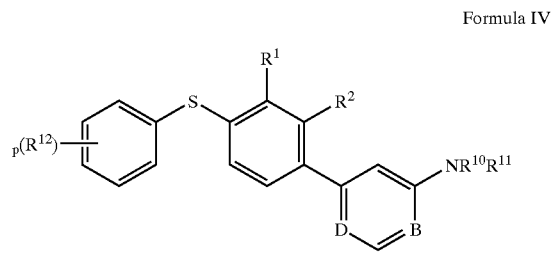

Formula IV wherein D and B axe each independently selected from the group consisting of —N= and —$CR^6$=;

$R^1$ and $R^2$ are each independently selected from the group consisting of hydrogen, halogen and haloalkyl;

$R^{10}$ and $R^{11}$ are as defined above for Formula I;

$R^{12}$, at each occurrence, is independently selected from the group consisting of halogen, alkyl, haloalkyl, alkoxy, carboxyalkoxy, carboxyalkyl and heterocyclyl;

p is an integer of zero to five; and wherein $R^1$, $R^2$, $R^{10}$, $R^{11}$, and $R^{12}$ are unsubstituted or substituted with at least one electron donating group or electron withdrawing group.

Presently most preferred, but not required, compounds are of Formula IV, where p can be one; $R^{12}$ can be halogen, alkyl, alkoxy, carboxyalkoxy, carboxyalkyl or heterocyclyl; and $R^{10}$ and $R^{11}$ can be taken together with N to form a three to seven membered heterocyclyl ring; said ring being piperidine, piperazine, morpholine, pyrrolidine or azetidine.

The compounds represented by structural Formula I, above, may be prepared by synthetic processes or by metabolic processes. Processes for the preparation of the compounds of the present invention by metabolic processes include those occurring in the human or animal body (in vivo) or by processes occurring in vitro.

The present invention is also directed to a method of treatment or prophylaxis in which the inhibition of inflammation or suppression of immune response is desired, comprising administering an effective amount of a compound having Formula I.

In yet another embodiment of the invention are disclosed pharmaceutical compositions containing compounds of Formula I.

DETAILED DESCRIPTION OF THE INVENTION

Definition of Terms

The term "alkanoyl" as used herein refers to an alkyl group attached to the parent molecular group through a carbonyl group.

The term "alkanoylamino" as used herein refers to an alkanoyl group attached to the parent molecular group though an amino group.

The term "alkanoylaminoalkyl" as used herein refers to an alkanoylamino group attached to the parent molecular group through an alkyl group.

The term "alkanoyloxy" as used herein refers to an alkanoyl group attached to the parent molecular group through an oxygen radical.

The term "alkanoyloxyalkyl" as used herein refers to an alkanoyloxy group attached to the parent molecular group through an alkyl group.

The term "alkoxy" as used herein refers to an alkyl group attached to the parent molecular group through an oxygen atom.

The term "alkoxyalkoxy" as used herein refers to an alkoxy group attached to the parent molecular group through an alkoxy group.

The term "alkoxyalkyl" as used herein refers to an alkoxy group attached to the parent molecular group through an alkyl group.

The term "alkoxycarbonyl" as used herein refers to an alkoxy group attached to the parent molecular group through a carbonyl group.

The term "alkoxycarbonylalkyl" as used herein refers to an alkoxycarbonyl group attached to the parent molecular group through an alkyl group.

The term "alkyl" as used herein refers to a saturated straight or branched chain group of 1–10 carbon atoms derived from an alkane by the removal of one hydrogen atom.

The term "alkyl(alkoxycarbonylalkyl)amino" as used herein refers to an amino group substituted with one alkyl group and one alkoxycarbonylalkyl group.

The term "alkyl(alkoxycarbonylalkyl)aminoalkyl" as used herein refers to an alkyl(alkoxycarbonylalkyl)amino group attached to the parent molecular group through an alkyl group.

The term "alkylene" as used herein refers to a divalent group of 1–10 carbon atoms derived from a straight or branched chain alkane by the removal of two hydrogen atoms.

The term "alkylsulfonyl" as used herein refers to an alkyl radical attached to the parent molecular group through an —$SO_2$— group.

The term "alkylsulfonylaminocarbonyl" as used herein refers to an alkylsulfonyl group attached to the parent molecular group through an aminocarbonyl group.

The term "amino" as used herein refers to a radical of the form —$NR_aR_b$, or to a radical of the form —$NR_a$—, where $R_a$ and $R_b$ are independently selected from hydrogen, alkyl or cycloalkyl.

The term "aminoalkanoyl" as used herein refers to an amino group attached to the parent molecular group through an alkanoyl group.

The term "aminoalkyl" as used herein refers to an amino group attached to the parent molecular group through an alkyl group.

The term "aminocarbonyl" as used herein refers to an amino group attached to the parent molecular group through a carbonyl group.

The term "aryl" as used herein refers to a mono- or bicyclic carbocyclic ring system having one or two aromatic rings. The aryl group can also be fused to a cyclohexane, cyclohexene, cyclopentane or cyclopentene ring. The aryl groups of this invention can be optionally substituted with alkyl, halogen, hydroxy, or alkoxy substituents.

The term "arylalkoxy" as used herein refers to an aryl group attached to the parent molecular group through an alkoxy group.

The term "arylalkoxycarbonyl" as used herein refers to an arylalkoxy group attached to the parent molecular group through a carbonyl group.

The term "arylsulfonyl" as used herein refers to an aryl radical attached to the parent molecular group through an —$SO_2$— group.

The term "arylsulfonylaminocarbonyl" as used herein refers to an arylsulfonyl group attached to the parent molecular group through an aminocarbonyl group.

The term "carboxaldehyde" as used herein refers to the radical —CHO.

The term "carboxaldehyde hydrazone" as used herein refers to the radical —CH=N—$NR_cR_d$, where $R_c$ and $R_d$ are independently selected from hydrogen, alkyl or cycloalkyl.

The terms "carboxamide" or "carboxamido" as used herein refer to an amino group attached to the parent molecular group through a carbonyl group.

The term "carboxamidoalkyl" as used herein refers to a carboxamido group attached to the parent molecular group through an alkyl group.

The term "carboxy" as used herein refers to the radical —COOH.

The term "carboxyalkyl" as used herein refers to a carboxy group attached to the parent molecular group through an alkyl group.

The term "carboxyalkylamino" as used herein refers to a carboxyalkyl group attached to the parent molecular group through an amino group.

The term "carboxyalkoxy" as used herein refers to a carboxy group attached to the parent molecular group through an alkoxy group.

The term "carboxycarbonyl" as used herein refers to a carboxy group attached to the parent molecular group through a carbonyl group.

The term "carboxycycloalkoxy" as used herein refers to a carboxy group attached to the parent molecular group through a cycloalkoxy group.

The term "carboxythioalkoxy" as used herein refers to a carboxy group attached to the parent molecular group through a thioalkoxy group.

The term "cyano" as used herein refers to the radical —CN.

The term "cycloalkyl" as used herein refers to a monovalent saturated cyclic or bicyclic hydrocarbon group of 3–12 carbons derived from a cycloalkane by the removal of a single hydrogen atom. Cycloalkyl groups may be optionally substituted with alkyl, alkoxy, halo, or hydroxy substituents.

The term "cycloalkoxy" as used herein refers to a monovalent saturated cyclic or bicyclic hydrocarbon group of 3–12 carbons derived from a cycloalkane by the removal of a single hydrogen atom, linked to the parent molecular group through an oxygen atom. Cycloalkoxy groups may be optionally substituted with alkyl, alkoxy, halo or hydroxy groups.

The terms "halo" or "halogen" as used herein refers to F, Cl, Br, or I.

The term "haloalkyl" as used herein refers to an alkyl group substituted with one or more halogen atoms.

The terms "heterocycle" or "heterocyclyl" represent a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" or "heterocyclic" as used herein additionally refers to bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

Heterocyclics also include bridged bicyclic groups where a monocyclic heterocyclic group is bridged by an alkylene group such as

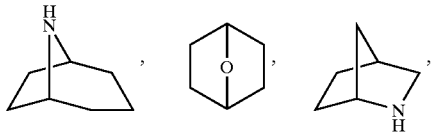

and the like.

Heterocyclics also include compounds of the formula

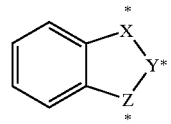

where X* and Z* are independently selected from —CH$_2$—, —CH$_2$NH—, —CH$_2$O—, —NH— and —O—, with the proviso that at least one of X* and Z* is not —CH$_2$—, and Y* is selected from —C(O)— and —(C(R")$_2$)$_v$—, where R" is hydrogen or alkyl of one to four carbons, and v is 1–3. These heterocycles include 1,3-benzodioxolyl, 1,4-benzodioxanyl, 1,3-benzimidazol-2-one and the like. The heterocycle groups of this invention can be optionally substituted with alkyl, halogen, hydroxy or alkoxy substituents.

The term "heterocyclylalkyl" as used herein refers to a heterocyclic group attached to the parent molecular group through an alkyl group.

The term "heterocyclylalkylamino" as used herein refers to an heterocyclylalkyl group attached to the parent molecular group through an amino group.

The term "heterocyclylalkylaminocarbonyl" as used herein refers to a heterocyclylalkylamino group attached to the parent molecular group through a carbonyl group.

The term "heterocyclylamino" as used herein refers to a heterocyclyl group attached to the parent molecular group through an amino group.

The term "heterocyclylcarbonyl" as used herein refers to a heterocyclyl group attached to the parent molecular group through a carbonyl group.

The term "heterocyclylsulfonyl" as used herein refers to a heterocyclyl radical attached to the parent molecular group through an —SO$_2$— group.

The term "heterocyclylsulfonylaminocarbonyl" as used herein refers to a heterocyclylsulfonyl group attached to the parent molecular group through an aminocarbonyl group.

The term "hydroxyalkanoyl" as used herein refers to a hydroxy radical attached to the parent molecular group through an alkanoyl group.

The term "hydroxyalkoxy" as used herein refers to a hydroxy radical attached to the parent molecular group through an alkoxy group.

The term "hydroxyalkoxyalkyl" as used herein refers to a hydroxyalkoxy group attached to the parent molecular group through an alkyl group.

The term "hydroxyalkyl" as used herein refers to a hydroxy radical attached to the parent molecular group through an alkyl group.

The term "hydroxyalkylaminocarbonyl" as used herein refers to a hydroxyalkyl group attached to the parent molecular group through an aminocarbonyl group.

The term "perfluoroalkyl" as used herein refers to an alkyl group in which all of the hydrogen atoms have been replaced by fluoride atoms.

The term "phenyl" as used herein refers to a monocyclic carbocyclic ring system having one aromatic ring. The phenyl group can also be fused to a cyclohexane or cyclopentane ring. The phenyl groups of this invention can be optionally substituted with alkyl, halogen, hydroxy or alkoxy substituents.

The term "pharmaceutically-acceptable prodrugs" as used herein represents those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. The term "sulfonate" as used herein refers to the radical —SO$_3$H.

The term "tetrazole" or "tetrazolyl" as used herein refers to the heterocyclic radical —CN$_4$H.

The term "thioalkoxy" as used herein refers to an alkyl group attached to the parent molecular group through a sulfur atom.

The term "trans-cinnamyl" as used herein refers to an acrylamido group (aminocarbonylethenyl) attached to the parent molecular group through C-3 of the acrylamido group, such that the aminocarbonyl and the parent molecular group exist in a trans relationship about the ethenyl group.

The term "lower" refers to a $C_1$–$C_6$ unit for a particular functionality. For example, "lower alkyl" means $C_1$–$C_6$ alkyl.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogen, trifluoromethoxy, trifluoromethyl, aralkyl, alkenyl, alkynyl, aryl, carboxyalkoxy, carboxyalkyl, cycloalkyl, cycloalkylalkyl, heterocyclyl, alkylheterocyclyl, heterocyclylalkyl, oxo, arylsulfonaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference.

Electron withdrawing groups include halo, nitro, carboxyl, lower alkenyl, lower alkynyl, carboxaldehyde, carboxyamido, aryl, quaternary ammonium and trifluoromethyl among others. Electron donating groups include such groups as hydroxy, lower alkyl, amino, lower alkylamino, di(lower alkyl)amino, aryloxy, mercapto, lower alkylthio, lower alkylmercapto and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkylamino), amine lower mercapto, mercaptoalkyl, alkylthio and alkyldithio.

As used herein, the term "composition" is intended to encompass a product comprising the specified ingredients in the specified amounts, as well as any product which results, directly or indirectly, from a combination of the specified ingredients in the specified amounts.

Compounds of the present invention can exist as stereoisomers wherein asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and mixtures of enantiomers or diastereomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon—carbon double bond or arrangement of substituents around a carbocyclic ring. Substituents around a carbon—carbon double bond are designated as being in the Z or E configuration wherein the term "Z" represents substituents on the same side of the carbon—carbon double bond and the term "E" represents substituents on opposite sides of the carbon—carbon double bond. The arrangement of substituents around a carbocyclic ring are designated as cis or trans wherein the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated cis/trans.

As is apparent from the foregoing descriptions, the compounds of Formula I are useful in a variety of forms, i.e., with various substitutions as identified. Examples of particularly desirable compounds are quite diverse, and many are mentioned herein.

Compounds of the present invention include, but are not limited to: 1-(6-(4-(2-isopropyl-phenylsulfanyl)-3-trifluoromethyl-phenyl)-pyrimidin-4-yl)-piperidine-3-carboxylic acid, 4-(4-(2-isopropyl-phenylsulfanyl)-3-trifluoromethyl-phenyl)-6-(3-(2H-tetrazol-5-yl)-piperidin-1-yl)-pyrimidine, 4-(4-(2-isopropyl-phenylsulfanyl)-3-trifluoromethyl-phenyl)-6-(4-(2H-tetrazol-5-yl)-piperidin-1-yl)-pyrimidine, (1-(6-(4-(2-isopropyl-phenylsulfanyl)-3-trifluoromethyl-phenyl)-pyrimidin-4-yl)-piperidin-3-yl)-menthanol, 2-(1-(6-(4-(2-isopropyl-phenylsulfanyl)-3-trifluoromethyl-phenyl)-pyrimidin-4-yl)-piperidin-4-yl)-ethanol, N-(1-(4-(4-(2-isopropyl-phenylsulfanyl)-3-trifluoromethyl-phenyl)-pyridin-2-yl)-pyrrolidin-3-yl)-acetamide, 1-(4-(4-(2-methoxy-phenylsulfanyl)-3-trifluoromethyl-phenyl)-pyridin-2-yl)-pyrrolidine-3-ol, N-1-(4-(4-(2-methoxy-phenylsulfanyl)-3-trifluoromethylphenyl)-pyridin-2-yl)-pyrrolidine-3-yl)-acetamide, N-1-(4-(4-(2-methoxy-phenylsulfanyl)-3-trifluoromethyl-phenyl)-pyridin-2-yl)-pyrrolidine-3-yl)-acetamide, N-(1-(4-(4-(2,3-dihydro-benzo(1,4)dioxin-6-ylsulfanyl)-3-trifluoromethyl-phenyl)-pyridin-2-yl)-pyrrolidin-3-yl)-acetamide, 4'-(4-(2, 3-dihydro-benzo(1,4)dioxin-6-ylsulfanyl)-3-trifluoromethyl-phenyl)-3,4,5,6-tetrahydro-2H-(1,2') bipyridinyl-4-carboxylic acid and 4'-(4-(2,3-dihydro-benzo (1,4)dioxin-6-ylsulfanyl)-3-trifluoromethyl-phenyl)-3,4,5, 6-tetrahydro-2H-(1,2')bipyridinyl-3-carboxylic acid.

Abbreviations

Abbreviations which have been used in the schemes and the examples which follow are: DCM for methylene dichloride; EWG for electron withdrawing group; NMP for N-methylpyrrolidinone; sat. for saturated; THF for tetrahydrofuran; TFA for trifluoroacetic acid; ; BINAP for 2,2'-bis (diphenylphosphino)-1,1'-binaphthyl; DMSO for dimethylsulfoxide; MCPBA for meta-chloroperbenzoic acid; DMF for dimethylformamide; TLC for thin layer chromatography; HPLC for high pressure liquid chromatography; APCI for atmospheric pressure chemical ionization; ESI for electrospray ionization; DCI for direct chemical ionization; LFA for lymphocyte function-associated antigen; and ICAM for intercellular adhesion molecule.

Pharmaceutical Compositions and Methods of Treatment

The present invention also provides pharmaceutical compositions which comprise compounds of the present invention formulated together with one or more pharmaceutically-acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar—agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well-known in the art. For example, S. M. Berge, et al. describe pharmaceutically-acceptable salts in detail in *J. Pharmaceutical Sciences*, 1977, 66: 1 et seq. The salts may be prepared in situ during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically-acceptable basic addition salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically-acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.1 to about 50 mg, more preferably of about 5 to about 20 mg of active compound per kilogram of body weight per day are administered orally or intravenously to a mammalian patient. If desired, the effective daily dose may be divided into multiple doses for purposes of administration, e.g. two to four separate doses per day.

Preparation of Compounds of this Invention

The compounds and processes of the present invention may be better understood in connection with the following synthetic schemes which illustrate the methods by which the compounds of the invention can be prepared.

Scheme 1 describes compounds of Formula I, which contain an oxazole ring n=0, Y=N, B=O, D=C). In Scheme 1, and likewise in Schemes 2 and 4, the substituent X is a leaving group. In Scheme 1, Aryl methyl ketone 1, with an appropriate substitution ($R^{1-2}$ and $R^{4-5}$), and a leaving group X, reacts with an aryl thiol to give a biaryl sulfide 2. Biarylsulfide 2 can be converted into an alpha-bromomethyl ketone 3 using a variety of reagents including $Bu_4NBr_3$. Condensation of 3 with a urea gives a desired oxazole compound 4.

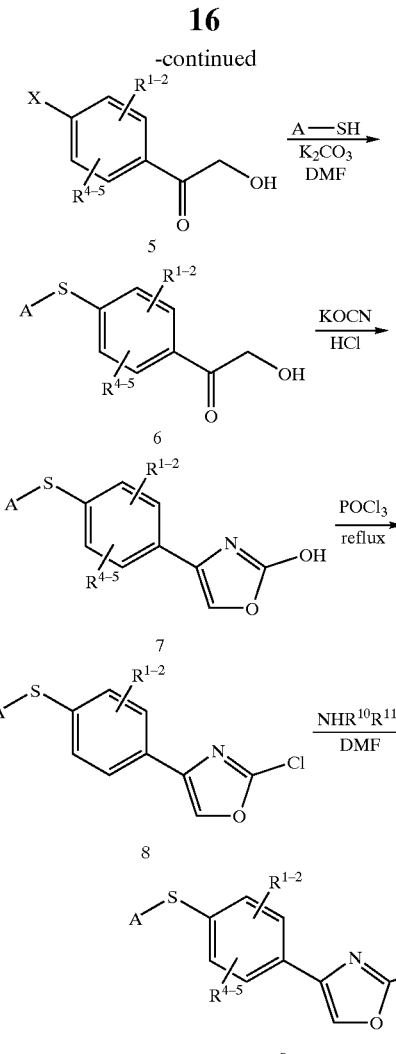

Another method of preparing compounds of Formula I containing an oxazole ring (n=0, Y=N, B=O, D=C) is illustrated in Scheme 2. In Scheme 2, an aryl methyl keton 1 is converted into an alpha-hydroxymethyl ketone 5, which then can be reacted with an arythiol to give a biaryl sulfide 6. Acid-catalyzed condensation of 6 with KOGN affords a 2-hydroxy oxazole 7, which can be converted into a 2-chloro-oxazole 8 using $POCl_3$. Displacement of the chloride of 8 with an amine gives a desired 2-amino-oxazole 9.

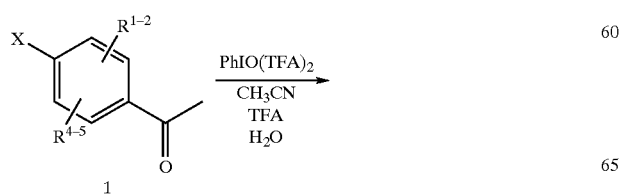

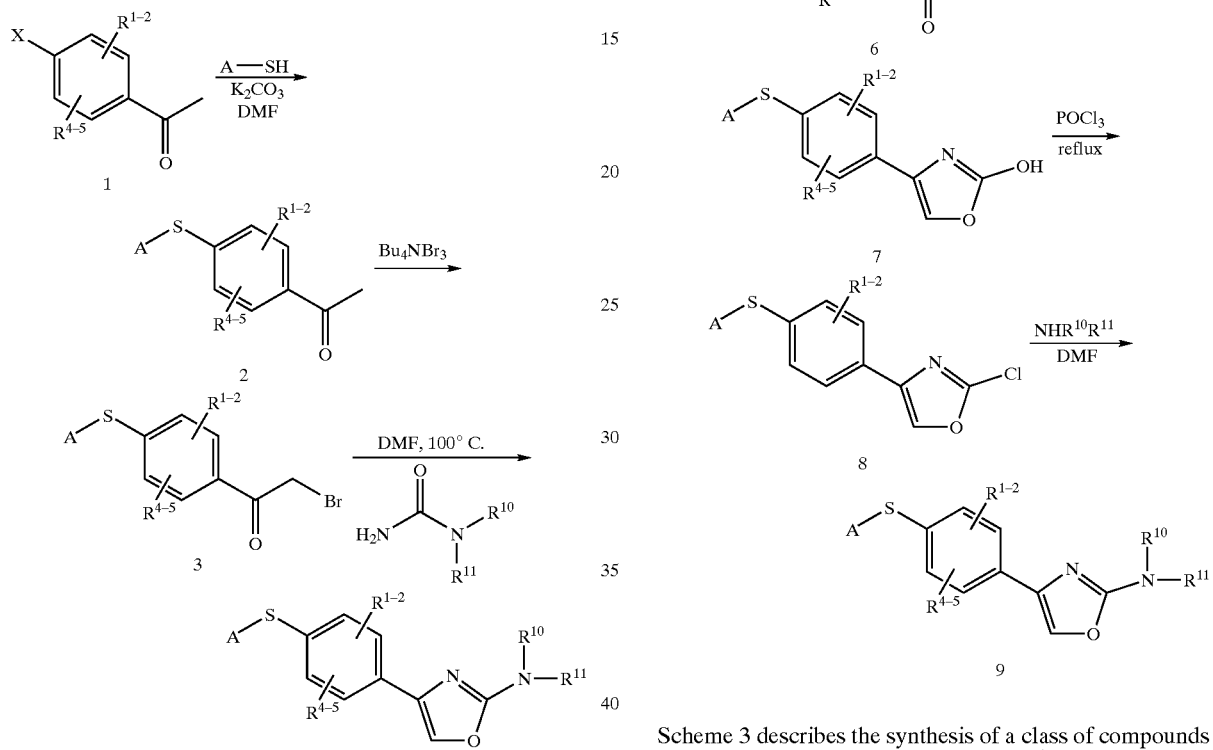

Scheme 3 describes the synthesis of a class of compounds of Formula I containing thioazole ring (n=0, Y=N, B=S, D=C). In Scheme 3, biaryl sulfide alpha-bromomethy ketone 3 can be prepared following the procedure outline in Scheme 1. Condensation of with a properly substituted thiourea gives a desired 2-aminothioazole 10.

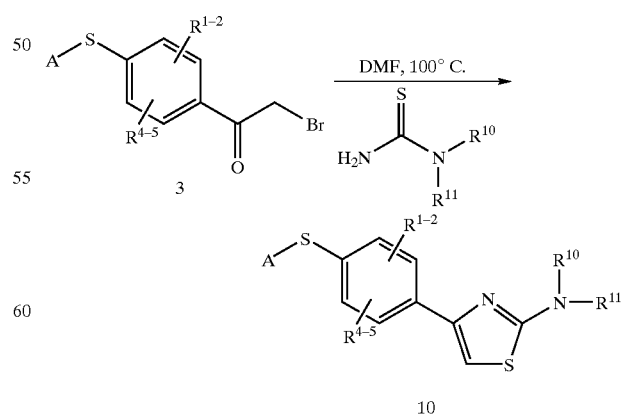

Another class of compounds of Formula I are compounds containing a pyrimidine ring, for example 4,6-disubstituted pyrimidines (n=1, Y=C, B=N, Z=C, D=N). Scheme 4 describes one procedure for the preparation of this class of compounds. Reaction of a biaryl sulfide methyl ketone 2 with diethyl carbonate under base-catalysis leads to a beta-ketoester 11. Condensation of 11 with formamidine gives a 4-hydroxy pyrimidine 12. which can be converted into a 4-chloropyrimidine 13. Displacement of the chloride of 13 by an amine gives a desired 4-amino-pyrimidine 14.

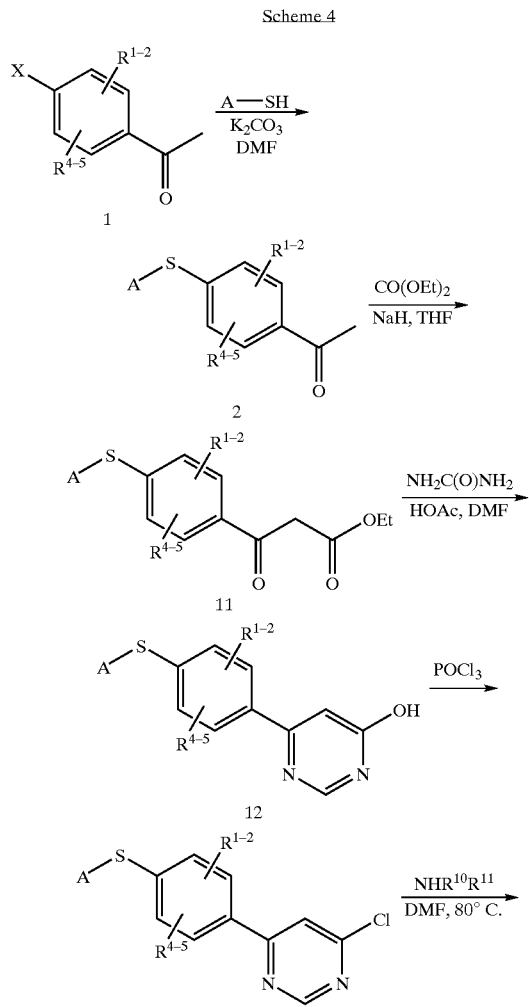

An alternative synthesis of 4,6-disubstituted pyrimidines is illustrated in Scheme 5. In Scheme 5, nucleophilic substitution of an aryl fluoride 15 with an aryl thio under base-catalysis gives a biaryl sulfide 16. Transmetallation of 16 with n-BuLi/ZnCl$_2$ followed by Pd-catalyzed cross-coupling with a 4,6-diiodopyrimidine leads to an iodopyrimidine 17. Reaction of 17 with a selected amine gives a desired 4-aminopyrimidine 14.

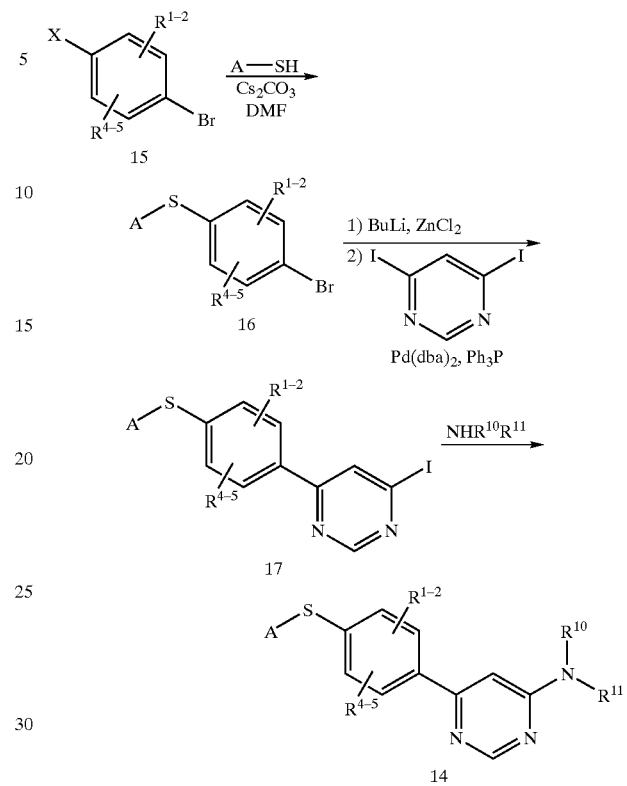

Yet another class of compounds of Formula I are compounds containing a pyridine ring, for example 2,4-disubstituted pyridines (n=1, Y=C, B=N, Z=C, D=C). Scheme 5 describes one procedure for the preparation of this class of compounds. In Scheme 6, Pd catalyzed cross-coupling of a properly substituted 1-bromo-4-fluoro-benzene 15 and 4-pyridine boronic acid gives compound 18. Oxidation of 18 with MCPBA leads to a pyridinium oxide 19. Displacement of the fluoride of 19 with an aryl thio affords biarylsulfide 20. Treatment of 20 with POCl$_3$, leads to 2-chloropyridine 21. Finally, reaction of 21 with a selected amine gives a desired 2-aminopyridine 22.

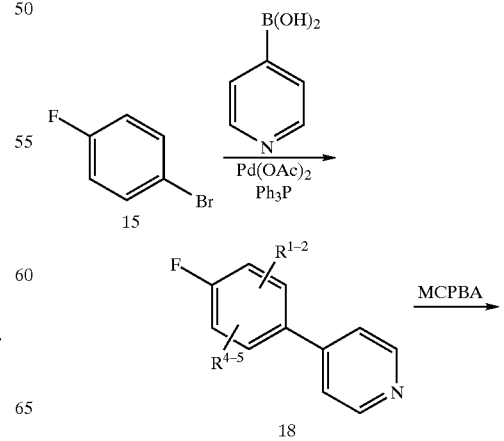

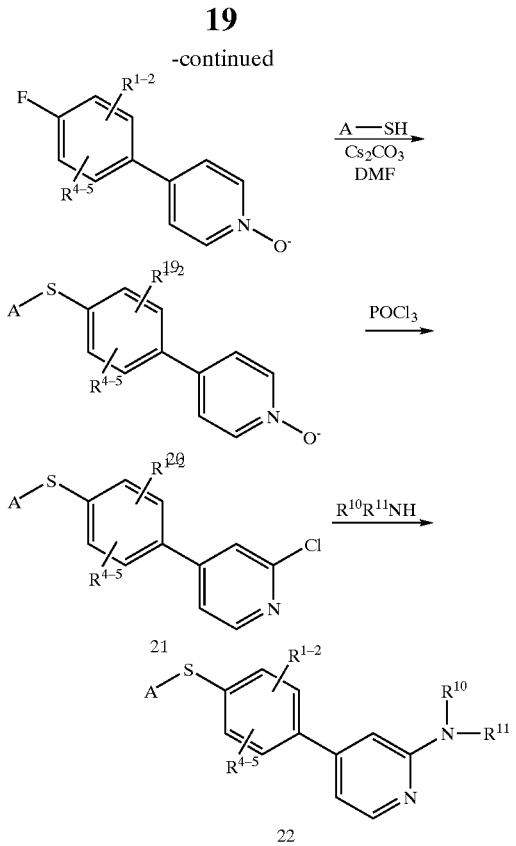

The compounds and processes of the present invention will be better understood in connection with the following examples which are intended as an illustration of and not a limitation upon the scope of the invention.

EXAMPLE 1

1-{4-[4-(2-Isopropyl-phenylsulfanyl)-3-trifluoromethyl-phenyl]-oxazol-2-yl}-piperidine 23 was synthesized as follows.

1A. First, 1-(4-isopropyl-phenylsulfanyl)-3-trifluoromethyl-phenyl)-ethanone 24 was prepared as follows. To a solution of o-isopropyl thiophenol (2.46 ml, 15 mmole) and 4-fluoro-3-trifluoromethyl acetophenone (3.0 g, 14.6 mmole) in 100 ml of DMF was added $Cs_2CO_3$ (7.15 g, 22 mmole). After stirring for 3 hours, the mixture was filtered and solvent was removed by evaporation. The residue was chromatographed on a silica gel column, eluting with 5% EtOAc in hexane, giving 4.70 g of a white solid 24. Yield: 96.6%. $^1$H-NMR (CDCl$_3$, 300 MHz) δ 1.18 (d, J=6.6 Hz, 6H), 2.56 (s, 3H), 3.45 (heptet, J=6.6 Hz, 1H), 6.81 (d, J=8.4 Hz, 1H), 7.26 (m, 1H), 4.48 (d, J=1.8 Hz, 1H), 7.50 (d, J=1.8 Hz, 1H), 7.53 (d, J=8.1 Hz, 1H), 7.79 (d, J=8.1 Hz, 1H), 8.21 (d, J=1.8 Hz, 1H); MS (DCI/NH$_3$) m/z 339 (M+H)$^+$; 356 (M+NH$_4$)$^+$.

1B. Then 2-bromo-1-(4-isopropyl-phenylsulfanyl)-3-trifluoromethyl-phenyl)-ethanone 25 was prepared as follows. Compound 24 (4.72 g, 14.0 mmole) and tetrabutylammonium tribromide (7.6 g, 15.4 mmole) was dissolved in a mixture of 20 ml of MeOH and 50 ml of DCM. The solution was stirred at ambient temperature overnight. The solvent was then evaporated and the residue was chromatographed on a silica gel column, eluting with 10% EtOAc in hexane. An off-white solid 25 was obtained, 5.9 g, 100%. $^1$H-NMR (CDCl$_3$, 300 MHz) δ 1.18 (d, J=6.9 Hz, 6H), 3.45 (heptate, J=6.9 Hz, 1H), 4.35 (s, 2H), 6.81 (d, J=8.4 Hz, 1H), 7.29 (d.d, J=2.4, 6.3 Hz, 1H), 7.48 (d, J=1.8 Hz, 1H), 7.48–7.56 (m, 3H), 7.81 (d.d, J=2.4, 6.3 Hz, 1H), 7.79 (d, J=8.1 Hz, 1H), 8.24 (d, J 1.8 Hz, 1H); MS (DCI/NH$_3$) m/z 418 (M+H)$^+$; 434 (M+NH$_4$)$^+$.

1C. A solution of compound 25 (22 mg, 0.05 mmole) and 1-carbamyl piperidine (32 mg, 0.25 mmole) was stirred at 105° C. for 2 hours. DMF was then evaporated and the residue purified on a preparative HPLC system with a C$_8$ reverse-phase column using 10 mM H$_4$NOAc (aq.) and CH$_3$CN as the mobile phase. The product 23 was obtained as a yellow solid (16 mg) from the HPLC fractions by evaporating the solvents on a speedvac. $^1$H-NMR (CDCl$_3$, 300 MHz) δ 1.18 (d, J=6.9 Hz, 6H), 1.5–1.7 (m, 6H), 3.5–3.7 (m, 5 H), 6.91 (d, J=8.4 Hz, 1H), 7.34–7.38 (m, 3H), 7.47 (s, 1H), 7.58–7.60 (m, 1H), 7.96 (s, 1H). MS (APCI) m/z 447 (M+H)$^+$.

EXAMPLE 2

1-(4-(4-(2-Isopropyl-phenylsulfanyl)-3-trifluoromethyl-phenyl)-oxazol-2-yl)piperidine 26 was synthesized according to the following procedure.

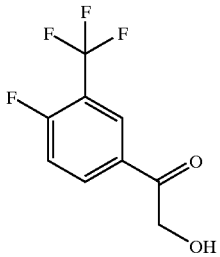

2A. First, 1-(4-fluoro-3-trifluoromethyl-phenyl)-2-hydroxy-ethanone 27 was prepared as follows. To a solution of 1-fluoro-3-trifluoroacetophenone (1.0 g, 5.0 mmole) in acetonitrile (15 ml) and water (3 ml) was added trifluoroacetic acid (0.77 ml, 10 mmole) and bis-(trifluoroacetoxyl) iodobenzene (4.3 g, 10 mmole). The mixture was refluxed for three hours. The solution was concentrated and then extracted with EtOAc (3×30 ml). The combined organic solution was washed with 5% aq. NaHCO$_3$ and dried. After filtration and solvent evaporation, the residue was chromatographed on a silica gel column, eluting with 30% EtOAc in hexane, giving 0.47 g of a white solid 27, 37.8% yield. $^1$H-NMR (CDCl$_3$, 300 MHz) δ 3.28 (br s, 1 H), 4.89 (s, 2H), 7.36 (t, J=9 Hz, 1H), 8.12–8.17 (m, 1H), 8.21 (d, J=6 Hz, 3H); MS (APCI) m/z 223 (M+H)$^+$.

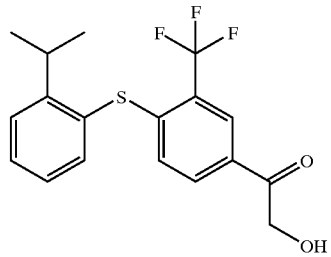

2B. Then 2-hydroxy-1-(4-(2-isopropyl-phenylsulfanyl)-3-trifluoromethyl-phenyl)-ethanone 28 was prepared as follows. To a solution of compound 27 (0.4 g, 1.8 mmole) and o-isopropylthiophenol (0.31 ml, 1.8 mmole) in DMF (10 ml) was added Cs$_2$CO$_3$ (0.59 g, 1.8 mmole). The mixture was stirred for 10 minutes and EtOAc (30 ml) was added. The mixture was filtered, concentrated and chromatographed on a silica gel column eluting with 30% EtOAc in hexane. The desired product 28 was obtained as an oil, 0.22 g, 34.8%. $^1$H-NMR (CDCl$_3$, 300 MHz) δ 1.17 (d, J=7.0 Hz, 6 H), 3.40–3.46 (m, 2 H), 4.80 (s, 2H), 6.82 (d, J=8.4 Hz, 1H), 7.27–7.31 (m, 1H), 7.51–7.55 (m, 3H), 7.72 (d, J=8.4 Hz, 1H), 8.17 (s, 1H); MS (DCI/NH$_3$) m/z 355 (M+H)$^+$, 372 (M+NH$_4$)$^+$.

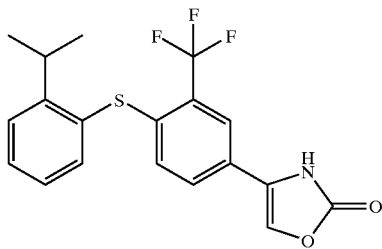

2C. Then 4-(4-(2-isopropyl-phenylsulfanyl)-3-trifluoromethyl-phenyl)-3H-oxaxol-2-one 29 was prepared as follows. To a solution of compound 28 (0.22 g, 0.62 mmole) and potassium cyanate 0.25 g, 3.0 mmole) in DMF 5.0 ml) was added 0.5 ml of 4 M HCl in dioxane. The mixture was stirred at ambient temperature for 3 hours and another 0.25 ml of 4 M HCl in dioxane was added. The mixture was stirred for another 10 minutes and then quenched with water (20 ml). The layers were separated and the organic layer was extracted with EtOAc. The combined organic solution was dried, filtered and concentrated. Chromatography of the residue gave the title compound 29 as a yellow solid. 194 mg, 82.6%. $^1$H-NMR (CDCl$_3$, 300 MHz) δ 1.18 (d, J=7.0 Hz, 6H), 3.48 (heptet, J=7.0 Hz, 1H), 6.87 (d, J=8.1 Hz, 1H), 7.11 (s, 1H), 7.27 (m, 2H), 7.44–7.48 (m, 3H), 7.64 (s, 1H), 9.75 (s, 1H); MS (DCI/NH$_3$) r/z 397 (M+NH$_4$)$^+$.

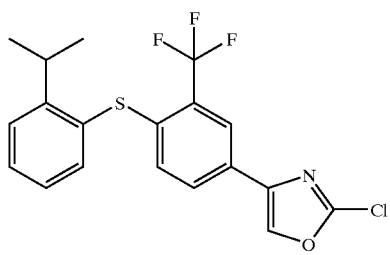

2D. Then, 2-chloro-4-(4-(2-isopropyl-phenylsulfanyl)-3-trifluoromethyl-phenyl)-oxazole 30 was prepared as follows. A solution of compound 29 (197 mg, 0.52 mmole) and diethylphenylamine (0.085 ml) in phosphorus oxychloride (5.0 ml) was refluxed for two hours. The mixture was then concentrated and the residue was quenched with ice-water, followed by extraction with EtOAc. The EtOAc solution was dried, filtered and concentrated. The residue was chromatographed on a 10-g silica gel cartridge, eluting with 30% EtOAc in hexane. The title compound 30 was obtained as a yellow solid. 97 mg, 47.0% yield. $^1$H-NMR (CDCl$_3$, 300 MHz) δ 1.19 (d, J=7.0 Hz, 6H), 3.50 (heptet, J=7.0 Hz, 1H), 6.88 (d, J=8.1 Hz, 1H), 7.20–7.23 (m, 1H), 7.42–7.44 (m, 3H), 7.55 (d, J=8.1 Hz, 1H), 7.90 (s, 1H), 7.97 (s, 1H); MS (DCI/NH$_3$) m/z 398 (M+H), 415 (M+NH$_4$)$^+$.

2E. A solution of compound 30 (20 mg, 0.05 mmole) and 1-acetyl piperazine (19.2 mg, 0.15 mmole) in toluene (1.0 ml) was stirred at 100° C. for five hours. Solvent was evaporated and the residue was purified on a 5-g silica gel cartridge eluting with EtOAc. The title compound 26 was obtained as a white solid. 11.2 mg, 45.8%. $^1$H-NMR (CDCl$_3$, 300 MHz) δ 1.18 (d, J=7.0 Hz, 6H), 2.15(s, 3H), 3.49–3.62 (m, 7H) 3.74 (m, 2H), 6.89 (d, J=8.0 Hz, 1H), 7.15–7.21 (m, 2H), 7.39–7.41 (m, 2H), 7.52 (s, 1H), 7.58 (d, J=8.0 Hz, 1H), 7.96 (s, 1H); MS (APCI) m/z 490(M+H)$^+$.

EXAMPLE 3

1-(4-(4-(2-Isopropyl-phenylsulfanyl)-3-trifluoromethyl-phenyl)-thiazol-2-yl)-piperazin-1-yl)-ethanone 31 was synthesized according to the following procedure.

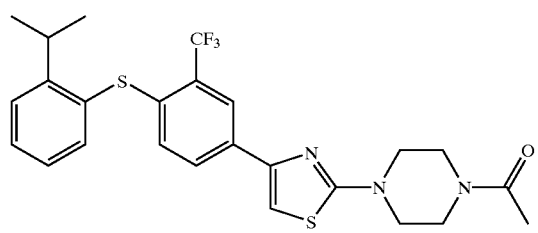

A solution of compound 25 (40 mg, 1.0 mmole) and 1-acetyl-4-thiocarbamyl piperazine (19 mg, 0.1 mmole) in 1.0 ml of DMF was stirred at ambient temperature for 16 hours. Then the solvent was evaporated and the residue was purified on a preparative HPLC with a C₈ reverse phase column, eluting with a gradient of acetonitrile and 10 mM NH₄OAc buffer. The title compound 31 was obtained as a yellow solid. 45 mg, 80.0% yield. ¹H-NMR (CDCl₃, 300 MHz) δ 1.12 (d, J=6.0 Hz, 6H), 2.08 (s, 3H), 3.40–3.49 (m, 3H), 3.55 (br s, 2H), 3.71 (m, 2H), 6.74 (s, 1H), 6.83 (d, J=6.0 Hz, 1H), 7.08–7.13 (m, 1H), 7.31–7.34 (m, 3H), 7.64 (d, J=6.0 Hz, 1H), 8.05 (s, 1H); MS (DCI/NH₃) m/z 4.90 (M+H)⁺.

EXAMPLE 4

(4-(4-(2-Isopropyl-phenylsulfanyl)-3-trifluoromethyl-phenyl)-thiazol-2-yl)-(3-methoxy-propyl)-amine 32 was synthesized according to the following procedure.

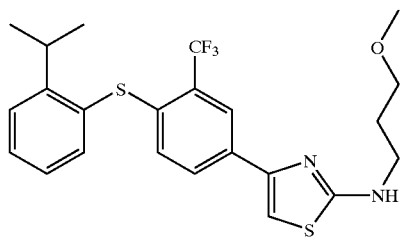

32

The title compound was prepared according to the procedure of Example 3 from compound 25 (20 mg, 0.05 mmole) and N-(1-methoxy)propyl thiourea (14.8 mg, 0.1 mmole). Yield: 11.7 mg, 50.8%. ¹H-NMR (CDCl₃, 500 MHz) δ 1.18 (d, J=8.5 Hz, 6H), 1.95 (pentaplet, J=8.0 Hz, 2H), 3.36 (s, 3H), 3.42–3.45 (m, 2H), 3.51–3.54 (m, 3H), 6.66 (s, 1H), 6.90 (d, J=10.5 Hz, 1H), 7.17–7.20 (m, 1H), 7.39–7.42 (m, 3H), 7.68 (dd, J=10.5 and 2.0 Hz, 1H), 8.06 (d, J=2.0 Hz, 1H). MS (DCI/NH₃) m/z 467 (M+H)⁺.

EXAMPLE 5

1-(4-(4-(2-Isopropyl-phenylsulfanyl)-3-trifluoromethyl-phenyl)-thiazol-2-yl)-piperidine 33 was synthesized according to the following procedure.

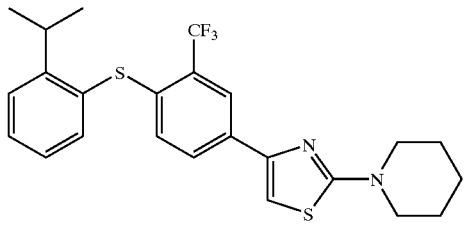

33

The title compound was prepared according to the procedure of Example 3 from compound 25 (20 mg, 0.05 mmole) and 1-thiocarbamyl-piperidine (14.4 mg, 0.1 mmole). Yield: 4.9 mg, 10.6%. ¹H-NMR (CDCl₃, 500 MHz) δ 1.18 (d, J=8.5 Hz, 6H), 1.95 (pentet, J=8.0 Hz, 2H), 1.56–1.72 (m, 6H), 3.50–3.55 (m, 5H), 6.70 (s, 1H), 6.91 (d, J=10.5 Hz, 1H), 7.15–7.19 (m, 1H), 7.37–7.40 (m, 3H), 7.78 (dd, J=10.5 and 2.0 Hz, 1H), 8.11 (d, J=2.0 Hz, 1H); MS (DCI/NH₃) m/z 463 (M+H)⁺.

EXAMPLE 6

(4-(4-(2-Isopropyl-phenylsulfanyl)-3-trifluoromethyl-phenyl)-thiazol-2-yl)-(3-morpholin-4-yl-propyl)-amine 34 was synthesized according to the following procedure.

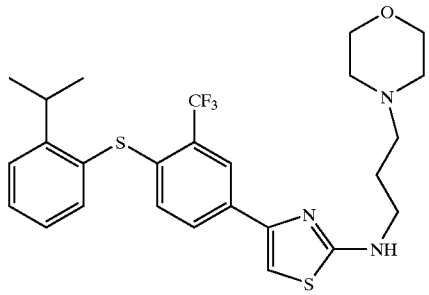

34

The title compound was prepared according to the procedure of Example 3 from compound 25 (20 mg, 0.05 mmole) and N-[1-(1'-morpholinyl)]propylthiourea (19 mg, 0.1 mmole). Yield: 25.4 mg, 97.7%. ¹H-NMR (CDCl₃, 500 MHz) δ 1.18 (d, J=8.5 Hz, 6H), 1.86–1.89 (m, 2H), 2.54–2.59 (m, 6H), 3.52 (heptet, J=8.5 Hz, 1H), 3.77–3.79 (m, 4H), 6.68 (s, 1H), 6.91 (d, J=10.5 Hz, 1H), 7.15–7.19 (m, 1H), 7.38–7.40 (m, 3H), 7.69 (dd, J=10.5 and 2.0 Hz, 1H), 8.10 (d, J=2.0 Hz, 1H); MS (DCI/NH₃) m/z 522 (M+H)⁺.

EXAMPLE 7

(4-(4-(2-Isopropyl-phenylsulfanyl)-3-trifluoromethyl-phenyl)-thiazol-2-yl)-(2-methoxy-ethyl)-amine 35 was synthesized according to the following procedure.

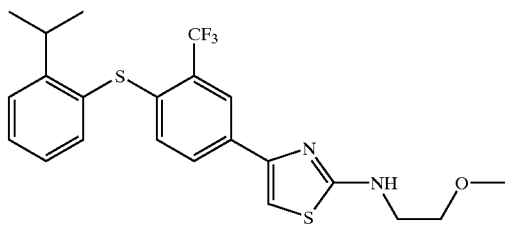

35

The title compound was prepared according to the procedure of Example 3 from compound 25 (20 mg, 0.05 mmole) and N-(1-methoxyl)ethylthiourea (14 mg, 0.1 mmole). Yield: 11 mg, 50%. ¹H-NMR (CDCl₃, 500 MHz) δ 1.18 (d, J=8.5 Hz, 6H), 3.39 (s, 3H), 3.50–3.55 (m, 3H), 3.62 (t, J=5.5 Hz, 2H), 6.68 (s, 1H), 6.90 (d, J=10.5 Hz, 1H), 7.16–7.21 (m, 1H), 7.38–7.42 (m, 3H), 7.68 (dd, J=10.5 and 2.0 Hz, 1H), 8.07 (d, J=2.0 Hz, 1H); MS (DCI/NH₃) m/z 453(M+H)⁺.

EXAMPLE 8

(4-(4-(2-Isopropyl-phenylsulfanyl)-3-trifluoromethyl-phenyl)-thiazol-2-yl)-(2-morpholin-4-yl-ethyl)-amine 36 was synthesized according to the following procedure.

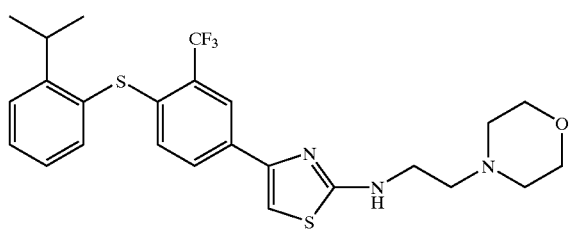

36

The title compound was prepared according to the procedure of Example 3 from compound 25 (20 mg, 0.05 mmole) and N-[1-(1'-morpholinyl)]ethyl thiourea (14 mg, 0.1 mmole). Yield: 20.3 mg, 81.2%. $^1$H-NMR (CDCl$_3$, 500 MHz) δ 1.18 (d, J=8.5 Hz, 6H), 2.56 (br s, 4H), 2.71 (br s, 2H), 3.44 (br s, 2H), 3.52 (heptet, J=8.5 Hz, 1H), 3.76–3.78 (m, 4H), 5.88 (br s, 1H), 6.70 (s, 1H), 6.91 (d, J=10.5 Hz, 1H), 7.15–7.19 (m, 1H), 7.38–7.40 (m, 3H), 7.69 (d, J=10.5 Hz, 1H), 8.12 (d, J=2.0 Hz, 1H); MS (DCI/NH$_3$) m/z 508 (M+H)$^+$.

EXAMPLE 9

(4-(4-(2-Isopropyl-phenylsulfanyl)-3-trifluoromethyl-phenyl)-thiazol-2-yl)-(2-piperidin-1-yl-ethyl)-amine 37 was synthesized according to the following procedure.

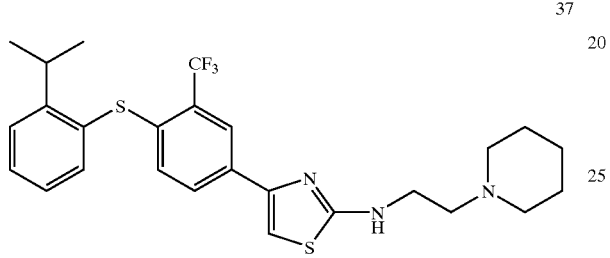

37

The title compound was prepared according to the procedure of Example 3 from compound 25 (20 mg, 0.05 mmole) and N-[1-(1'-piperidinyl)]ethyl thiourea (20 mg, 0.1 mmole). Yield: 21 mg, 85.0%. $^1$H-NMR (CDCl$_3$, 500 MHz) δ 1.18 (d, J=8.5 Hz, 6H), 1.51 (m, 2H), 1.68–1.74 (m, 4H), 2.64 (bs, 4H), 2.80 (t, J=6.5 Hz, 1H), 3.49–3.56 (m, 3H), 4.64 (bs, 1H), 6.68 (s, 1H), 6.90 (d, J=10.5 Hz, 1H), 7.15–7.19 (m, 1H), 7.38–7.41 (m, 3H), 7.69 (d, J=10.5 Hz, 1H), 8.11 (d, J=2.0 Hz, 1H). MS (DCI/NH$_3$) m/z 506 (M+H)$^+$.

EXAMPLE 10

Furan-2-ylmethyl-(4-(4-(2-isopropyl-phenylsulfanyl)-3-trifluoromethyl-phenyl)-thiazol-2-yl)-amine 38 was synthesized according to the following procedure.

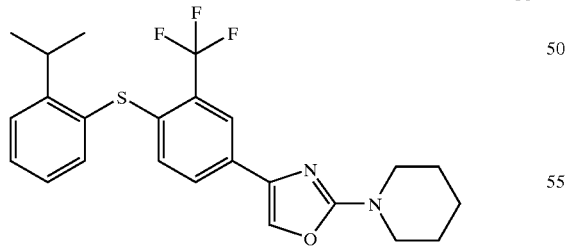

38

The title compound was prepared according to the procedure of Example 3 from compound 25 (20 mg, 0.05 mmole) and N-furfuryl thiourea (16 mg, 0.1 mmole). Yield: 9.4 mg, 40.0%. $^1$H-NMR (CDCl$_3$, 500 MHz) δ 1.18 (d, J=8.5 Hz, 6H), 3.51 (heptet, J=5.5 Hz, 1H), 4.53 (s, 2H), 6.34 (s, 2H), 6.71 (s, 1H), 6.90 (d, J=10.5 Hz, 1H), 7.18–7.21 (m, 1H), 7.38–7.43 (m, 4H), 7.70 (d, J=10.5 Hz, 1H), 8.07 (d, J=2.0 Hz, 1H). MS (DCI/NH$_3$) m/z 475 (M+H)$^+$.

EXAMPLE 11

1-(4-(4-(2,3-Dichloro-4-(2-isopropyl-phenylsulfanyl)-phenyl)-thiazol-2-yl)-piperazin-1-yl)-ethanone 39 was synthesized according to the following procedure.

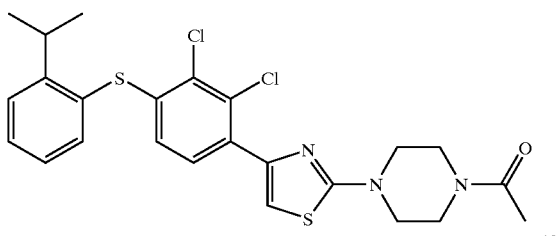

39

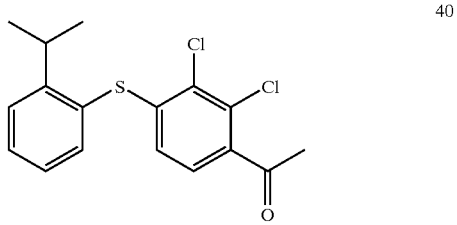

40

11 A. First, 1-(2,3-dichloro-4-(2-isopropyl-phenylsulfanyl)-phenyl)-ethanone 40 was prepared as follows. To a solution of o-isopropyl thiophenol (3.14 g, 25 mmole) and 2,3,4-trichloro-acetophenone (5.9 g, 25 mmole) in DMF (l100 ml) was added Na$_2$CO$_3$ (2.65 g, 25 mmole). The reaction was quenched with water (300 ml) after stirring for 50 hours at ambient temperature. The solution was extracted with EtOAc (3×100 ml). The combined EtOAc solution was dried (MgSO$_4$), filtered and concentrated. The residue was chromatographed on a silica gel column, eluting with 10% EtOAc in hexane, giving the title compound 40 as a white solid, 3.4 g, 40.5%. $^1$H-NMR (CDCl$_3$, 500 MHz) δ 1.19 (d, J=8.5 Hz, 6H), 2.66 (s, 3H), 3.43 (heptaplet, J=8.5 Hz, 1H), 6.42 (d, J=8.4 Hz, 1H), 7.19 (d, J=8.4 Hz, 1H), 7.25–7.30 (m, 1H), 7.48–7.53 (m, 3H). MS (DCI/NH$_3$) m/z 339, 341 (M+H)$^+$; 356, 358 (M+NH$_4$)$^+$.

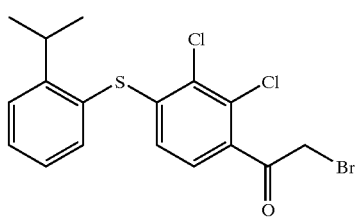

41

11B. Then 2-bromo-1-(2,3-dichloro-4-(2-isopropyl-phenylsulfanyl)-phenyl)-ethanone 41 was prepared as follows. A solution of Br$_2$ (50 mg) in dioxane (1.0 ml) was added to a solution of compound 40 (100 mg, 0.3 mmole) in 2 ml of dioxane. The solution was then stirred for another 10 minutes and concentrated. The residue was dissolved in EtOAc and purified on a 5-g silica gel cartridge, giving the desired product 41 as a white solid. 136 mg, ~100%. $^1$H-NMR (CDCl$_3$, 500 MHz) δ 1.19 (d, J=8.5 Hz, 6H), 3.43 (heptet, J=8.5 Hz, 1H), 4.45 (s, 2H), 6.42 (d, J=8.4 Hz, 1H), 7.19 (d, J=8.4 Hz, 1H), 7.25–7.31 (m, 1H), 7.49–7.54 (m, 3H); MS (DCI/NH$_3$) m/z 436 (M+NH4)$^+$.

11C. A solution of compound 41 (30 mg, 0.07 mmole) and 1-thiocarbamyl-4-acetyl piperazine (20.5 mg, 0.11 mmole)

in DMF (1.0 ml) was stirred at ambient temperature for two hours. The solvent was evaporated and the residue was purified on a 5-g silica gel cartridge, giving the desired product 39 as a white solid. 23 mg, 65.7%. $^1$H-NMR (CDCl$_3$, 500 MHz) δ 1.19 (d, J=8.5 Hz, 6H), 2.14 (s, 3H), 3.46–3.60 (m, 7H),), 3.75–3.78 (m, 2H), 6.48 (d, J=8.4 Hz, 1H), 7.09 (s, 1H), 7.21 (m, 1H), 7.44–7.51 (m, 3H), 7.57 (d, J=8.4 Hz, 1H). MS (DCI/NH$_3$) m/z 506 (M+H)$^+$.

EXAMPLE 12

1-(4-(2,3-Dichloro-4-(2-isopropyl-phenylsulfanyl)-phenyl)-thiazol-2-yl)-piperadine 42 was synthesized according to the following procedure.

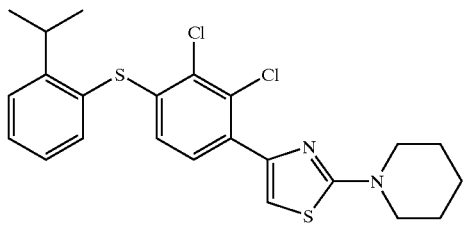

42

The title compound 42 was prepared according to the procedure of Example 11 from compound 41 (30 mg, 0.07 mmole) and 1-thiocarbamyl piperidine. Yield: 21 mg, 65.6%. $^1$H-NMR (CDCl$_3$, 500 MHz) δ 1.19 (d, J=8.5 Hz, 6H), 1.65 (m, 6H), 3.44–3.52 (m, 5H),), 6.48 (d, J=8.4 Hz, 1H), 7.01 (s, 1H), 7.21 (m, 1H), 7.44–7.51 (m, 3H), 7.61 (d, J=8.4 Hz, 1H). MS (DCI/NH$_3$) m/z 463 (M+H)$^+$.

EXAMPLE 13

4-(6-(4-(2-Isopropyl-phenylsulfanyl)-3-trifluoromethyl-phenyl)-pyrimidin-4-yl)-morpholine 43 was synthesized according to the following procedure.

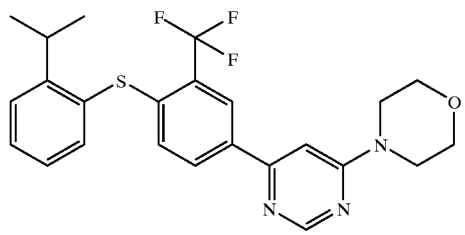

43

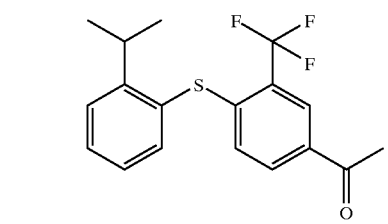

44

13A First, 1-(4-(2-isopropyl-phenylsulfanyl)-3-trifluoromethyl-phenyl)-ethanone 44 was prepared as follows. To a solution of 4-fluoro-3-trifluoromethyl-acetophenone (7.00 g, 34.0 mmol) in DMF (100 mL) was added 2-isopropylthiophenol (6.33 g, 37.4 mmol) followed by cesium carbonate (16.6 g, 51.0 mmol). The mixture was stirred at room temperature overnight. The reaction was partitioned between ethyl acetate (250 mL) and water (250 mL). The organic layer was separated, washed with brine (5×250 mL), dried over MgSO$_4$ and filtered. After evaporating the solvent, the crude material was loaded to a silica gel column, eluting with 5% ethyl acetate in hexane to give a colorless oil 44 (11.5 g, 100%). $^1$H-NMR (CDCl$_3$, 300 MHz) δ 1.17 (d, J=6.7 Hz, 6H), 2.57 (s, 3H), 3.46 (heptete, J=6.8 Hz, 1H), 6.80 (d, J=8.5 Hz, 1H), 7.24–7.29 (m, 1H), 7.45–7.50 (m, 2H), 7.53 (d, J=7.5 Hz, 1H), 7.79 (dd, J=2.0 Hz, 8.5 Hz, 1H), 8.21 (d, J=1.4 Hz, 1H). MS (DCI) m/z 339 (M+H)$^+$; 356 (M+NH$_4$)$^+$.

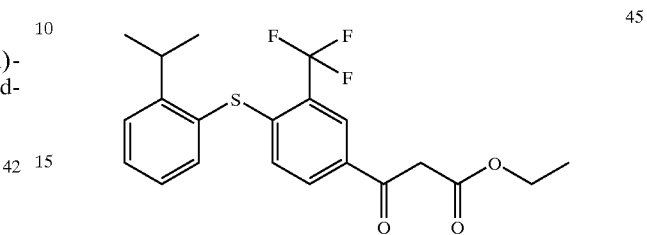

45

13B. Then, 3-(4-(2-isopropyl-phenylsulfanyl)-3-trifluoromethyl-phenyl)-3-oxo-propionic acid ethyl ester 45 was prepared as follows. To a solution of compound 44 (11.5 g, 34.0 mmol) in THF (150 mL) was added 60% sodium hydride in mineral oil (1.84 g, 40.8 mmol). The mixture was stirred at room temperature for 10 minutes. Diethyl carbonate (46.5 mL, 340 mmol) was added and the mixture was heated under reflux for 2 hours. 10% HCl aq. (100 mL) was added and the solution was extracted with ethyl acetate (200 mL). The organic layer was separated, washed with brine (5×250 mL), dried over MgSO$_4$ and filtered. The filtrate was concentrated on a rotor-vapor to give a brown oil 45 (10.6 g, 76%); MS (DCI) m/z 411 (M+H)$^+$; 428 (M+NH$_4$)$^+$.

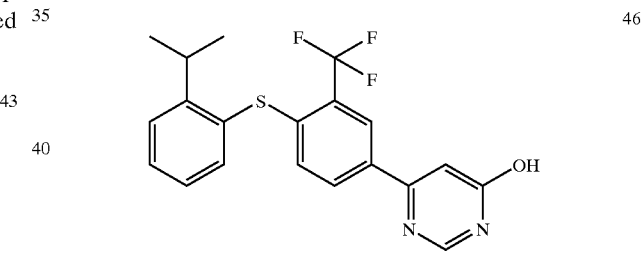

46

13C. Then, 6-(4-(2-isopropyl-phenylsulfanyl)-3-trifluoromethyl-phenyl)-pyrmidin-4-ol 46 was prepared as follows. The mixture of compound 45 (10.6 g, 25.8 mmol) and formamidine hydrochloride (10.4 g, 129 mmol) in 20% HOAc in DMF (50 mL) was heated at 120° C. for 3 days. MeOH (50 mL) was added and the resulting solution was purified on a preparative HPLC column, C$_8$ reverse-phase column, eluted with NH$_4$OAc-H$_2$O—CH$_3$CN. Evaporation of solvents gave a white solid 46 (1.40 g, 14%); MS (APCI) m/z 391 (M+H)$^+$.

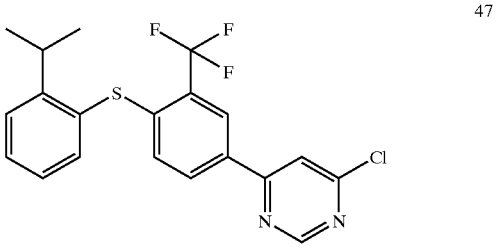

47

13D. Then, 4-chloro-6-(4-(2-isopropyl-phenylsulfanyl)-3-trifluoromethyl-phenyl)-pyrimidine 47 was prepared as follows. Compound 46 (1.40 g, 3.59 mmol) was treated with POCl₃ (30 mL) at 60° C. for an hour. The reaction mixture was concentrated on a rotor-vapor, and the residue was treated with crushed ice (10 g). Water (50 mL) was added. The aqueous solution was then extracted with ethyl acetate (2×50 mL). The combined organic layers were washed with brine (3×50 mL), dried over MgSO₄, filtered and concentrated. The crude product was purified by chromatography to give a brown oil 47 (0.74 g, 51%). ¹H-NMR (CDCl₃, 400 MHz) δ 1.19 (d, J=6.7 Hz, 6H), 3.50 (heptet, J=6.8 Hz, 1H), 6.89 (d, J=8.5 Hz, 1H), 7.24–7.28 (m, 1H), 7.46–7.50 (m, 2H), 7.54 (d, J=7.6 Hz, 1H), 7.68 (s, 1H), 7.93 (d, J=8.4 Hz, 1H), 8.38 (s, 1H), 9.00(s, 1H), MS (DCI) m/z 409, 411 (M+H)⁺.

13E. To a solution of compound 47 (0.015 g, 0.0367 mmol) in DMF (1.0 mL) was added morpholine followed by potassium carbonate (0.015 g, 0.109 mmol). The reaction mixture was heated at 80° C. for 16 hours. The solid was removed through filtration, and the filtrate was directly purified by preparative HPLC, to give a yellow solid, 43 (0.012 g, 72%). ¹H-NMR (CDCl₃, 400 MHz) δ 1.19 (d, J=6.8 Hz, 6H), 3.51 (heptet, J=6.8 Hz, 1H), 3.69 (t, J=4.9 Hz, 4H), 3.81 (t, J=4.9 Hz, 4H), 6.80 (s, 1H), 6.90 (d, J=8.5 Hz, 1H), 7.20–7.24 (m, 1H), 7.43 (s, 1H), 7.44 (s, 1H), 7.48 (d, J=7.6 Hz, 1H), 7.87 (d, J=8.2 Hz, 1H), 8.26 (s, 1H), 8.67(s, 1H). MS (APCI) m/z 460 (M+H)⁺.

EXAMPLE 14

1-(6-(4-(2-Isopropyl-phenylsulfanyl)-3-trifluoromethyl-phenyl)-pyrimidin-4-yl)-piperidin-4-ol 48 was synthesized according to the following procedure.

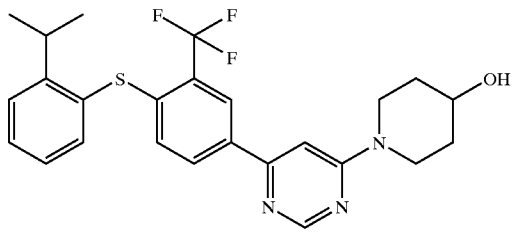

48

The title compound 48 was prepared according to the procedures of Example 13E, substituting morpholine with 4-hydroxypiperidine. A yellow solid was obtained (0.012 g, 71%). ¹H-NMR (DMSO, 400 MHz) δ 1.14 (d, J=7.2 Hz, 6H), 1.48–1.52(m, 2H), 1.87–1.90 (m, 2H), 3.10–3.70 (m, 4H, overlapping with the solvent H₂O peak), 4.38–4 42 (m, 2H), 6.90 (d, J=8.4 Hz, 1H), 7.32–7.35 (m, 2H), 7.47–7.55 (m, 3H), 8.25 (d, J=8.2 Hz, 1H), 8.50 (s, 1H), 8.55 (s, 1H); MS (APCI) m/z 474 (M+H)⁺.

EXAMPLE 15

4-(6-(4-(2-Isopropyl-phenylsulfanyl)-3-trifluoromethyl-phenyl)-pyrimidin-4-yl)-2,6-dimethyl-morpholine 49 was synthesized according to the following procedure.

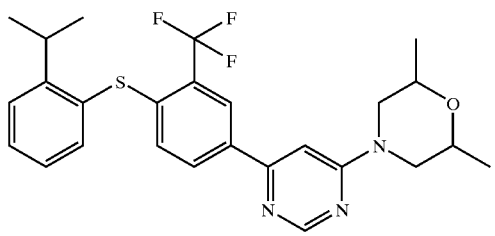

49

The title compound was prepared according to the procedures of Example 13E, substituting morpholine with 2,6-dimethylmorpholine. A yellow solid 49 was obtained (0.013 g, 73%). ¹H-NMR (CDCl₃, 400 MHz) δ 1.18 (d, J=7.2 Hz, 6H), 1.28 (d, J=6.4 Hz, 6H), 2.65 (dd, J=2.1, 10.6 Hz, 2H), 3.52 (heptet, J=6.8 Hz, 1H), 3.65–3.70 (m, 2H), 4.24 (br d, J=11.5 Hz, 2H), 6.78 (s, 1H), 6.90 (d, J=8.4 Hz, 1H), 7.20–7.24 (m, 1H), 7.43 (s, 1H), 7.44 (s, 1H), 7.48 (d, J=7.7 Hz, 1H), 7.87 (d, J=8.5 Hz, 1h), 8.27 (s, 1H), 8.66(s, 1H). MS (APCI) m/z 488 (M+H)⁺.

EXAMPLE 16

1-(6-(4-(2-Isopropyl-phenylsulfanyl)-3-trifluoromethyl-phenyl)-pyrimidin-4-yl)-piperidine-3-carboxylic acid amide 50 was synthesized according to the following procedure.

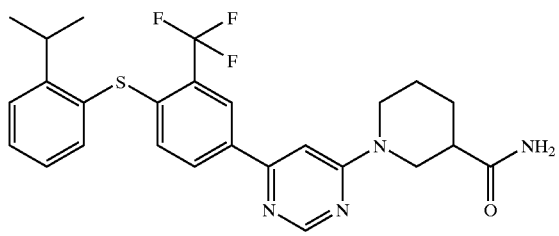

50

The title compound was prepared according to the procedures of Example 13E, substituting morpholine with nipecotamide. A yellow solid 50 was obtained (0.014 g, 74%). ¹H-NMR (CDCl₃, 400 MHz) δ 1.19 (d, J=6.8 Hz, 6H), 1.54–1.66 (m 1H), 1.76–1.84 (m, 1H), 1.96–2.12 (m, 2H), 2.46–2.53 (m, 1H), 3.27–3.35 (m, 1H), 3.51 (heptaplet, J=6.6 Hz, 1H), 3.70–3.76 (m, 1H), 3.94–4.01 (br, 1H), 4.20–4.26 (m, 1H), 5.44 (s, br, 1H), 6.10 (s, br, 1H), 6.84 (s, 1H), 6,90 (d, J=8.1 Hz, 1H), 7.20–7.25 (m, 1H), 7.43 (s, 1H), 7.44 (s, 1H), 7.48 (d, J=7.6 Hz, 1H), 7.85 (d, J=8.0 Hz, 1H), 8.28 (s, 1H), MS (APCI) m/z 501 (M+H)⁺.

EXAMPLE 17

1-(6-(4-(2-Isopropyl-phenylsulfanyl)-3-trifluoromethyl-phenyl)-pyrimidin-4-yl)-piperidine-4-carboxylic acid amide 51 was synthesized according to the following procedure.

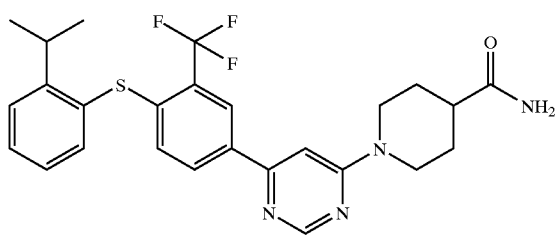

51

The title compound was prepared according to the procedures of Example 13E, substituting morpholine with isonipecotamide. A yellow solid 51 was obtained (0.013 g, 69%). ¹H-NMR (CDCl₃, 400 MHz) δ 1.19 (d, J=6.8 Hz, 6H), 1.71–1.82 (m, 2H), 1.97–2.04 (m, 2H), 2.44–2.53 (m, 1H), 3.07 (t, J=12.5 Hz, 2H), 3.52 (heptet, J=6.8 Hz, 1H), 4.49 (d, J=13.6 Hz, 2H), 5.49 (br s, 1H), 5.59 (br s, 1H), 6.83 (s, 1H), 6.90 (d, J=8.5 Hz, 1H), 7.20–7.24 (m, 1H), 7.43 (s, 1H), 7.44 (s, 1H), 7.48 (d, J=7.6 Hz, 1H), 7.86 (d, J=8.5 Hz, 1H), 8.26 (s, 1H), 8.65 (s, 1H); MS (APCI) m/z 501 (M+H)⁺.

EXAMPLE 18

N-Ethyl-N-1-(6-(4-(2-isopropyl-phenylsulfanyl)-3-trifluoromethyl-phenyl)-pyrimidin-4-yl)-pyrrolidin-3-yl)-acetamide 52 was synthesized according to the following procedure.

52

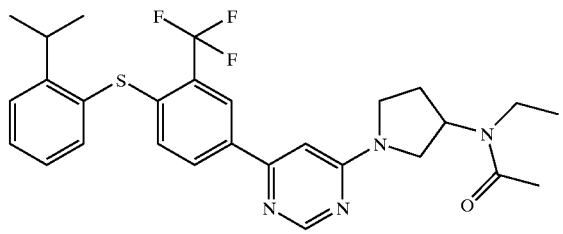

The title compound was prepared according to the procedures of Example 13E, substituting morpholine with 3-N-acetyl-N-ethylamino)pyrrolidine. A yellow solid 52 was obtained (0.014 g, 72%). MS (APCI) m/z 529 (M+H)⁺.

EXAMPLE 19

1-(6-(4-(2-Isopropyl-phenylsulfanyl)-3-trifluoromethyl-phenyl)-pyrimidin-4-yl)-piperidine-3-carboxylic acid ethyl ester 53 was synthesized according to the following procedure.

53

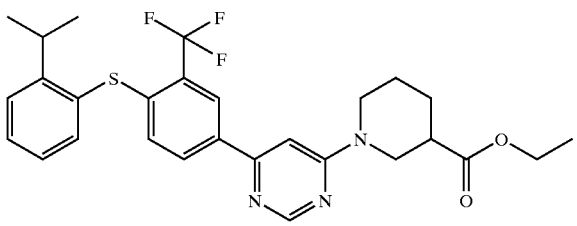

The title compound was prepared according to the procedures of Example 13E, substituting morpholine with ethyl nipecotate. A yellow solid 53 was obtained (0.011 g, 56%). ¹H-NMR (CDCl₃, 400 MHz) δ 1.19 (d, J=6.7 Hz, 6H), 1.25 (t, J=7.2 Hz, 3H), 1.57–1.60 (m, 1H), 1.79–1.88 (m, 2H), 2.10–2.14 (m, 1H), 2.54–2.59 (m, 1H), 3.21–3.38 (m, 1H), 3.35–3.40 (m, 1H), 3.52 (heptet, J=6.8 Hz, 1H), 4.11–4.18 (m, 1H), 4.16 (q, J=7.2, 2H), 4.38–4.44 (m, 1H), 6.86 (s, 1H), 6.90 (d, J=8.5 Hz, 1H), 7.20–7.25 (m, 1H), 7.43 (s, 1H), 7.44 (s, 1H), 7.48 (d, J=7.6 Hz, 1H), 7.86 (d, J=8.4 Hz, 1H), 8.28 (s, 1H), 8.65 (s, 1H); MS (APCI) m/z 530 (M+H)⁺.

EXAMPLE 20

1-(6-(4-(2-Isopropyl-phenylsulfanyl)-3-trifluoromethyl-phenyl)-pyrimidin-4-yl)-piperidine-4-carboxylic acid ethyl ester 54 was synthesized according to the following procedure.

54

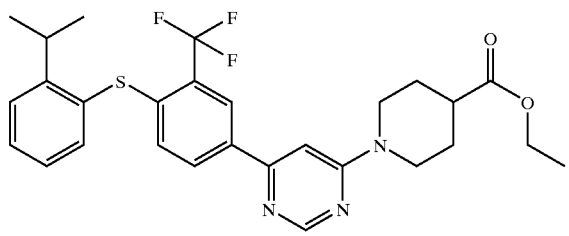

The title compound was prepared according to the procedures of Example 13E, substituting morpholine with ethyl isonipecotate. A yellow solid 54 was obtained (0.012 g, 61%) ¹H-NMR (CDCl₃, 400 MHz) δ 1.19 (d, J=6.8 Hz, 6H), 1.27 (t, J=7.2 Hz, 3H), 1.71–1.81 (m, 2H), 2.00–2.04 (m, 2H), 2.58–2.65 (m, 1H), 3.11–3.18 (m, 2H), 3.52 (heptet, J=6.8 Hz, 1H), 4.16 (q, J=7.2 Hz, 2H), 4.32–4.38 (m, 2H), 6.82 (s, 1H), 6.90 (d, J=8.5 Hz, 1H), 7.20–7.24 (m, 1H), 7.43 (s, 1H), 7.44 (s, 1H), 7.48 (d, J=7.6 Hz, 1H), 7.86 (d, J=8.5 Hz, 1H), 8.26 (s, 1H), 8.65 (s, 1H); MS (APCI) m/z 530 (M+H)⁺.

EXAMPLE 21

4-(6-(4-(2-Isopropyl-phenylsulfanyl)-3-trifluoromethyl-phenyl)-pyrimidin-4-yl)-piperidine-1-carboxylic acid ethyl ester 55 was synthesized according to the following procedure.

55

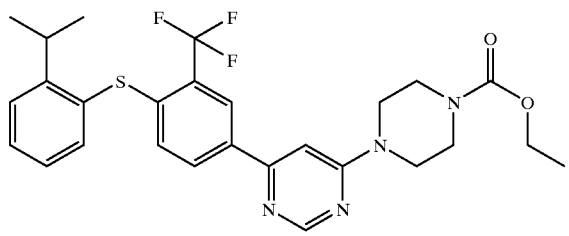

The title compound was prepared according to the procedures of Example 13E, substituting morpholine with ethyl piperazine-1-carboxylate. A yellow solid 55 was obtained (0.019 g, 96%). ¹H-NMR (CDCl₃, 400 MHz) δ 1.19 (d, J=6.8 Hz, 6H), 1.29 (t, J=7.2 Hz, 3H), 3.51 (heptaplet, J=6.8 Hz, 1H), 3.59–3.62 (m, 4H), 3.71–3.75 (m, 4H), 4.19 (q, J=7.2 Hz, 2H), 6.81 (s, 1H), 6.90 (d, J=8.5 Hz, 1H), 7.19–7.25 (m, 1H), 7.42–7.45 (m, 2H), 7.46–7.50 (m, 1H), 7.86 (d, J=8.5 Hz, 1H), 8.26 (s, 1H), 8.67 (s, 1H); MS (APCI) m/z 531 (M+H)⁺.

EXAMPLE 22

4-(6-(4-(2-Isopropyl-phenylsulfanyl)-3-trifluoromethyl-phenyl)-pyrimidin-4-yl)-piperazin-1-yl)-acetic acid ethyl ester 56 was synthesized according to the following procedure.

56

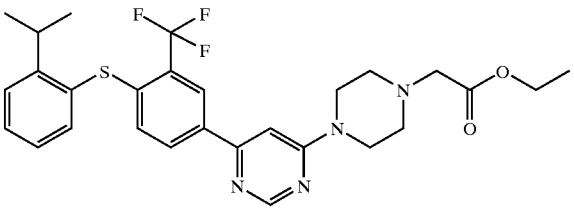

The title compound was prepared according to the procedures of Example 13E, substituting morpholine with 1-(ethoxycarbonylmethyl)piperazine A yellow solid 56 was obtained (0.007 g, 37%). $^1$H-NMR (CDCl$_3$, 400 MHz) δ 1.18 (d, J=6.8 Hz, 6H), 1.29 (t, J=7.2 Hz, 3H), 2.70 (br, 4H), 3.28 (s, 2H), 3.51 (heptet, J=6.8 Hz, 1H), 3.78 (br m, 4H), 4.21 (q, J=7.2 Hz, 2H), 6.80 (s, 1H), 6.90 (d, J=8.5 Hz, 1H), 7.21–7.27 (m, 1H), 7.42–7.45 (m, 2H), 7.46–7.50 (m, 1H), 7.86 (d, J=8.5 Hz, 1H), 8.26 (s, 1H), 8.65 (s, 1H); MS (APCI) m/z 545 (M+H)$^+$.

EXAMPLE 23

(3-Imidazol-1-yl-propyl)-(6-(4-(2-isopropyl-phenylsulfanyl)-3-trifluoromethyl-phenyl)-pyrimidin-4-yl)-amine 57 was synthesized according to the following procedure.

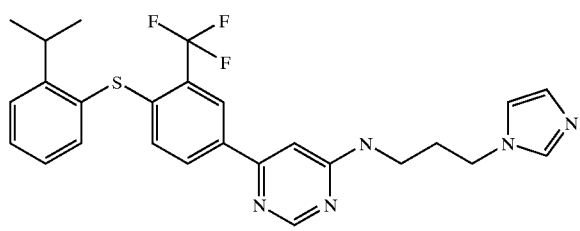

57

The title compound was prepared according to the procedures of Example 13E, substituting morplioline with 1-(3-aminopropyl)imidazole. A yellow solid 57 was obtained (0.010 g, 54%). $^1$H-NMR (CDCl$_3$, 400 MHz) δ 1.18 (d, J=6.8 Hz, 6H), 2.16 (p, J=6.8 Hz, 2H), 3.36–3.41 (m, 2H), 3.51 (heptet, J=6.8 Hz, 1H), 4.10 (t, J=6.7, 2H), 6.58 (s, 1H), 6.89 (d, J=8.5 Hz, 1H), 6.95 (s, 1H), 7.09 (s, 1H), 7.21–7.25 (m, 1H), 7.43–7.46 (m, 2H), 7.49 (d, J=7.6 Hz, 1H), 7.60 (s, 1H), 7.83 (d, J=8.4 Hz, 1H), 8.26 (s, 1H), 8.58 (s, 1H). MS (APCI) m/z 498 (M+H)$^+$.

EXAMPLE 24

1-(6-(4-(2-Isopropyl-phenylsulfanyl)-3-trifluoromethyl-phenyl)-pyrimidin-4-yl)-piperidine-4-carboxylic acid 58 was synthesized according to the following procedure.

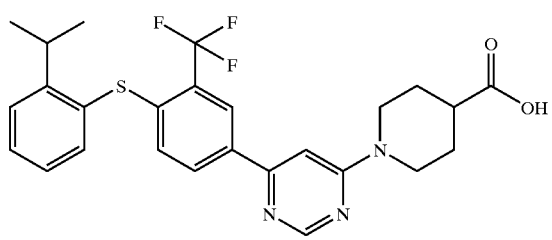

58

The title compound was prepared according to the procedures of Example 13E, substituting morpholine with isonipecotic acid. A yellow solid 58 was obtained (0.004 g, 24%). $^1$H-NMR (DMSO, 400 MHz) δ 1.14 (d, J=7.2 Hz, 6H), 1.48–1.52 (m, 2H), 1.87–1.90 (m, 2H), 3.10–3.70 (m, 4H, overlapping with the solvent H$_2$O peak), 4.38–4.42 (m, 2H), 6.90 (d, J=8.4 Hz, 1H), 7.31–7.35 (m, 2H), 7.47–7.55 (m, 3H), 8.25 (d, J=8.2 Hz, 1H), 8.50 (s, 1H), 8.55 (s, 1H). MS (APCI) m/z 502 (M+H)$^+$.

EXAMPLE 25

1-(6-(4-(2-Isopropyl-phenylsulfanyl)-3-trifluoromethyl-phenyl)-pyrimidin-4-yl)-piperidine-3-carboxylic acid 59 was synthesized according to the following procedure.

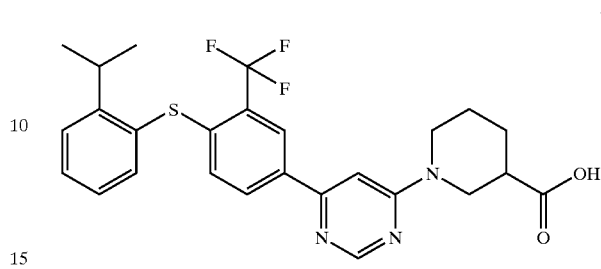

59

The title compound was prepared according to the procedures of Example 13E, substituting morpholine with nipecotic acid. A yellow solid 59 was obtained (0.011 g, 57%). $^1$H-NMR (DMSO, 400 MHz) δ 1.14 (d, J=7.2 Hz, 6H), 1.43–1.46 (m, 2H), 1.63–1.72 (m, 2H), 1.97–1.20 (m, 1H), 2.36–2.41 (m, 1H), 3.10–3.70 (m, 2H, overlapping with the solvent H$_2$O peak), 4.24–4.28 (m, 1H), 4.46–4.52 (m, 1H), 6.90 (d, J=8.4 Hz, 1H), 7.30–7.33 (m, 1H), 7.38 (s, 1H), 7.46 (d, J=8.0 Hz, 1H), 7.48–7.57 (m, 2H), 8.25 (d, J=8.2 Hz, 1H), 8.50 (s, 1H), 8.55 (s, 1H); MS (APCI) m/z 502 (M+H)$^+$.

EXAMPLE 26

4-(4-(2-Isopropyl-phenylsulfanyl)-3-trifluoromethyl-phenyl)-pyrmidin-4-yl)-piperidine-3-carboxylic acid 60 was synthesized according to the following procedure.

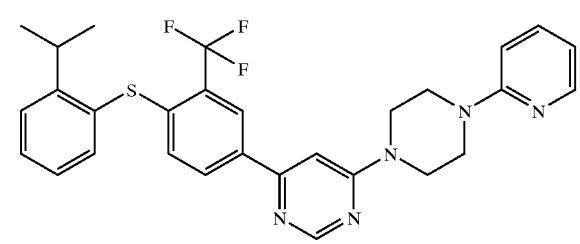

60

The title compound was prepared according to the procedures of Example 13E, substituting morpholine with 1-(2-pyridyl)piperazine. A yellow solid 60 was obtained (0.013 g, 65%). $^1$H-NMR (CDCl$_3$, 400 MHz) δ 1.19 (d, J=6.8 Hz, 6H), 3.52 (heptet, J=6.8 Hz, 1H), 3.71 (t, J=5.3 Hz, 4H), 3.87 (t, J=5.3 Hz, 4H), 6.66–6.69 (m, 2H), 6.84 (s, 1H), 6.90 (d, J=8.5 Hz, 1H), 7.21–7.25 (m, 1H), 7.43 (s, 1H), 7.44 (s, 1H), 7.47–7.55 (m, 2H), 7.88 (d, J=8.5 Hz, 1H), 8.21–8.23 (m, 1H), 8.29 (s, 1H), 8.68 (s, 1H); MS (APCI) m/z 536 (M+H)$^+$.

EXAMPLE 27

1-(6-(4-(2-Isopropyl-phenylsulfanyl)-3-trifluoromethyl-phenyl)-pyrimidin-4-yl)-piperidine-3-carboxylic acid diethylamide 61 was synthesized according to the following procedure.

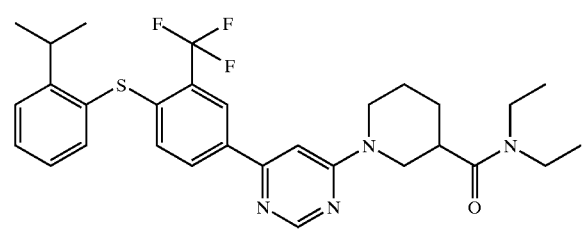

61

The title compound was prepared according to the procedures of Example 13E, substituting morpholine with N,N-diethyl nipecotamide. A yellow solid 61 was obtained (0.014 g, 69%). ¹H-NMR (CDCl₃, 400 MHz) δ 1.13 (t, J=7.2 Hz, 3H), 1.19 (d, J=6.8 Hz, 6H), 1.21 (t, J=7.2 Hz, 3H), 1.52–1.59 (m, 1H), 1.82–1.99 (m, 3H), 2.61–2.69 (m, 1H), 3.30 (m, 1H), 3.15 (m, 1H), 3.32–3.45 (m, 4H), 3.52 (heptet, J=6.8 Hz, 1H), 4.35–4.41 (br, 1H), 4.58–4.65 (br, 1H), 6.82 (s, 1H), 6.90 (d, J=8.5 Hz, 1H), 7.21–7.24 (m, 1H), 7.43 (s, 1H), 7.44 (s, 1H), 7.48 (d, J=7.7 Hz, 1H), 7.85 (d, J=8.5 Hz, 1H), 8.26 (s, 1H), 8.63 (s, 1H); MS (DCI) m/z 557 (M+H)⁺.

EXAMPLE 28

4-(4-(2-Isopropyl-phenylsulfanyl)-3-trifluoromethyl-phenyl)-6-(3-(2H-tetrazol-5-yl)-piperidin-1-yl)-pyrimidine 62 was synthesized according to the following procedure.

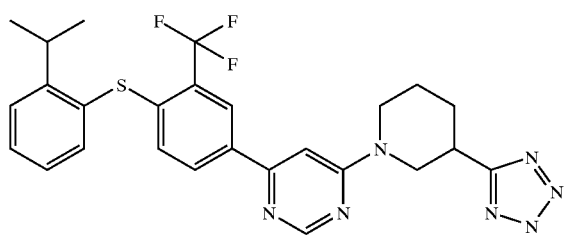

62

The title compound was prepared according to the procedures of Example 13E, substituting morpholine with 3-(5'-tetrazolyl)-piperidine. A yellow solid 62 was obtained (0.004 g, 21%). ¹H-NMR (CDCl₃, 400 MHz) δ 1.18 (d, J=6.8 Hz, 6H), 1.45–1.56 (m, 1H), 1.68–1.77 (m, 1H), 2.17–2.27 (m, 1H), 2.51–2.59 (m, 1H), 3.42–3.51 (m, 2H), 3.50 (heptaplet, J=6.8 Hz, 1H), 3.66–3.73 (m, 1H), 3.92–3.98 (m, 1H), 4.51–457 (m, 1H), 6.86–6.91 (m, 2H), 7.21–7.28 (m, 1H), 7.43–7.51 (m, 3H), 7.85 (d, J=8.5 Hz, 1H), 8.23 (s, 1H), 8.78 (s, 1H); MS (APCI) m/z 526 (M+H)⁺.

EXAMPLE 29

4-(4-(2-Isopropyl-phenylsulfanyl)-3-trifluoromethyl-phenyl)-6-(4-(2H-tetrazol-5-yl)-piperidin-1-yl)-pyrimidine 63 was synthesized according to the following procedure.

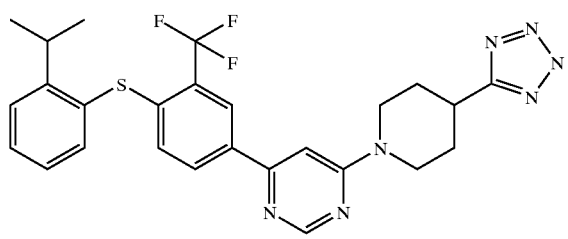

63

The title compound was prepared according to the procedures of Example 13E, substituting morpholine with 4-(5'-tetrazolyl)-piperidine. A yellow solid 63 was obtained (0.008 g, 40%). ¹H-NMR (CDCl₃, 400 MHz) δ 1.17 (d, J=6.8 Hz, 6H), 1.78–182 (m, 2H), 2.10–2.15 (m, 2H), 3.11–3.19 (m, 2H), 3.29–3.37 (m, 1H), 3.49 (heptet, J=6.8 Hz, 1H), 4.43–4.49 (br, 2H), 6.82 (s, 1H), 6.88 (d, J=8.5 Hz, 1H), 7.18–7.25 (m, 1H), 7.42 (s, 1H), 7.43 (s, 1H), 7.46 (d, J=7.7 Hz, 1H), 7.81 (d, J=8.5 Hz, 1H), 8.21 (s, 1H), 8.61 (s, 1H); MS (APCI) m/z 526 (M+H)⁺.

EXAMPLE 30

(1-(6-(4-(2-Isopropyl-phenylsulfanyl)-3-trifluoromethyl-phenyl)-pyrimidin-4-yl)-piperidin-3-yl)-methanol 64 was synthesized according to the following procedure.

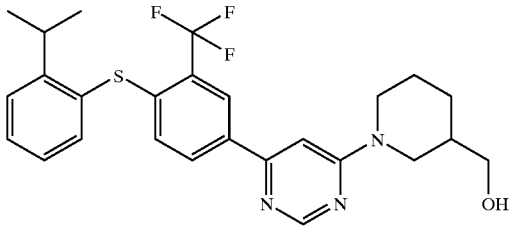

64

The title compound was prepared according to the procedures of Example 13E, substituting morpholine with 3-hydroxymethyl piperidine. A yellow solid 64 was obtained (0.012 g, 67%). ¹H-NMR (CDCl₃, 400 MHz) δ 1.17 (d, J=6.8 Hz, 6H), 1.78–182 (m, 2H), 2.10–2.15 (m, 2H), 3.11–3.19 (m, 2H), 3.29–3.37 (m, 1H), 3.49 (heptaplet, J=6.8 Hz, 1H), 4.43–4.49 (br, 2H), 6.82 (s, 1H), 6.88 (d, J=8.5 Hz, 1H), 7.18–7.25 (m, 1H), 7.42 (s, 1H), 7.43 (s, 1H), 7.46 (d, J=7.7 Hz, 1H), 7.81 (d, J=8.5 Hz, 1H), 8.21 (s, 1H), 8.61 (s, 1H); MS (APCI) m/z 488 (M+H)⁺.

EXAMPLE 31

2-(1-(6-(4-(2-Isopropyl-phenylsulfanyl)-3-trifluoromethyl-phenyl)-pyrimidin-4-yl)-piperidin-4-yl)-ethanol 65 was synthesized according to the following procedure.

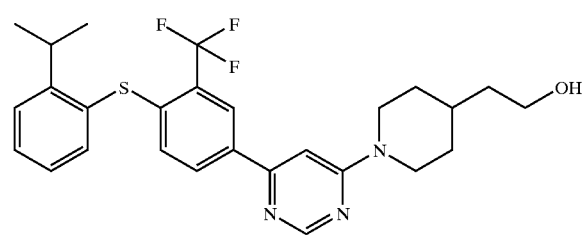

65

The title compound was prepared according to the procedures of Example 13E, substituting morpholine with 4-(2'-hydroxyethyl)-piperidine. A yellow solid 65 was obtained (0.013 g, 68%). ¹H-NMR (DMSO, 400 MHz) δ 1.06–1.09 (m, 1H), 1.14 (d, J=7.2 Hz, 6H), 1.37–1.38 (m, 2H), 1.73–1.75 (m, 3H), 2.90 (t, J=10.8 Hz, 1H), 3.74–3.48 (m, 3H), 4.35–4.37 (m, 1H), 4.51–4.54 (m, 1H), 6.90 (d, J=8.4 Hz, 1H), 7.30–7.33 (2H), 7.46 (d, J=8.0 Hz, 1H), 7.48–7.57 (m, 2H), 8.25 (d, J=8.2 Hz, 1H), 8.50 (s, 1H), 8.53 (s, 1H); MS (APCI) m/z 502 (M+H)⁺.

EXAMPLE 32

N-(1-(6-(4-(2-Isopropyl-phenylsulfanyl)-3-trifluoromethyl-phenyl)-pyrimidin-4-yl)-pyrrolidin-3-yl)-acetamide 66 was synthesized according to the following procedure.

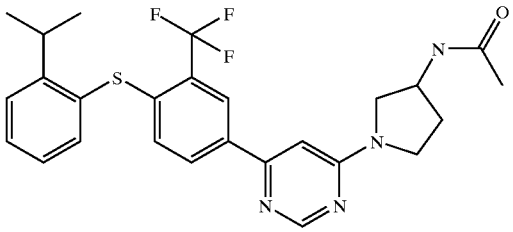

66

The title compound was prepared according to the procedures of Example 13E, substituting morpholine with 3-acetamidopyrrolidine. A yellow solid 66 was obtained (0.012 g, 67%). ¹H-NMR (CDCl₃, 400 MHz) δ 1.19 (d, J=6.8 Hz, 6H), 2.00 (s, 3H), 2.02–2.08 (m, 1H), 2.30–2.39 (m, 1H), 3.38–3.52 (br, 1H), 3.51 (heptet, J=6.8 Hz, 1H), 3.60–3.70 (br, 1H), 3.78–3.87 (m, 1H), 4.58–4.66 (m, 1H), 5.62–5.68 (m, 1H), 6.59 (s, 1H), 6.90 (d, J=8.5 Hz, 1H), 7.20–7.28 (m, 1H), 7.43 (s, 1H), 7.44 (s, 1H), 7.48 (d, J=7.7 Hz, 1H), 7.88 (d, J=8.5 Hz, 1H), 8.28 (s, 1H), 8.65 (s, 1H); MS (APCI) m/z 501 (M+H)⁺.

EXAMPLE 33

4-(4-(2-Isopropyl-phenylsulfanyl)-3-trifluoromethyl-phenyl)-6-(2-methoxymethyl-pyrrolidin-1-yl)-pyrimidine 67 was synthesized according to the following procedure.

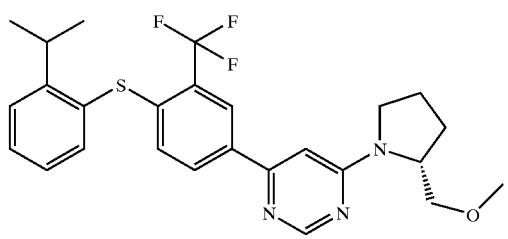

The title compound was prepared according to the procedures of Example 13E, substituting morpholine with (R)-(+)-2-(methoxymethyl)pyrrolidine. A yellow solid 67 was obtained (0.011 g, 63%). ¹H-NMR (CDCl₃, 400 MHz) δ 1.19 (d, J=6.8 Hz, 6H), 2.01–2.15 (m, 4H), 3.36 (s, 3H), 3.38–3.62 (m, 4H), 3.52 (heptet, J=6.8 Hz, 1H), 4.36 (s, br, 1H), 6.68 (s, 1H), 6.91 (d, J=8.5 Hz, 1H), 7.18–7.26 (m, 1H), 7.43 (s, 1H), 7.44 (s, 1H), 7.47 (d, J=7.7 Hz, 1H), 7.86 (d, J=8.5 Hz, 1H), 8.28 (s, 1H), 8.64 (s, 1H); MS (APCI) m/z 488 (M+H)⁺.

EXAMPLE 34

1-(6-(4-(2-Isopropyl-phenylsulfanyl)-3-trifluoromethyl-phenyl)-pyrimidin-4-yl)-pyrrolidin-3-ol 68 was synthesized according to the following procedure.

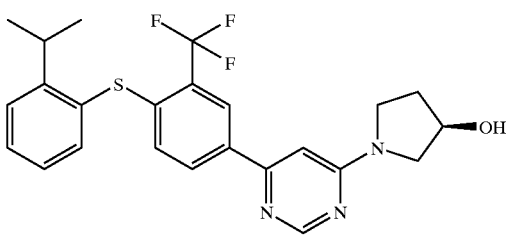

The title compound was prepared according to the procedures of Example 13E, substituting morpholine with (R)-(+)-3-pyrrolidinol. A yellow solid 68 was obtained (0.012 g, 73%). ¹H-NMR (DMSO, 400 MHz) δ 1.14 (d, J=7.2 Hz, 6H), 1.80–2.10 (m, 2H), 3.43 (heptet, 7.2 Hz, 1H), 3.54 (br s, 3H), 4.22 (m, 1H), 5.10 (m, 1H), 6.92 (d, J=8.4 Hz, 1H), 7.01 (s, 1H), 7.31–7.35 (m, 1H), 7.47 (d, J=8.0 Hz, 1H), 7.48–7.57 (m, 2H), 8.25 (d, J=8.2 Hz, 1H), 8.50 (s, 1H), 8.52 (s, 1H); MS (APCI) m/z 460 (M+H)⁺.

EXAMPLE 35

1-(6-(4-(2-Isopropyl-phenylsulfanyl)-3-trifluoromethyl-phenyl)-pyrimidin-4-yl)-pyrrolidin-3-yl)-carbamic acid tert-butyl ester 69 was synthesized according to the following procedure.

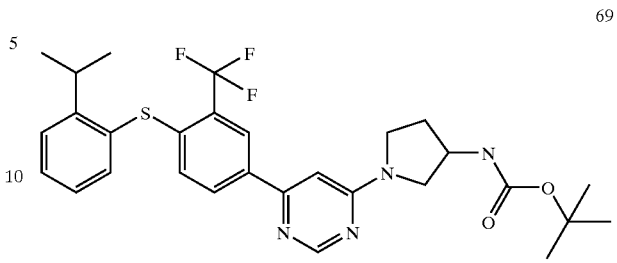

The title compound was prepared according to the procedures of Example 13E, substituting morpholine with 3-(tert-butoxycarbonylamino)pyrrolidine. A yellow solid 69 was obtained (0.015 g, 72%). ¹H-NMR (DMSO, 400 MHz) δ 1.14 (d, J=7.2 Hz, 6H), 1.39 (s, 9H), 1.90 (br s, 1H), 2.18 (br s, 1H), 3.43 (heptet, 7.2 Hz, 1H), 3.54 (br s, 4H), 4.18 (m, 1H), 6.91 (d, J=8.4 Hz, 1H), 7.02 (s, 1H), 7.22 (br s, 1H), 7.31–7.35 (m, 1H), 7.47 (d, J=8.0 Hz, 1H), 7.48–7.57 (m, 2H), 8.25 (d, J=8.2 Hz, 1H), 8.50 (s, 1H), 8.52 (s, 1H); MS (APCI) m/z 459 (M+H)⁺.

EXAMPLE 36

Isopropyl-(6-(4-(2-isopropyl-phenylsulfanyl)-3-trifluoromethyl-phenyl)-pyrimidin-4-yl)-methyl amine 70 was synthesized according to the following procedure.

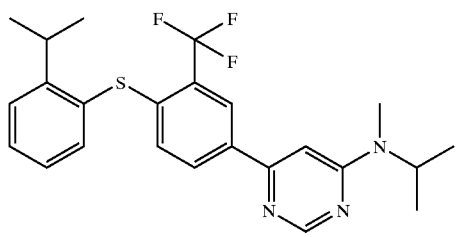

The title compound was prepared according to the procedures of Example 13E, substituting morpholine with N-methylisopropylamine. A yellow solid 70 was obtained (0.009 g, 57%). ¹H-NMR (CDCl₃, 400 MHz) δ 1.19 (d, J=6.8 Hz, 6H), 1.22 (d, J=6.8 Hz, 6H), 2.93 (s, 3H), 3.52 (heptaplet, J=6.8 Hz, 1H), 6.69 (s, 1H), 6.91 (d, J=8.5 Hz, 1H), 7.19–7.24 (m, 1H), 7.42 (s, 1H), 7.43 (s, 1H), 7.48 (d, J=7.7 Hz, 1H), 7.86 (d, J=8.5 Hz, 1H), 8.27 (s, 1H), 8.64 (s, 1H). MS (APCI) m/z 446. (M+H)⁺.

EXAMPLE 37

Ethyl-(6-(4-(2-isopropyl-phenylsulfanyl)-3-trifluoromethyl-phenyl)-pyrimidin-4-yl)-methyl-amine 71 was synthesized according to the following procedure.

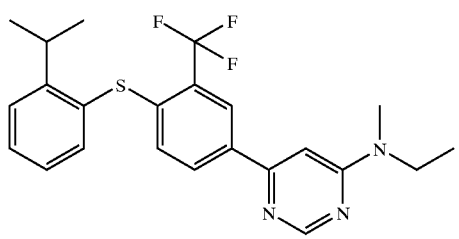

The title compound was prepared according to the procedures of Example 13E, substituting morpholine with N-ethylmethylamine. A yellow solid 71 was obtained (0.009 g, 56%). $^1$H-NMR (CDCl$_3$, 400 MHz) δ 1.19 (d, J=6.8 Hz, 6H) 1.21 (t, J=7.2 Hz, 3H), 3.11 (s, 3H), 3.52 (heptet, J=6.8 Hz, 1H), 3.64 (q, J=7.2 Hz, 2H), 6.68 (s, 1H), 6.91 (d, J=8.5 Hz, 1H), 7.19–7.24 (m, 1H), 7.42 (s, 1H), 7.43 (s, 1H), 7.47 (d, J=7.7 Hz, 1H), 7.86 (d, J=8.5 Hz, 1H), 8.28 (s, 1H), 8.64 (s, 1H). MS (APCI) m/z 432 (M+H)$^+$.

EXAMPLE 38

1-(4-(4-(2-Isopropyl-phenylsulfanyl)-3-trifluoromethyl-phenyl)-pyridin-2-yl)-pyrrolidin-3-ol 72 was synthesized according to the following procedure.

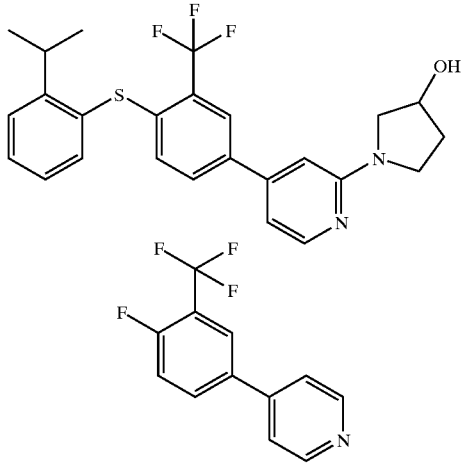

38A. First, 4-(4-fluoro-3-trifluoromethyl-phenyl)-pyridine 73 was prepared as follows. To a suspension of pyridine-4-boronic acid (2.59 g, 21.1 mmol) in 1-propanol (60 mL) was added 5-bromo-2-fluorobenzotrifluoride (5.12 g, 21.1 mmol) and triphenylphosphine (0.160 g, 0.610 mmol), followed by sodium carbonate in water (2.0 M, 12 mL). The mixture was purged with nitrogen gas for 10 minutes. To it was added palladium(II) acetate (0.044 g, 0.196 mmol) and it was then heated under reflux for 4 hours. The reaction mixture was partitioned between ethyl acetate (200 mL) and water (200 mL). The organic layer was separated, washed with brine (3×200 mL), dried over MgSO$_4$, then filtered. After evaporating the solvent, the crude material was loaded to a silica gel column, eluting with 60% ethyl acetate in hexane to give a white solid 73 (2.73 g, 54%). $^1$H-NMR (CDCl$_3$, 400 MHz) δ 7.34–7.42 (m, 1H), 7.61–7.65 (m, 2H), 7.80–7.93 (m, 2H), 8.73–8.84 (m, 2H); MS (DCI) m/z 242, 243 (M+H)$^+$.

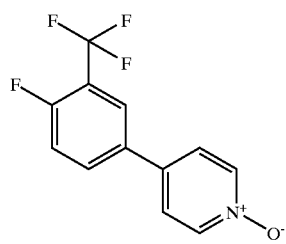

38B. Then, 4-(4-fluoro-3-trifluoromethyl-phenyl)-pyridine-1-oxide 74 was prepared as follows. To a solution of compound 73 (2.49 g, 10.3 mmol) in dichloromethane (10 mL) was added methyltrioxorhenium(VII) (0.128 g, 0.515 mmol), followed by hydrogen peroxide in water (30%, 5.15 mL). The reaction mixture was stirred at room temperature for 16 hours. Manganese (IV) oxide (0.050 g) was added. The mixture was stirred for another 30 minutes. The organic layer was separated. The aqueous layer was extracted with more dichloromethane (2×10 mL). The combined organic phase was washed with brine (3×30 mL), dried over MgSO$_4$ and filtered. After evaporating the solvent, the crude material was loaded to a silica gel column, eluting with 10% methanol in ethyl acetate to give a white solid 74 (2.51 g, 94%). $^1$H-NMR (CDCl$_3$, 400 MHz) δ 7.35 (t, J=9.3 Hz, 1H), 7.49 (d, J=7.2 Hz, 2H), 7.74–7.82 (m, 2H), 8.30 (d, J=7.1 Hz, 2H); MS (DCI) m/z 258, 259 (M+H)$^+$.

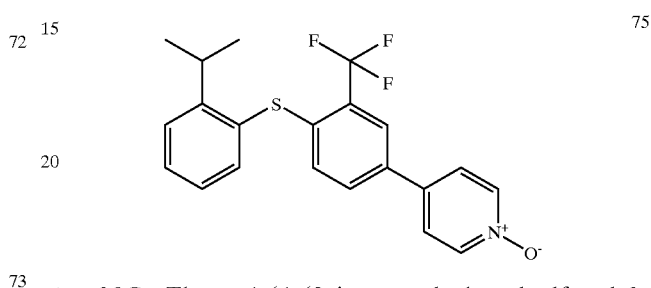

38C. Then, 4-(4-(2-isopropyl-phenylsulfanyl-3-trifluoromethyl-phenyl)-pyridine-1-oxide 75 was prepared as follows. A solution of compound 74 (2.51 g, 9.76 mmol) in dimethylacetamide (100 mL) was purged with nitrogen gas for 10 minutes. To it was added cesium carbonate (3.80 g, 11.7 mmol), followed by 2-isopropylthiophenol (4.90 mL, 29.3 mmol). The reaction was heated at 100° C. for 16 hours. The mixture was partitioned between ethyl acetate (200 mL) and water (200 mL). The organic layer was separated, washed with brine (5×200 mL), dried over MgSO$_4$ and then filtered. After evaporating the solvent, the crude material was loaded to a silica gel column, eluting with 10% methanol in ethyl acetate to give a white solid 75 (3.19 g 84%). $^1$H-NMR (CDCl$_3$, 400 MHz) δ 1.19 (d, J=6.8 Hz, 6H), 3.51 (heptaplet, J=6.8 Hz, 1H), 6.90 (d, J=8.1 Hz, 1H), 7.22–7.28 (m, 1H), 7.44–7.51 (m, 6H), 7.84 (d, J=2.1 Hz, 1H), 8.24 (d, J=7.4 Hz, 2H); MS (DCI) m/z 390 (M+H)$^+$.

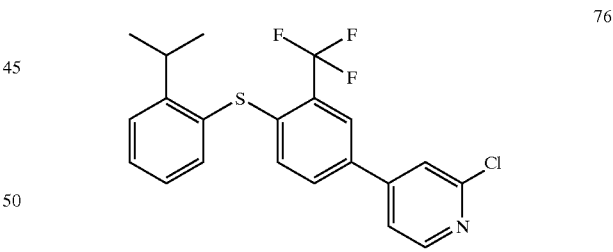

38D. Then, 2-chloro-4-(4-(2-isopropyl-phenylsulfanyl-3-trifluoromethyl-phenyl)-pyridine 76 was prepared as follows. Compound 75 (3.19 g, 8.19 mmol) was treated with POCl$_3$ (50 mL) at 100° C. for 10 hours. The reaction mixture was concentrated on a rotovap, and the residue was treated with crushed ice (20 g). Water (100 mL) was added, the aqueous solution was then extracted with ethyl acetate (2×100 mL). The combined organic layers were washed with brine (3×100 mL), dried over MgSO$_4$, filtered and concentrated. The crude product was purified by chromatography to give the title compound 76 as a brown oil (2.74 g, 82%). $^1$H-NMR (CDCl$_3$, 400 MHz) δ 1.19 (d, J=6.8 Hz, 6H), 3.51 (heptet, J=6.8 Hz, 1H), 6.91 (d, J=8.5 Hz, 1H), 7.25–7.28 (m, 1H), 7.37 (dd, J=1.7 Hz, 5.1 Hz, 1H), 7.45–7.52 (m, 5H), 7.87 (d, J=2.0 Hz, 1H), 8.43 (d, J=5.4 Hz, 1H). MS (DCI) m/z 408, 409, 410 (M+H)+.

38E. To a solution of compound 76 (0.024 g, 0.0588 mmol) in DMSO (0.50 mL) was added 3-hydroxylpyrrolidine (0.0256 g, 0.294 mmol). The reaction mixture was heated at 140° C. for 16 hours. It was then cooled down to room temperature. Methanol was added to the reaction mixture and then purified by preparative HPLC to give a yellow solid 72 (0.0256 g, 95%). 1H-NMR (CDCl3, 400 MHz) δ 1.20 (d, J=6.8 Hz, 6H), 2.14–2.22 (m, 1H), 2.25–2.32 (m, 1H), 2.65 (s, 1H), 3.50 (heptet, J=6.8 Hz, 1H), 3.75–3.83 (m, 2H), 3.86–3.94 (m, 2H), 4.73 (s, 1H), 6.78 (s, 1H), 6.91 (d, J=8.0 Hz, 2H), 7.25–7.29 (m, 1H), 7.45–7.52 (m, 4H), 7.85 (d, J=1.5 Hz, 1H), 8.10 (d, J=7.0 Hz, 1H); MS (APCI) m/z 459 (M+H)+.

EXAMPLE 39

(1-(4-(4-(2-Isopropyl-phenylsulfanyl)-3-trifluoromethyl-phenyl)-pyrdin-2-yl)-pyrrolidin-2-yl)-methanol 77 was synthesized according to the following procedure.

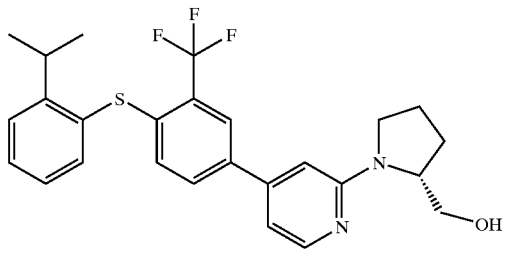

77

The title compound was prepared according to the procedures of Example 38E, substituting 3-hydroxypyrrolidine with (R)-2-(hydroxymethyl)pyrrolidine. A yellow solid 77 was obtained (0.0216 g, 78%). 1H-NMR (CDCl3, 400 MHz) δ 1.20 (d, J=6.8 Hz, 6H), 2.06–2.11 (m, 2H), 2.15–2.21 (m, 2H), 3.47–3.53 (m, 2H), 3.64–3.69 (m, 1H), 3.71–3.76 (m, 2H), 4.63 (s, 1H), 6.79 (s, 1H), 6.89–6.93 (m, 2H), 7.25–7.29 (m, 1H), 7.46–7.54 (m, 4H), 7.85 (d, J=1.8 Hz, 1H), 8.10 (d, J=6.9 Hz, 1H); MS (APCI) m/z 473 (M+H)+.

EXAMPLE 40

4'-(4-(2-Isopropyl-phenylsulfanyl)-3-trifluoromethyl-phenyl)-3,4,5,6-tetrahydro-2H-(1,2')bipyridiny-4-ol 78 was synthesized according to the following procedure.

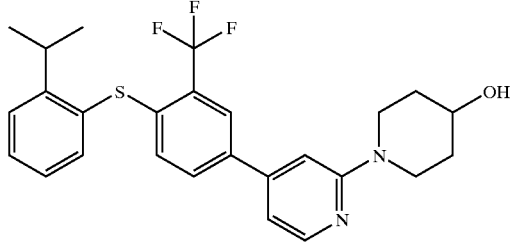

78

The title compound was prepared according to the procedures of Example 38E, substituting 3-hydroxypyrrolidine with 4-hydroxypiperidine. A yellow solid 78 was obtained (0.0255 g, 92%). 1H-NMR-(CDCl3, 400 MHz) δ 1.20 (d, J=6.8 Hz, 6H), 1.77–1.85 (m, 2H), 2.02–2.09 (m, 2H), 3.49 (heptet, J=6.8 Hz, 1H), 3.68–3.74 (m, 2H), 3.99–4.06 (m, 2H), 4.12–4.16 (m, 1H), 6.90 (d, J=8.0 Hz, 1H), 6.93 (d, J=6.6 Hz, 1H), 6.98 (s, 1H), 7.25–7.29 (m, 1H), 7.46–7.54 (m, 4H), 7.85 (s, 1H), 8.19 (d, J=6.6 Hz, 1H); MS (APCI) m/z 473 (M+H)+.

EXAMPLE 41

4-(4-(4-(2-Isopropyl-phenylsulfanyl)-3-trifluoromethyl-phenyl)-pyridin-2-yl)-piperazine-1-carbaldehyde 79 was synthesized according to the following procedure.

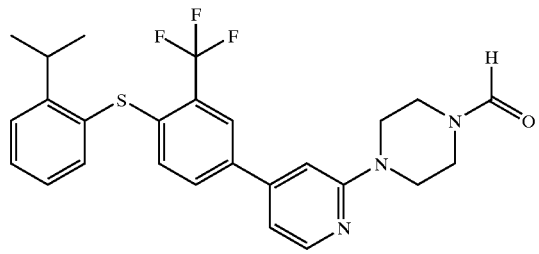

79

The title compound was prepared according to the procedures of Example 38E, substituting 3-hydroxypyrrolidine with 1-formylpiperazine. A yellow solid 79 was obtained (0.0073 g, 26%). 1H-NMR (CDCl3, 400 MHz) δ 1.19 (d, J=6.8 Hz, 6H), 3.50 (heptet, J=6.8 Hz, 1H), 3.62–3.66 (m, 2H), 3.69–3.73 (m, 2H), 3.75–3.78 (m, 2H), 3.89–3.93 (m, 2H), 6.92 (d, J=8.5 Hz, 1H), 6.95 (s, 1H), 7.03 (d, J=6.2 Hz, 1H), 7.25–7.29 (m, 1H), 7.46–7.54 (m, 4H), 7.85 (d, J=1.8 Hz, 1H), 8.16 (s, 1H), 8.29 (d, J=6.3 Hz, 1H); MS (APCI) m/z 486 (M+H)+.

EXAMPLE 42

1-(4-(4-(2-Isopropyl-phenylsulfanyl)-3-trifluoromethyl-phenyl)-pyridin-2-yl)-pyrrolidine-2-carboxylic acid 80 was synthesized according to the following procedure.

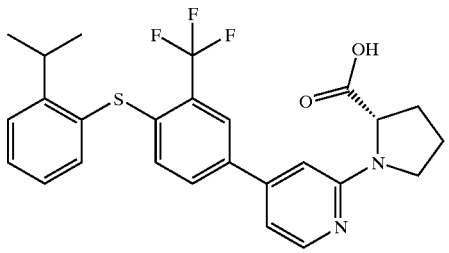

80

The title compound was prepared according to the procedures of Example 38E, substituting 3-hydroxypyrrolidine with (D)-proline. A yellow solid 80 was obtained (0.0232 g, 81%). 1H NMR (CDCl3, 400 MHz) δ 1.19 (d,J=6.8 Hz, 6H), 2.13–2.34 (m, 4H), 2.47–2.53 (br, 1H), 3.50 (heptet, J=6.8 Hz, 1H), 3.61 (br, 1H), 3.85 (br, 1H), 4.95 (br, 1H), 6.81 (s, 1H), 6.88–6.94 (m, 2H), 7.25–7.29 (m, 1H), 7.46–7.54 (m, 4H), 7.84 (s, 1H), 8.03 (d, J=6.6 Hz, 1H). MS (APCI) m/z 487 (M+H)+.

EXAMPLE 43

(4'-(4-(2-Isopropyl-phenylsulfanyl)-3-trifluoromethyl-phenyl)-3,4,5,6-tetrahydro-2H-(1,2')bipyridinyl-4-yl)-methanol 81 was synthesized according to the following procedure.

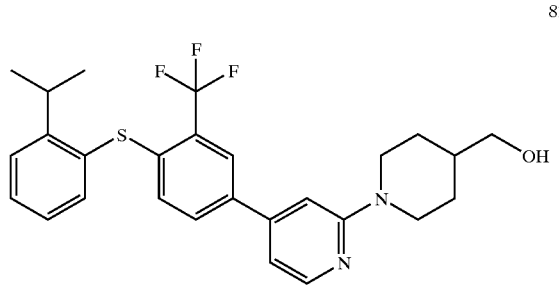

The title compound was prepared according to the procedures of Example 38E, substituting 3-hydroxypyrrolidine with 4-hydroxymethylpiperidine. A yellow solid 81 was obtained (0.0252 g, 88%). $^1$H-NMR (CDCl$_3$, 400 MHz) δ 1.19 (d, J=6.8 Hz, 6H), 1.41–1.50 (m, 2H), 1.86–1.94 (m, 1H), 1.99 (d, J=13.6 Hz, 2H), 3.27 (t, J=11.7 Hz, 2H), 3.50 (heptet, J=6.8 Hz, 1H), 3.57 (d, J=5.8 Hz, 2H), 4.36 (d, J=13.2 Hz, 2H), 6.85–6.94 (m, 2H), 6.97 (s, 1H), 7.25–7.29 (m, 1H), 7.46–7.54 (m, 4H), 7.84 (s, 1H), 8.22 (d, J=6.6 Hz, 1H); MS (APCI) m/z 487 (M+H)$^+$.

EXAMPLE 44

N-(1-(4-(4-(2-Isopropyl-phenylsulfanyl)-3-trifluoromethyl-phenyl)-pyridin-2-yl)-pyrrolidin-3-yl)-acetamide 82 was synthesized according to the following procedure.

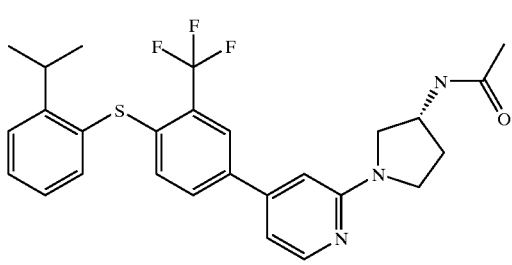

The title compound was prepared according to the procedures of Example 38E, substituting 3-hydroxypyrrolidine with (3R)-(+)-3-acetamidopyrrolidine. A yellow solid 82 was obtained (0.0243 g, 83%). $^1$H-NMR (CDCl$_3$, 400 MHz) δ 1.19 (d, J=6.8 Hz, 6H), 1.97 (s, 3H), 2.22–2.28 (m, 1H), 2.31–2.37 (m, 1H), 3.50 (heptet, J=6.8 Hz, 1H), 3.72–3.80 (m, 2H), 3.81–3.86 (m, 1H), 3.91–3.99 (m, 1H), 4.61–4.66 (m, 1H), 6.78 (s, 1H), 6.90 (d, J=8.4 Hz, 1H), 6.93 (d, J=5.9 Hz, 1H), 7.25–7.29 (m, 1H), 7.46–7.54 (m, 4H), 7.86 (d, J=1.5 Hz, 1H), 8.06 (d, J=6.6 Hz, 1H); MS (APCI) m/z 500 (M+H)$^+$.

EXAMPLE 45

N-(1-(4-(4-(2-Isopropyl-phenylsulfanyl)-3-trifluoromethyl-phenyl)-pyridin-2-yl)-pyrrolidin-3-yl)-acetamide 83 was synthesized according to the following procedure.

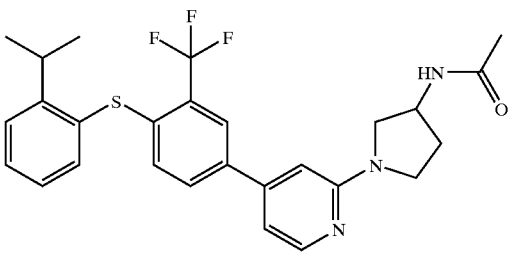

The title compound was prepared according to the procedures of Example 38E, substituting 3-hydroxypyrrolidine with 3-acetamidopyrrolidine. A yellow solid 83 was obtained (0.019 g, 65%). $^1$H-NMR (CDCl$_3$, 400 MHz) δ 1.19 (d, J=6.8 Hz, 6H), 1.99 (s, 3H), 2.22–2.29 (m, 1H), 2.33–2.40 (m, 1H), 3.49 (heptet, J=6.8 Hz, 1H), 3.73–3.81 (m, 2H), 3.82–3.87 (m, 1H), 3.96–4.04 (m, 1H), 4.62–4.67 (m, 1H), 6.78 (s, 1H), 6.90 (d, J=8.4 Hz, 1H), 6.94 (d, J=6.6 Hz, 1H), 7.26–7.29 (m, 1H), 7.46–7.54 (m, 4H), 7.85 (s, 1H), 8.03 (d, J=6.6 Hz, 1H); MS (APCI) m/z 500 (M+H)$^+$.

EXAMPLE 46

1-(4-(4-(2-Isopropyl-phenylsulfanyl)-3-trifluoromethyl-phenyl)-pyridin-2-yl)-piperazin-1-yl)-ethanone 84 was synthesized according to the following procedure.

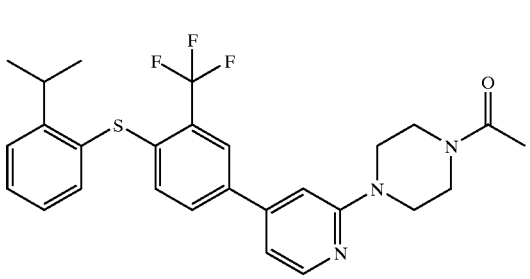

The title compound was prepared according to the procedures of Example 38E, substituting 3-hydroxypyrrolidine with 1-acetylpiperazine. A yellow solid 84 was obtained (0.0033 g, 11%). $^1$H-NMR (CDCl$_3$, 400 MHz) δ 1.19 (d, J=6.8 Hz, 6H), 2.17 (s, 3H), 3.50 (heptet, J=6.8 Hz, 1H), 3.68–3.72 (m, 2H), 3.73–3.77 (m, 2H), 3.83–3.89 (m, 2H), 3.96–4.00 (m, 2H), 6.91 (d, J=8.4 Hz, 1H), 6.94 (s, 1H), 7.02 (d, J=5.5 Hz, 1H), 7.25–7.29 (m, 1H), 7.46–7.54 (m, 4H), 7.86 (d, J=1.4 Hz, 1H), 8.28 (d, J=6.3 Hz, 1H); MS (APCI) m/z 500 (M+H)$^+$.

EXAMPLE 47

4'-(4-(2-Isopropyl-phenylsulfanyl)-3-trifluoromethyl-phenyl)-3,4,5,6-tetrahydro-2H-(1,2')bipyridinyl-4-carboxylic acid amide 85 was synthesized according to the following procedure.

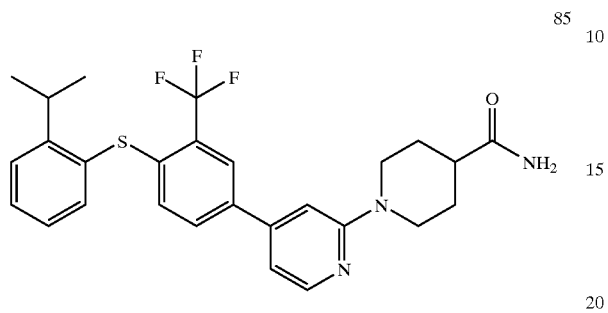

85

The title compound was prepared according to the procedures of Example 38E, substituting 3-hydroxypyrrolidine with isonipecotamide. A yellow solid 85 was obtained (0.0194 g, 66%). $^1$H-NMR (CDCl$_3$, 400 MHz) δ 1.19 (d, J=6.8 Hz, 6H), 1.89–1.99 (m, 2H), 2.07–2.13 (m, 2H), 2.58–2.65 (m, 1H), 3.41 (t, J=11.4 Hz, 2H), 3.50 (heptet, J=6.8 Hz, 1H), 4.28 (d, J=13.2 Hz, 2H), 5.65 (s, 1H), 6.06 (s, 1H), 6.90 (d, J=8.4 Hz, 1H), 6.95 (d, J 5.8 Hz, 1H), 6.99 (s, 1H), 7.25–7.29 (m, 1H), 7.44–7.52 (m, 4H), 7.85 (s, 1H), 8.18 (d, J=6.6 Hz, 1H). MS (APCI) m/z 500 (M+H)$^+$.

EXAMPLE 48

4'-(4-(2-Isopropyl-phenylsulfanyl)-3-trifluoromethyl-phenyl)-3,4,5,6-tetrahydro-2H-(1,2')bipyridinyl-4-carboxylic acid 86 was synthesized according to the following procedure.

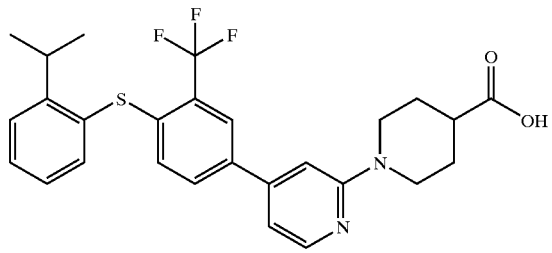

86

The title compound was prepared according to the procedures of Example 38E, substituting 3-hydroxypyrrolidine with isonipecotic acid. A yellow solid 86 was obtained (0.0112 g, 38%). $^1$H-NMR (CDCl$_3$, 400 MHz) δ 1.19 (d, J=6.8 Hz, 6H), 1.90–1.99 (m, 2H), 2.09–2.16 (m, 2H), 2.70–2.77 (m, 1H), 3.43–3.53 (m, 3H), 4.11–4.17 (m, 2H), 6.90 (d, J=8.4 Hz, 1H), 6.95 (d, J=6.6 Hz, 1H), 6.99 (s, 1H), 7.25–7.29 (m, 1H), 7.46–7.54 (m, 4H), 7.84 (d, J=1.1 Hz, 1H), 8.17 (d, J=6.6 Hz, 1H); MS (APCI) m/z 501 (M+H)$^+$.

EXAMPLE 49

4'-(4-(2-Isopropyl-phenylsulfanyl)-3-trifluoromethyl-phenyl)-3,4,5,6-tetrahydro-2H-(1,2')bipyridinyl-3-carboxylic acid 87 was synthesized according to the following procedure.

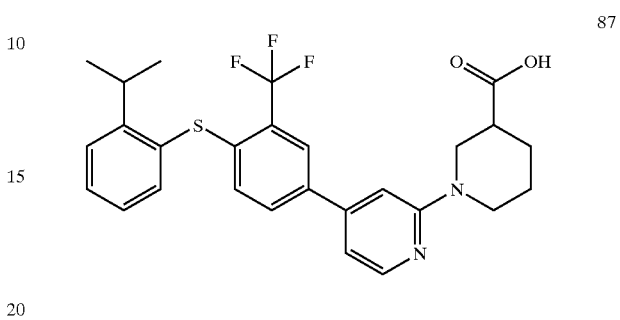

87

The title compound was prepared according to the procedures of Example 38E, substituting 3-hydroxypyrrolidine with nipecotic acid. A yellow solid 87 was obtained (0.0229 g, 78%). $^1$H-NMR (CDCl$_3$, 400 MHz) δ 1.19 (d, J=6.8 Hz, 6H), 1.65–1.74 (m, 1H), 1.89–1.96 (m, 1H), 2.05–2.10 (m, 2H), 2.83–2.89 (m, 1H), 3.49 (heptet, J=6.8 Hz, 1H), 3.56–3.63 (m, 1H), 3.78–3.88 (m, 2H), 4.13–4.18 (m, 1H), 6.91 (d, J=8.4 Hz, 1H), 6.95 (d, J=6.3 Hz, 1H), 7.07 (s, 1H), 7.25–7.29 (m, 1H), 7.46–7.54 (m, 4H), 7.85 (s, 1H), 8.26 (d, J=6.6 Hz, 1H); MS (APCI) m/z 501 (M+H)$^+$.

EXAMPLE 50

2-(4'-(4-(2-Isopropyl-phenylsulfanyl)-3-trifluoromethyl-phenyl)-3,4,5,6-tetrahydro-2H-(1,2')bipyridinyl-4-yl-ethanol 88 was synthesized according to the following procedure.

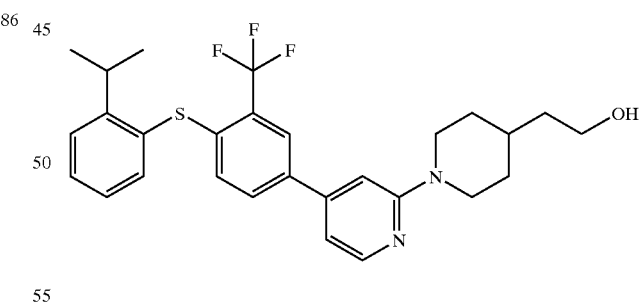

88

The title compound was prepared according to the procedures of Example 38E, substituting 3-hydroxypyrrolidine with 4-(1'-hydroxyethyl)piperidine. A yellow solid 88 was obtained (0.0245 g, 83%). $^1$H-NMR (CDCl$_3$, 400 MHz) δ 1.19 (d, J=6.8 Hz, 6H), 1.34–1.44 (m, 1H), 1.57 (q, J=6.2 Hz, 2H), 1.84–1.93 (m, 1H), 1.97 (s, 1H), 2.00 (s, 1H), 3.25 (t, J=12.5 Hz, 2H), 3.50 (heptet, J=6.8 Hz, 1H), 3.74 (t, J=6.4 Hz, 2H), 4.32 (s, 1H), 4.34 (s, 1H), 6.88–6.95 (m, 2H), 6.96 (s, 1H), 7.25–7.29 (m, 1H), 7.46–7.54 (m, 4H), 7.84 (s, 1H), 8.22 (d, J=6.6 Hz, 1H); MS (APCI) m/z 501 (M+H)$^+$.

EXAMPLE 51

4-Hydroxy-1-(4-(4-(2-isopropyl-phenylsulfanyl)-3-trifluoromethyl-phenyl)-pyridin-2-yl)-pyrrolidine-2-carboxylic acid 89 was synthesized according to the following procedure.

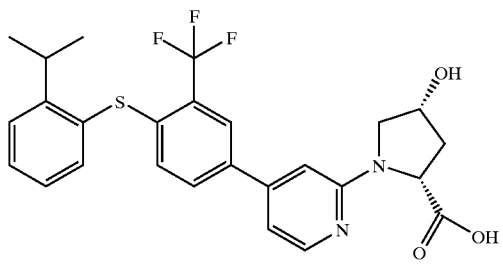

The title compound was prepared according to the procedures of Example 38E, substituting 3-hydroxypyrrolidine with cis-4-hydroxy-D-proline. A yellow solid 89 was obtained (0.0187 g, 63%). $^1$H-NMR (CDCl$_3$, 400 MHz) δ 1.19 (d, J=6.8 Hz, 6H), 2.30–2.37 (m, 1H), 2.61 (d, J=13.5 Hz, 1H), 3.49 (heptet, J=6.8 Hz, 1H), 3.69–3.77 (m, 1H), 3.86–3.94 (m, 1H), 4.65 (s, 1H), 4.76–4.84 (m, 1H), 6.88 (d, J=8.4 Hz, 2H), 6.96 (d, J=6.3 Hz 1H), 7.25–7.29 (m, 1H), 7.46–7.54 (m, 4H), 7.83 (s, 1H), 7.99 (d, J=6.6 Hz, 1H); MS (APCI) m/z 503 (M+H)$^+$.

EXAMPLE 52

4-Hydroxy-1-(4-(4-(2-isopropyl-phenylsulfanyl)-3-trifluoromethyl-phenyl)-pyridin-2-yl)-pyrrolidine-2-carboxylic acid 90 was synthesized according to the following procedure.

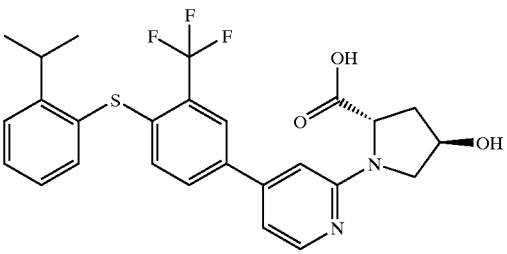

The title compound was prepared according to the procedures of Example 38E, substituting 3-hydroxypyrrolidine with trans-4-hydroxy-L-proline. A yellow solid 90 was obtained (0.0288 g, 97%). $^1$H-NMR (CDCl$_3$, 400 MHz) δ 1.19 (d, J=6.8 Hz, 6H), 2.44–2.50 (m, 1H), 2.65–2.67 (m, 1H), 3.49 (heptet, J=6.8 Hz, 1H), 3.68–3.74 (m, 1H), 3.87–3.93 (m, 1H), 4.65–4.70 (m, 1H), 4.92–4.98 (m, 1H), 6.82 (s, 1H), 6.89 (d, J=8.1 Hz, 1H),6.94 (d, J=1.7 Hz, 1H), 7.25–7.29 (m, 1H), 7.46–7.54 (m, 4H), 7.83 (s, 1H), 7.94–7.99 (br m, 1H). MS (APCI) m/z 503 (M+H)$^+$.

EXAMPLE 53

N-(1-(4-(4-(2-isopropyl-phenylsulfanyl)-3-trifluoromethyl-phenyl)-pyridin-2-yl)-pyrrolidine-3-yl)-N-methyl-acetamide 91 was synthesized according to the following procedure.

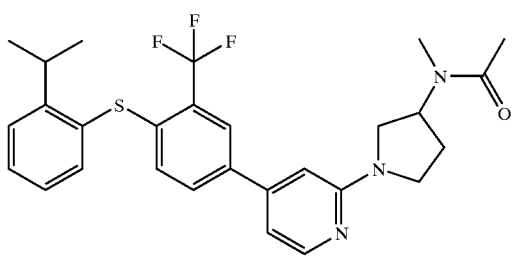

The title compound was prepared according to the procedures of Example 38E, substituting 3-hydroxypyrrolidine with 3-(N-acetyl-N-methylamino)pyrrolidine. A yellow solid 91 was obtained (0.0265 g, 88%). $^1$H-NMR (CDCl$_3$, 400 MHz) δ 1.19 (d, J=6.8 Hz, 6H), 2.15 (s, 3H), 2.24–2.39 (m, 2H), 3.01 (s, 3H), 3.49 (heptet, J=6.8 Hz, 1H), 3.63–3.78 (m, 2H), 3.91–4.06 (m, 2H), 5.18–5.26 (m, 1H), 6.76 (s, 1H), 6.90 (d, J=8.4 Hz, 1H), 6.97 (d, J=5.9 Hz, 1H), 7.25–7.29 (m, 1H), 7.46–7.54 (m, 4H), 7.86 (s, 1H), 8.18 (d, J=6.3 Hz, 1H); MS (APCI) m/z 514 (M+H)$^+$.

EXAMPLE 54

4-Hydroxy-4'-(4-(2-isopropyl-phenylsulfanyl)-3-trifluoromethyl-phenyl)-3,4,5,6-tetrahydro-2H-(1,2') bipyridinyl-3-carboxylic acid 92 was synthesized according to the following procedure.

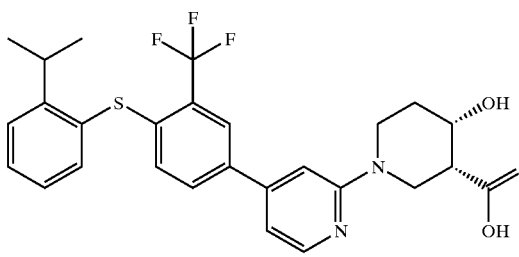

The title compound was prepared according to the procedures of Example 38E, substituting 3-hydroxypyrrolidine with (+/−)-cis-4-hydroxynipecotic acid. A yellow solid 92 was obtained (0.0087 g, 29%). $^1$H-NMR (CDCl$_3$, 400 MHz) δ 1.19 (d, J=6.8 Hz, 6H), 1.73–1.82 (m, 1H), 2.02–2.08 (m, 1H), 2.96–3.01 (m, 1H), 3.49 (heptet, J=6.8 Hz, 1H), 3.84 (d, J=6.6 Hz, 2H), 4.00 (t, J=12.6 Hz, 1H), 4.33 (d, J=12.4 Hz, 1H), 4.46 (s, 1H), 6.91 (d, J=8.4 Hz, 1H), 7.01 (d, J=6.2 Hz 1H), 7.08 (s, 1H), 7.25–7.29 (m, 1H), 7.46–7.54 (m, 4H), 7.86 (s, 1H), 8.41 (d, J=6.6 Hz, 1H); MS (APCI) m/z 517 (M+H)$^+$.

EXAMPLE 55

(3-(4-(4-(4-(2-Isopropyl-phenylsulfanyl)-3-trifluoromethyl-phenyl)-pyridin-2-yl)-piperazin-1-yl)-propyl)-dimethyl-amine 93 was synthesized according to the following procedure.

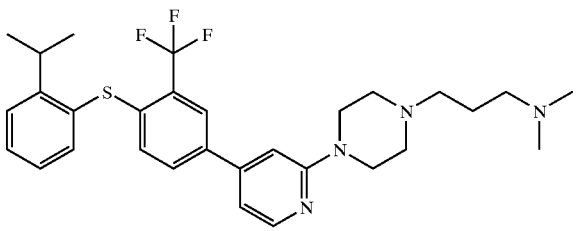

The title compound was prepared according to the procedures of Example 38E, substituting 3-hydroxypyrrolidine with 1-(3-dimethylaminopropyl)piperazine. A yellow solid 93 was obtained (0.027 g, 85%). $^1$H-NMR (CDCl$_3$, 400 MHz) δ 1.19 (d, J=6.8 Hz, 6H), 2.43–2.50(m, 6H), 2.86 (s, 6H), 3.22–3.30 (m, 4H), 3.36–3.40 (m, 2H), 3.51 (heptet, J=6.8 Hz, 1H), 4.08–4.12 (m, 2H), 6.83–6.94 (m, 2H), 7.01 (d, J=5.5 Hz, 1H), 7.25–7.29 (m, 1H), 7.46–7.54 (m, 4H), 7.86 (s, 1H), 8.23 (d, J=5.6 Hz, 1H); MS (APCI) m/z 543 (M+H)$^+$.

EXAMPLE 56

1-(4-(4-(2-Methoxy-phenylsulfanyl)-3-trifluoromethyl-phenyl)-pyridin-2-yl)-pyrrolidine-3-ol 94 was synthesized according to the following procedure.

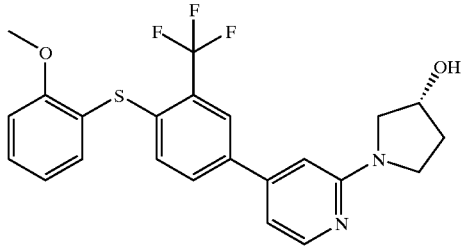

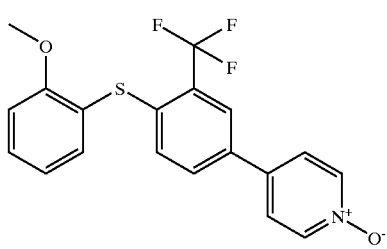

56A. First, 4-(4-(2-methoxy-phenylsulfanyl)-3-trifluoromethyl-phenyl)-pyridine 1-oxide 95 was prepared as follows. The title compound was prepared according to the procedures of Example 38C, substituting 2-isopropyl-thiophenol with 2-methoxythiophenol. A white solid 95 was obtained (1.02 g, 77%). $^1$H-NMR (DMSO, 400 MHz) δ 3.79 (s, 3H), 7.04 (t, J=1.1 Hz, 7.6 Hz, 1H), 7.08 (d, J=8.0 Hz, 1H), 7.19 (dd, J=0.8 Hz, 8.4 Hz, 1H), 7.33 (dd, J=0.9 Hz, 8.4 Hz, 1H), 7.49 (dt, J=1.7 Hz, 7.6 Hz, 1H), 7.84 (dt, J=2.1 Hz, 7.2 Hz, 2H), 7.91 (dd, J=2.1 Hz, 8.4 Hz, 1H), 8.10 (d, J=2.1 Hz, 1H), 8.26 (dt, J=2.0 Hz, 7.2 Hz, 2H). MS (APCI) m/z 378 (M+H)$^+$.

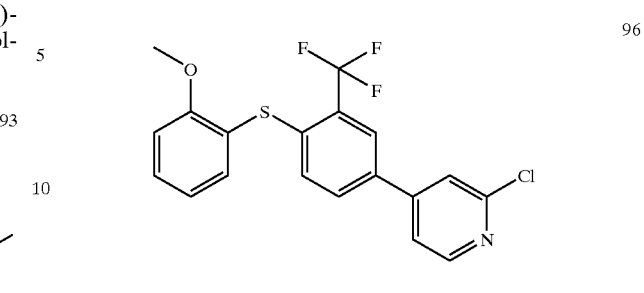

56B. Then 2-chloro-4-(4-(2-methoxy-phenylsulfanyl)-3-trifluoromethyl-phenyl)-pyridine 96 was prepared as follows. The title compound was prepared according to the procedures of Example 38D, substituting compound 75 with compound 95 (0.900 g, 2.38 mmol). A yellow oil 96 was obtained (0.70 g, 74%). $^1$H-NMR (CDCl$_3$, 400 MHz) δ 3.83 (s, 3H), 6.98–7.03 (m, 2H), 7.09 (d, J=8.2 Hz, 1H), 7.39(dd, J=1.7 Hz, 5.1 Hz, 1H), 7.41–7.46 (m, 2H), 7.49–7.53 (m, 2H), 7.87 (d, J=2.1 Hz, 1H), 8.43 (d, J=4.7 Hz, 1H); MS (APCI m/z 396) (M+H)$^+$.

56C. The title compound was prepared according to the procedures of Example 38E, substituting compound 76 with compound 96 (0.039 g, 0.0985 mmol) and 3-hydroxypyrrolidine with (R)-3-hydroxypyrrolidine. A yellow solid 94 was obtained (0.0385 g, 87%). $^1$H-NMR (CDCl$_3$, 400 MHz) δ 2.13–2.31 (m, 2H), 3.83 (s, 3H), 3.88–3.95 (m, 4H), 4.74 (m, 1H), 6.79 (s, 1H), 6.92 (d, J=6.6 Hz, 1H), 7.01–7.07 (m, 3H), 7.45–7.53 (m, 3H), 7.86 (s, 1H), 8.14 (d, J=7.0 Hz, 1H); MS (APCI) m/z 447 (M+H)$^+$.

EXAMPLE 57

1-(4-(4-(2-Methoxy-phenylsulfanyl)-3-trifluoromethyl-phenyl)-pyridin-2-yl)-pyrrolidin-2-yl)-methanol 97 was synthesized according to the following procedure.

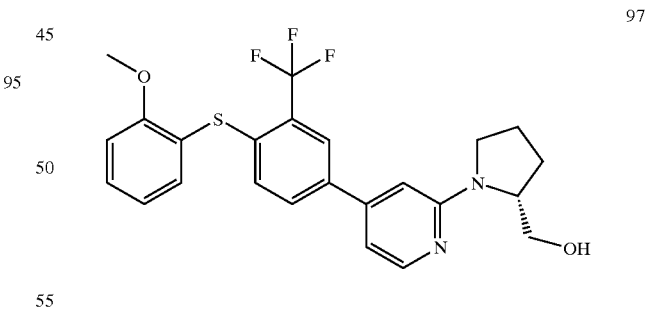

The title compound was prepared according to the procedures of Example 38E, substituting compound 76 with compound 96 (0.039 g, 0.0985 mmol) and 3-hydroxypyrrolidine with (R)-2-(hydroxymethyl)pyrrolidine. A yellow solid 97 was obtained (0.0233 g, 51%). $^1$H-NMR (CDCl$_3$, 400 MHz) δ 2.05–2.11 (m, 2H), 2.14–2.21 (m, 2H), 3.50 (q, J=9.1 Hz, 1H), 3.62–3.76 (m, 3H), 3.83 (s, 3H), 4.59–4.65 (m, 1H), 6.79 (s, 1H), 6.92 (d, J=6.3 Hz, 1H), 7.01–7.07 (m, 3H), 7.45–7.52 (m, 3H), 7.84 (s, 1H), 8.12 (d, J=6.6 Hz, 1H). MS (APCI) m/z 461 (M+H)$^+$.

EXAMPLE 58

4'-(4-(2-Methoxy-phenylsulfanyl)-3-trifluoromethyl-phenyl)-3,4,5,6-tetrahydro-2H-(1,2')bipyridinyl-4-ol 98 was synthesized according to the following procedure.

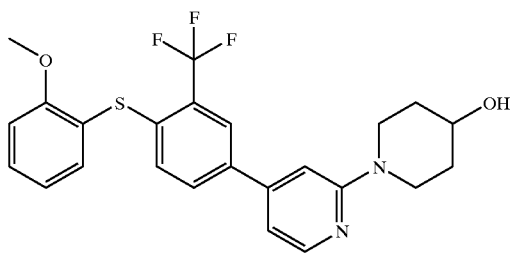

98

The title compound was prepared according to the procedures of Example 38E, substituting compound 76 with compound 96 (0.039 g, 0.0985 mmol) and 3-hydroxypyrrolidine with 4-hydroxypiperidine. A yellow solid 98 was obtained (0.0299 g, 66%). $^1$H-NMR (CDCl$_3$, 400 MHz) δ 1.76–1.84 (m, 2H), 2.02–2.10 (m, 2H), 3.69–3.76 (m, 2H), 3.83 (s, 3H), 4.01–4.07 (m, 2H), 4.12–4.17 (m, 1H), 6.95 (d, J=6.6 Hz, 1H), 6.99 (s, 1H), 7.01–7.07 (m, 3H), 7.46–7.52 (m, 3H), 7.85 (s, 1H), 8.23 (d, J=6.6 Hz, 1H), MS (APCI) m/z 461 (M+H)$^+$.

EXAMPLE 59

4-(4-(4-(2-Methoxy-phenylsulfanyl)-3-trifluoromethyl-phenyl)-pyridin-2-yl)-piperazine-1-carbaldehyde 99 was synthesized according to the following procedure.

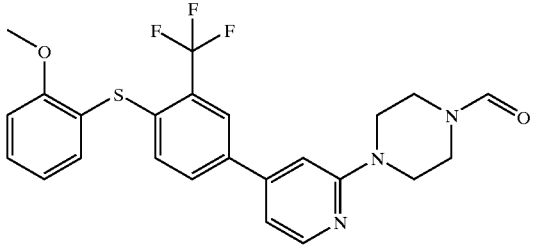

99

The title compound was prepared according to the procedures of Example 38E, substituting compound 76 with compound 96 (0.039 g, 0.0985 mmol) and 3-hydroxypyrrolidine with 1-formylpiperazine. A yellow solid 99 was obtained (0.0159 g, 34%). $^1$H-NMR (CDCl$_3$, 400 MHz) δ 3.62–3.65 (m, 2H), 3.68–3.72 (m, 2H), 3.75–3.78 (m, 2H), 3.83 (s, 3H), 3.86–3.89 (m, 2H), 6.95 (s, 1H), 7.02 (m, 3H), 7.08 (d, J=8.4 Hz, 1H), 7.46–7.52 (m, 3H), 7.86 (d, J=1.5 Hz, 1H), 8.16 (s, 1H), 8.30 (d, J=6.2 Hz, 1H), MS (APCI) m/z 474 (M+H)$^+$.

EXAMPLE 60

1-(4-(4-(2-Methoxy-phenylsulfanyl)-3-trifluoromethyl-phenyl)-pyridin-2-yl)-pyrrolidine-2-carboxylic acid 100 was synthesized according to the following procedure.

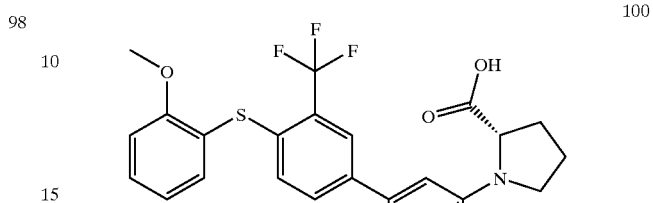

100

The title compound was prepared according to the procedures of Example 38E, substituting compound 76 with compound 96 (0.039 g, 0.0985 mmol) and 3-hydroxypyrrolidine with (D)-proline. A yellow solid 100 was obtained (0.0366 g, 78%). $^1$H-NMR (CDCl$_3$, 400 MHz) δ 2.14–2.38 (m, 3H), 2.48–2.55 (m, 1H), 3.58–3.66 (m, 1H), 3.80–3.89 (m, 1H), 3.83 (s, 3H), 4.96–5.05 (m, 1H), 6.82 (s, 1H), 6.96 (d, J=6.2 Hz, 1H), 7.01–7.07 (m, 3H), 7.46–7.52 (m, 3H), 7.84 (s, 1H), 8.04 (d, J=6.2 Hz, 1H). MS (APCI) m/z 475 (M+H)$^+$.

EXAMPLE 61

(4'-(4-(2-Methoxy-phenylsulfanyl)-3-trifluoromethyl-phenyl)-3,4,5,6-tetrahydro-2H-(1,2')bipyridinyl-4-yl)-methanol 101 was synthesized according to the following procedure.

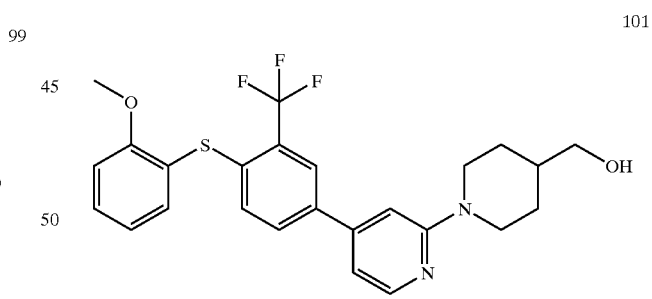

101

The title compound was prepared according to the procedures of Example 38E, substituting compound 76 with compound 96 (0.039 g, 0.0985 mmol) and 3-hydroxypyrrolidine with 4-piperidinemethanol. A yellow solid 101 was obtained (0.0299 g, 64%). $^1$H-NMR (CDCl$_3$, 400 MHz) δ 1.41–1.50 (m, 2H), 1.86–1.94 (m, 1H), 1.97–2.03 (m, 2H), 3.27 (t, J=13.6 Hz, 2H), 3.57 (d, J=5.8 Hz, 2H), 3.83 (s, 3H), 4.38 (d, J=13.5 Hz, 2H), 6.93 (d, J=6.6 Hz, 1H), 6.97 (s, 1H), 7.01–7.07 (m, 3H), 7.46–7.52 (m, 3H), 7.84 (s, 1H), 8.24 (d, J=6.2 Hz, 1H); MS (APCI) m/z 475 (M+H)$^+$.

EXAMPLE 62

N-1-(4-(4-(2-Methoxy-phenylsulfanyl)-3-trifluoromethyl-phenyl)-pyridin-2-yl)-pyrrolidine-3-yl)-acetamide 102 was synthesized according to the following procedure.

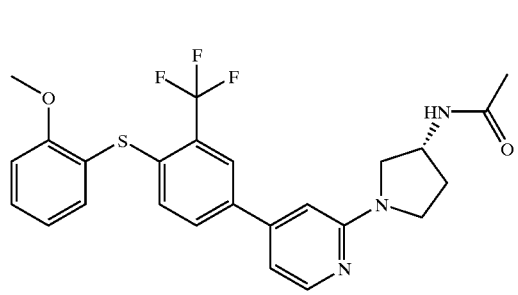

102

The title compound was prepared according to the procedures of Example 38E, substituting compound 76 with compound 96 (0.039 g, 0.0985 mmol) and 3-hydroxypyrrolidine with (3R)-(+)-3-acetamidopyrrolidine. A yellow solid 102 was obtained (0.0391 g, 81%). $^1$H-NMR (CDCl$_3$, 400 MHz) δ 2.00 (s, 3H), 2.23–2.29 (m, 1H), 2.33–2.40 (m, 1H), 3.78–3.88 (m, 3H), 3.83 (s, 3H), 4.00–4.07 (m, 1H), 4.62–4.67 (m, 1H), 6.78 (s, 1H), 6.95 (d, J=6.6 Hz, 1H), 7.01–7.07 (m, 3H), 7.20 (br s, 1H), 7.46–7.52 (m, 3H), 7.85 (s, 1H), 8.06 (d, J=6.6 Hz, 1H). MS (APCI) m/z 488 (M+H)$^+$.

EXAMPLE 63

N-1-(4-(4-(2-Methoxy-phenylsulfanyl)-3-trifluoromethyl-phenyl)-pyridin-2-yl)-pyrrolidine-3-yl)-acetamide 103 was synthesized according to the following procedure.

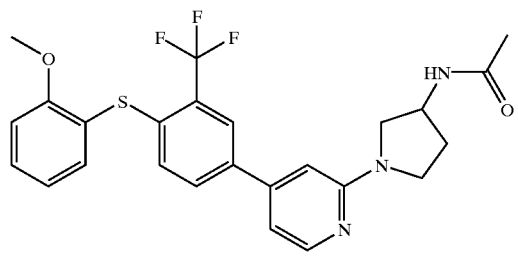

103

The title compound was prepared according to the procedures of Example 38E, substituting compound 76 with compound 96 (0.039 g, 0.0985 mmol) and 3-hydroxypyrrolidine with 3-acetamidopyrrolidine. A yellow solid 103 was obtained (0.0306 g, 64%). $^1$H-NMR (CDCl$_3$, 400 MHz) δ 2.01 (s, 3H), 2.25–2.31 (m, 1H), 2.33–2.41 (m, 1H), 3.80–3.90 (m, 3H), 3.83 (s, 3H), 4.01–4.10 (m, 1H), 4.63–4.69 (m, 1H), 6.79 (s, 1H), 6.96 (d, J=6.6 Hz, 1H), 7.01–7.07 (m, 3H), 7.12 (br s, 1H), 7.46–7.52 (m, 3H), 7.85 (s, 1H), 8.07 (d, J=6.6 Hz, 1H). MS (APCI) m/z 488 (M+H)$^+$.

EXAMPLE 64

1-(4-(4-(2-Methoxy-phenylsulfanyl)-3-trifluoromethyl-phenyl)-pyridin-2-yl)-piperazin-1-yl)-ethanone 104 was synthesized according to the following procedure.

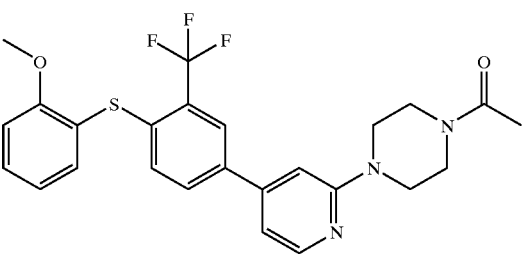

104

The title compound was prepared according to the procedures of Example 38E, substituting compound 76 with compound 96 (0.039 g, 0.0985 mmol) and 3-hydroxypyrrolidine with 1-acetylpiperazine. A yellow solid 104 was obtained (0.0197 g, 41%). $^1$H-NMR (CDCl$_3$, 400 MHz) δ 2.17 (s, 3H), 3.68–3.72 (m, 2H), 3.73–3.78 (m, 2H), 3.82–3.89 (m, 2H), 3.83 (s, 3H), 3.94–3.99 (m, 2H), 6.95 (s, 1H), 7.00–7.05 (m, 3H), 7.07 (d, J=8.4 Hz, 1H), 7.45–7.52 (m, 3H), 7.86 (s, 1H), 8.29 (d, J=6.2 Hz, 1H), MS (APCI) m/z 488 (M+H)$^+$.

EXAMPLE 65

(4'-(4-(2-Methoxy-phenylsulfanyl)-3-trifluoromethyl-phenyl)-3,4,5,6-tetrahydro-2H-(1,2')bipyridinyl-4-carboxylic acid amide 105 was synthesized according to the following procedure.

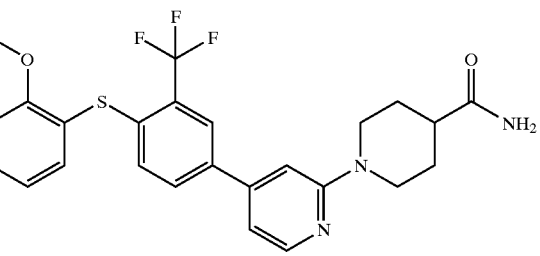

105

The title compound was prepared according to the procedures of Example 38E, substituting compound 76 with compound 96 (0.039 g, 0.0985 mmol) and 3-hydroxypyrrolidine with isonipecotamide. A yellow solid 105 was obtained (0.0272 g, 57%). $^1$H-NMR (CDCl$_3$, 400 MHz) δ 1.90–1.99 (m, 2H), 2.08–2.14 (m, 2H), 2.59–2.66 (m, 1H), 3.39–3.47 (m, 2H), 3.83 (s, 3H), 4.29–4.34 (m, 2H), 5.57 (br s, 1H), 5.99 (br s, 1H), 6.97 (d, J=6.6 Hz, 1H), 6.99 (s, 1H), 7.00–7.05 (m, 2H), 7.06 (d, J=8.4 Hz, 1H), 7.46–7.52 (m, 3H), 7.85 (s, 1H), 8.20 (d, J=6.6 Hz, 1H); MS (APCI) m/z 488 (M+H)$^+$.

EXAMPLE 66

4'-(4-(2-Methoxy-phenylsulfanyl)-3-trifluoromethyl-phenyl)-3,4,5,6-tetrahydro-2H-(1,2')bipyridinyl-4-carboxylic acid 106 was synthesized according to the following procedure.

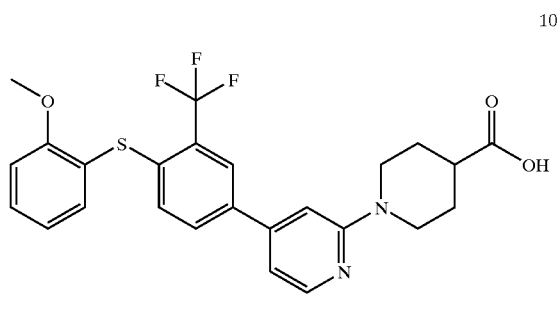

106

The title compound was prepared according to the procedures of Example 38E, substituting compound 76 with compound 96 (0.039 g, 0.0985 mmol) and 3-hydroxypyrrolidine with isonipecotic acid. A yellow solid 106 was obtained (0.0225 g, 47%). $^1$H-NMR (CDCl$_3$, 400 MHz) δ 1.90–1.99 (m, 2H), 2.09–2.16 (m, 2H), 2.68–2.77 (m, 1H), 3.43–3.50 (m, 2H), 3.83 (s, 3H), 4.14–4.20 (m, 2H), 6.95 (d, J=6.2 Hz, 1H), 6.99–7.05 (m, 3H), 7.06 (d, J=8.4 Hz, 1H), 7.45–7.52 (m, 3H), 7.84 (s, 1H), 8.20 (d, J=6.6 Hz, 1H); MS (APCI) m/z 489 (M+H)$^+$.

EXAMPLE 67

4'-(4-(2-Methoxy-phenylsulfanyl)-3-trifluoromethyl-phenyl)-3,4,5,6-tetrahydro-2H-(1,2')bipyridinyl-3-carboxylic acid amide 107 was synthesized according to the following procedure.

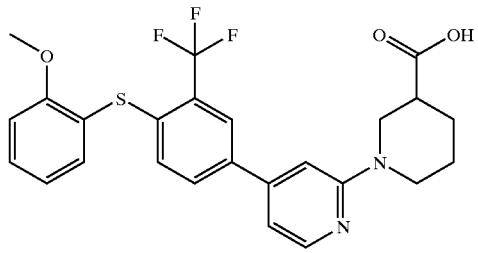

107

The title compound was prepared according to the procedures of Example 38E, substituting compound 76 with compound 96 (0.039 g, 0.0985 mmol) and 3-hydroxypyrrolidine with nipecotic acid. A yellow solid 107 was obtained (0.0283 g, 59%). $^1$H-NMR (CDCl$_3$, 400 MHz) δ 1.64–1.74 (m, 1H), 1.90–1.98 (m, 1H), 2.06–2.12 (m, 2H), 2.84–2.92 (m, 1H), 3.52–3.59 (m, 1H), 3.72–3.93 (m, 2H), 3.83 (s, 3H), 4.22–4.27 (m, 1H), 6.96 (d, J=5.9 Hz, 1H), 7.00–7.08 (m, 4H), 7.45–7.52 (m, 3H), 7.84 (s, 1H), 8.31 (d, J=6.5 Hz, 1H); MS (APCI) m/z 489 (M+H)$^+$.

EXAMPLE 68

2-(4'-(4-(2-Methoxy-phenylsulfanyl)-3-trifluoromethyl-phenyl)-3,4,5,6-tetrahydro-2H-(1,2')bipyridinyl-4-yl)-ethanol 108 was synthesized according to the following procedure.

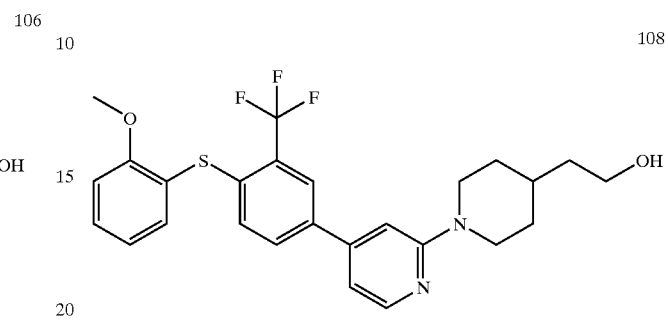

108

The title compound was prepared according to the procedures of Example 38E, substituting compound 76 with compound 96 (0.039 g, 0.0985 mmol) and 3-hydroxypyrrolidine with 4-(2'-hydroxyethyl)piperidine. A yellow solid 108 was obtained (0.0308 g, 64%). $^1$H-NMR (CDCl$_3$, 400 MHz) δ 1.34–1.43 (m, 2H), 1.58 (q, J=6.6 Hz, 2H), 1.84–1.93 (m, 1H), 1.96–2.02 (m, 2H), 3.21–3.29 (m, 2H), 3.74 (t, J=6.2 Hz, 2H), 3.83 (s, 3H), 4.33–4.39 (m, 2H), 6.91 (d, J=6.6 Hz, 1H), 6.96 (s, 1H), 7.00–7.07 (m, 3H), 7.45–7.52 (m, 3H), 7.84 (s, 1H), 8.24 (d, J=6.6 Hz, 1H); MS (APCI) m/z 489 (M+H)$^+$.

EXAMPLE 69

4-Hydroxy-1-(4-(4-(2-methoxy-phenylsulfanyl)-3-trifluoromethyl-phenyl)-pyridin-2-yl)-pyrrolidine-2-carboxylic acid 109 was synthesized according to the following procedure.

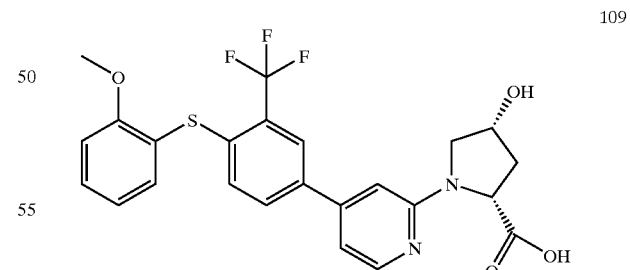

109

The title compound was prepared according to the procedures of Example 38E, substituting compound 76 with compound 96 (0.039 g, 0.0985 mmol) and 3-hydroxypyrrolidine with cis-4-hydroxy-D-proline. A yellow solid 109 was obtained (0.030 g, 63%). MS (APCI) m/z 491 (M+H)$^+$.

EXAMPLE 70

4-Hydroxy-1-(4-(4-(2-methoxy-phenylsulfanyl)-3-trifluoromethyl-phenyl)-pyridin-2-yl)-pyrrolidine-2-carboxylic acid 110 was synthesized according to the following procedure.

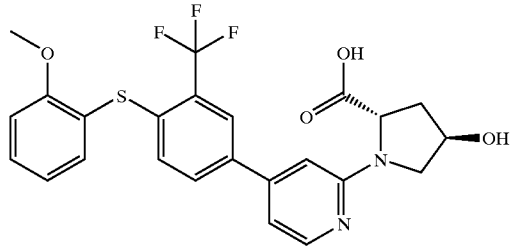

The title compound was prepared according to the procedures of Example 38E, substituting compound 76 with compound 96 (0.039 g, 0.0985 mmol) and 3-hydroxypyrrolidine with trans-4-hydroxy-L-proline. A yellow solid 110 was obtained (0.031 g, 65%). MS (APCI) m/z 491 (M+H)+.

EXAMPLE 71

N-1-(4-(4-(2-Methoxy-phenylsulfanyl)-3-trifluoromethyl-phenyl)-pyridin-2-yl)-pyrrolidine-3-yl)-N-methyl-acetamide 111 was synthesized according to the following procedure.

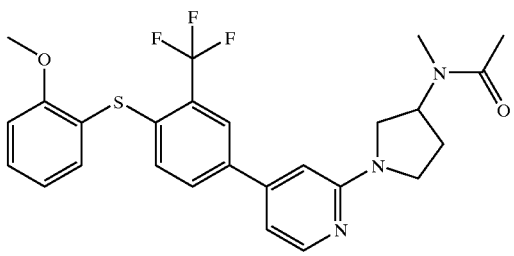

The title compound was prepared according to the procedures of Example 38E, substituting compound 76 with compound 96 (0.039 g, 0.0985 mmol) and 3-hydroxypyrrolidine with 3-(N-acetyl-N-methylamino)pyrrolidine. A yellow solid 111 was obtained (0.0211 g, 43%). $^1$H-NMR (CDCl$_3$, 400 MHz) δ 2.15 (s, 3H), 2.22–2.30 (m, 1H), 2.31–2.39 (m, 1H), 3.00 (s, 3H), 3.62–3.69 (m, 1H), 3.71–3.78 (m, 1H), 3.83 (s, 3H), 3.90–3.96 (m, 1H), 3.98–4.06 (m, 1H), 5.20–5.28 (m, 1H), 6.76 (s, 1H), 6.97 (d, J=6.2 Hz, 1H), 7.00–7.04 (m, 2H), 7.06 (d, J=8.4 Hz, 1H), 7.45–7.52 (m, 3H), 7.86 (s, 1H), 8.22 (d, J=6.6 Hz, 1H); MS (APCI) m/z 502 (M+H)+.

EXAMPLE 72

1-(4-(4-(4-(2-Methoxy-phenylsulfanyl)-3-trifluoromethyl-phenyl)-pyridin-2-yl)-(1,4)diazepan-1-yl)-ethanone 112 was synthesized according to the following procedure.

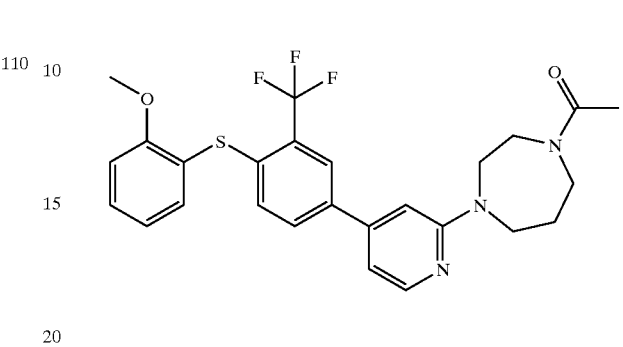

The title compound was prepared according to the procedures of Example 38E, substituting compound 76 with compound 96 (0.039 g, 0.0985 mmol) and 3-hydroxypyrrolidine with N-acetylhomopiperazine. A yellow solid 112 was obtained (0.0246 g, 50%). $^1$H-NMR (CDCl$_3$, 400 MHz) δ 2.02–2.10 (m, 2H), 2.08 (s, 3H), 3.55 (t, J=5.9 Hz, 1H), 3.59 (t, J=5.5 Hz, 1H), 3.79 (t, J=6.2 Hz, 1H), 3.83 (s, 3H), 3.84–3.92 (m, 3H), 4.05 (t, J=5.3 Hz, 1H), 4.15 (t, J=5.5 Hz, 1H), 6.86 (s, 1/3H), 6.89 (s, 2H), 6.92–7.08 (m, 4H), 7.45–7.53 (m, 3H), 7.84 (s, 1/3H), 7.85 (s, 2/3H), 8.26–8.30 (m, 1H), MS (APCI) m/z 502 (M+H)+.

EXAMPLE 73

(3-(4-(4-(4-(2-Methoxy-phenylsulfanyl)-3-trifluoromethyl-phenyl)-pyridin-2-yl)-piperazine-1-yl)-propyl)-dimethyl-amine 113 was synthesized according to the following procedure.

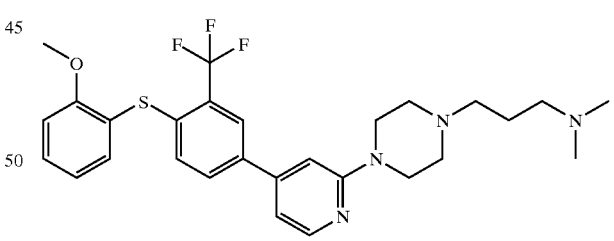

The title compound was prepared according to the procedures of Example 38E, substituting compound 76 with compound 96 (0.039 g, 0.0985 mmol) and 3-hydroxypyrrolidine with 1-(3-dimethylaminopropyl)piperazine. A yellow solid 113 was obtained (0.0414 g, 79%). $^1$H NMR (CDCl$_3$, 400 MHz) δ 2.20–2.50 (br, 6H), 2.42–2.50 (m, 2H), 2.86 (s, 6H), 3.21–3.28 (m, 2H), 3.32–3.38 (br, 2H), 3.83 (s, 3H), 4.05–4.10 (br, 2H), 6.88 (s, 1H), 6.99–7.06 (m, 3H), 7.10 (d, J=8.2 Hz, 1H), 7.43–7.52 (m, 3H), 7.85 (s, 1H), 8.25 (d, J=5.5 Hz, 1H); MS (APCI) m/z 531 (M+H)+.

EXAMPLE 74

1-(4-(4-(2-Methoxy-phenylsulfanyl)-3-trifluoromethyl-phenyl)-pyridin-2-yl)-4-propyl-piperazine 114 was synthesized according to the following procedure.

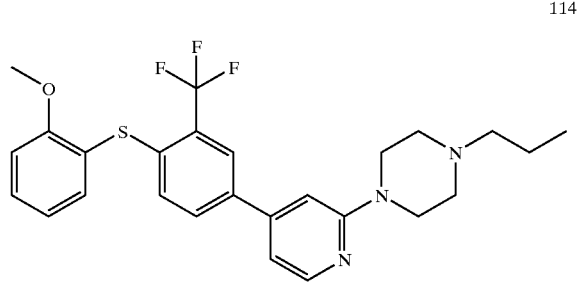

The title compound was prepared according to the procedures of Example 38E, substituting compound 76 with compound 96 (0.039 g, 0.0985 mmol) and 3-hydroxypyrrolidine with 1-propylpiperazine. A yellow solid 114 was obtained (0.033 g, 69%). $^1$H-NMR (CDCl$_3$, 400 MHz) δ 1.03 (t, J=7.3 Hz, 3H), 1.83–1.92 (m, 2H), 2.65–3.10 (br, 8H), 2.98–3.04 (m, 2H), 3.83 (s, 3H), 6.89 (s, 1H), 6.99–7.06 (m, 3H), 7.09 (d, J=8.1 Hz, 1H), 7.43–7.52 (m, 3H), 7.85 (s, 1H), 8.26 (d, J=5.9 Hz, 1H); MS (APCI) m/z 488 (M+H)$^+$.

EXAMPLE 75

(4'-(4-(2-Methoxy-phenylsulfanyl)-3-trifluoromethyl-phenyl)-3,4,5,6-tetrahydro-2H-(1,2')bipyridinyl-3-yl)-methanol 115 was synthesized according to the following procedure.

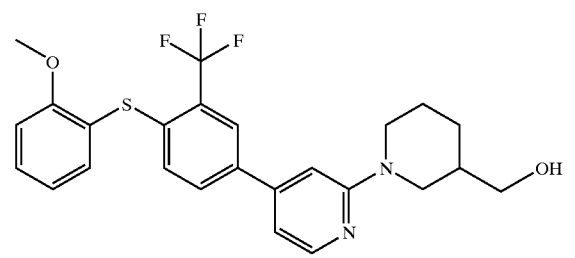

The title compound was prepared according to the procedures of Example 38E, substituting compound 76 with compound 96 (0.039 g, 0.0985 mmol) and 3-hydroxypyrrolidine with 3-hydroxymethyl piperidine. A yellow solid 115 was obtained (0.0279 g, 60%). $^1$H-NMR (CDCl$_3$, 400 MHz) δ 1.32–1.42 (m, 1H), 1.63–1.74 (m, 1H), 1.86–1.95 (m, 2H), 2.04–2.14 (m, 1H), 3.18–3.25 (m, 1H), 3.33–3.39 (m, 1H), 3.47–3.52 (m, 1H), 3.71 (dd, J=4.0 Hz, 11.0 Hz, 1H), 3.83 (s, 3H), 4.02–4.07 (m, 1H), 4.48–4.53 (m, 1H), 6.93 (d, J=6.6 Hz, 1H), 7.00–7.08 (m, 4H), 7.45–7.52 (m, 3H), 7.84 (s, 1H), 8.35 (d, J=6.5 Hz, 1H); MS (APCI) m/z 475 (M+H)$^+$.

EXAMPLE 76

1-(4-(4-(2,3-Dihydro-benzo(1,4)dioxin-6-ylsulfanyl)-3-trifluoromethyl-phenyl)-pyridin-2-yl)-pyrrolidin-3-ol 116 was synthesized according to the following procedure.

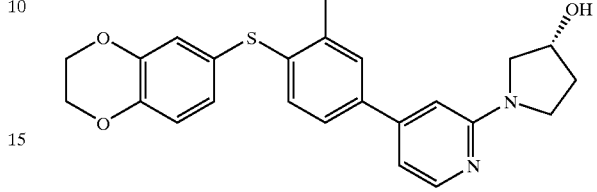

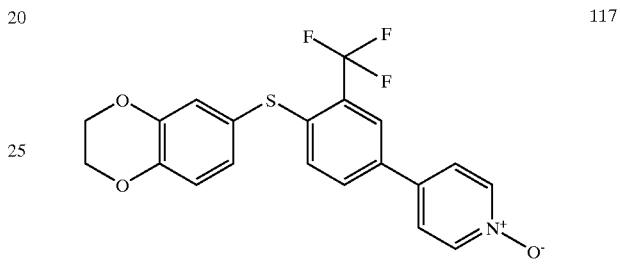

76A. First, 4-(4-(2,3-dihydro-benzo(1,4)dioxin-6-ylsulfanyl)-3-trifluoromethyl-phenyl)-pyridine 1-oxide 117 was synthesized according to the following procedure.

The title compound was prepared according to the procedures of Example 38C, substituting 2-isopropylthiophenol with 3,4-ethylenedioxythiophenol (0.671 g, 3.99 mmol). A white solid 117 was obtained (1.39 g, 90%). $^1$H-NMR (DMSO, 400 MHz) δ 4.27–4.34 (m, 4H), 7.01–7.08 (m, 3H), 7.12 (d, J=8.4 Hz, 1H), 7.83 (d, J=7.3 Hz, 2H), 7.93 (dd, J=2.2 Hz, 8.5 Hz, 1H), 8.09 (d, J=2.2 Hz, 1H), 8.27 (d, J=7.4 Hz, 2H); MS (APCI) m/z 406 (M+H)$^+$.

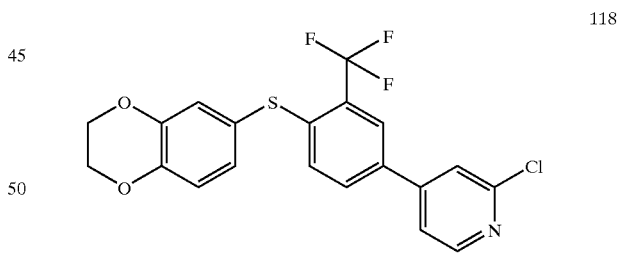

76B. Then, 2-chloro-(4-(4-(2,3-dihydro-benzo(1,4) dioxin-6-ylsulfanyl)-3-trifluoromethyl-phenyl)-pyridine 118 was synthesized according to the following procedure.

The title compound was prepared according to the procedures of Example 38D, substituting compound 75 with compound 117 (1.37 g, 3.38 mmol). A yellow oil 118 was obtained (0.87 g, 60%). $^1$H-NMR (DMSO, 400 MHz) δ 4.28–4.35 (m, 4H), 7.03–7.13 (m, 4H), 7.80 (dd, J=1.4 Hz, 5.2 Hz, 1H), 7.94 (d, J=1.2 Hz, 1H), 7.99 (dd, J=1.8 Hz, 8.5 Hz, 1H), 8.16 (d, J=1.8 Hz, 1H), 8.47 (d, J=5.2 Hz, 1H); MS (APCI) m/z 424 (M+H)$^+$.

76C. The title compound was prepared according to the procedures of Example 38E, substituting compound 76 with compound 118 (0.033 g, 0.0779 mmol) and 3-hydroxypyrrolidine with (R)-3-hydroxypyrrolidine. A yellow solid 116 was obtained (0.0353 g, 75%). $^1$H-NMR (CDCl$_3$, 400 MHz) δ 2.15–2.23 (m, 1H), 2.25–2.31 (m, 1H), 3.78–3.84 (m, 2H), 3.87–3.95 (m, 2H), 4.28–4.34 (m, 4H), 4.72–4.76 (m, 1H), 6.77 (s, 1H), 6.91 (dd, J=1.1 Hz, 6.6 Hz, 1H), 6.95 (d, J=8.1 Hz, 1H), 7.05 (dd, J=2.1 Hz, 8.1 Hz, 1H), 7.10 (d, J=2.2 Hz, 1H), 7.12 (d, J=8.4 Hz, 1H), 7.54 (dd, J=1.4 Hz, 8.5 Hz, 1H), 7.83 (d, J=1.1 Hz, 1H), 8.15 (d, J=6.6 Hz, 1H); MS (APCI) m/z 475 (M+H)$^+$.

EXAMPLE 77

4'-(4-(2,3-Dihydro-benzo(1,4)dioxin-6-ylsulfanyl)-3-trifluoromethyl-phenyl)-3,4,5,6-tetrahydro-2H-(1,2')bipyridinyl-4-ol 119 was synthesized according to the following procedure.

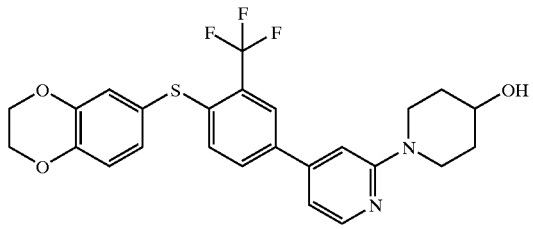

119

The title compound was prepared according to the procedures of Example 38E, substituting compound 76 with compound 118 (0.033 g, 0.0779 mmol) and 3-hydroxypyrrolidine with 4-hydroxypiperdine. A yellow solid 119 was obtained (0.031 g, 63%). $^1$H-NMR (CDCl$_3$, 400 MHz) δ 1.75–1.84 (m, 2H), 2.02–2.10 (m, 2H), 3.67–3.74 (m, 2H), 4.00–4.07 (m, 2H), 4.10–4.16 (m, 1H), 4.28–4.34 (m, 4H), 4.72–4.76 (m, 1H), 6.93–6.97 (m, 3H), 7.05 (dd, J=1.8 Hz, 8.0 Hz, 1H), 7.10 (d, J=1.8 Hz, 1H), 7.12 D, J=8.5 Hz, 1H), 7.52 (d, J=8.4 Hz, 1H), 7.82 (s, 1H), 8.25 (d, J=6.3 Hz, 1H), MS (APCI) m/z 489 (M+H)$^+$.

EXAMPLE 78

(1-(4-(4-(2,3-Dihydro-benzo(1,4)dioxin-6-ylsulfanyl)-3-trifluoromethyl-phenyl)-pyridin-2-yl)-pyrrolidin-2-yl)-methanol 120 was synthesized according to the following procedure.

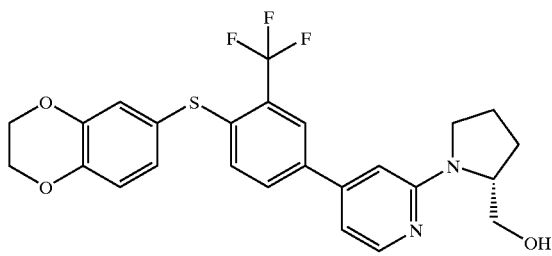

120

The title compound was prepared according to the procedures of Example 38E, substituting compound 76 with compound 118 (0.033 g, 0.0779 mmol) and 3-hydroxypyrrolidine with (R)-2-(hydroxymethyl)pyrrolidine. A yellow solid 120 was obtained (0.027 g, 55%). $^1$H-NMR (CDCl$_3$, 400 MHz) δ 2.06–2.11 (m, 2H), 2.16–21 (m, 2H), 3.46–3.53 (m, 1H), 3.63–3.76 (m, 3H), 4.28–4.34 (m, 4H), 4.61–4.66 (m, 1H), 6.78 (s, 1H), 6.92 (dd, J=1.4 Hz, 6.9 Hz, 1H), 6.95 (d, J=8.4 Hz, 1H), 7.05 (dd, J=2.2 Hz, 8.0 Hz, 1H), 7.10 (d, J=2.2 Hz, 1H), 7.12 (d, J=8.5 Hz, 1H), 7.52 (dd, J=1.9 Hz, 8.4 Hz, 1H), 7.82 (d, J=1.4 Hz, 1H), 8.13 (d, J=6.6 Hz, 1H); MS (APCI) m/z 489 (M+H)$^+$·

EXAMPLE 79

1-(4-(4-(2,3-Dihydro-benzo(1,4)dioxin-6-ylsulfanyl)-3-trifluoromethyl-phenyl)-pyridin-2-yl)-pyrrolidine-2-carboxylic acid 121 was synthesized according to the following procedure.

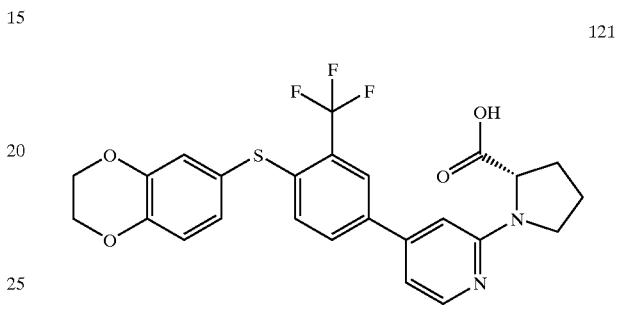

121

The title compound was prepared according to the procedures of Example 38E, substituting compound 76 with compound 118 (0.033 g, 0.0779 mmol) and 3-hydroxypyrrolidine with (D)-proline. A yellow solid 121 was obtained (0.035 g, 70%). MS (APCI) m/z 503 (M+H)$^+$.

EXAMPLE 80

(4'-(4-(2,3-Dihydro-benzo(1,4)dioxin-6-ylsulfanyl)-3-trifluoromethyl-phenyl)-3,4,5,6-tetrahydro-2H-(1,2')bipyridinyl-4-yl)-methanol 122 was synthesized according to the following procedure.

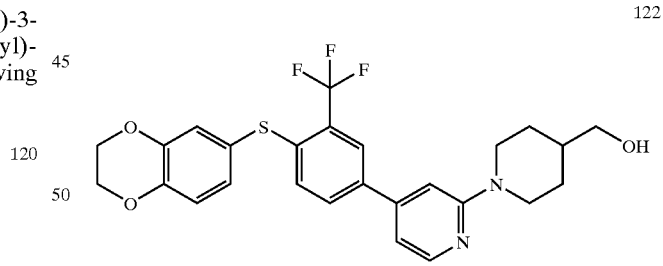

122

The title compound was prepared according to the procedures of Example 38E, substituting compound 76 with compound 118 (0.033 g, 0.0779 mmol) and 3-hydroxypyrrolidine with 4-piperidinemethanol. A yellow solid 122 was obtained (0.0284 g, 57%). $^1$H-NMR (CDCl$_3$, 400 MHz) δ 1.41–1.51 (m, 2H), 1.86–1.95 (m, 1H), 1.97–2.04 (m, 2H), 3.23–3.31 (m, 2H), 3.57 (d, J=5.8 Hz, 2H), 4.28–4.34 (m, 4H), 4.36–4.41 (m, 2H), 6.92 (d, J=6.6 Hz, 1H), 6.93–6.97 (m, 2H), 7.05 (dd, J=1.8 Hz, 8.4 Hz, 1H),7.09 (d, J=1.8 Hz, 1H), 7.12 (d, J=8.4 Hz, 1H), 7.52 (d, J=8.4 Hz, 1H), 7.82 (s, 1H), 8.25 (d, J=6.6 Hz, 1H); MS (APCI) m/z 503 (M+H)$^+$.

EXAMPLE 81

N-(1-(4-(4-(2,3-Dihydro-benzo(1,4)dioxin-6-ylsulfanyl)-3-trifluoromethyl-phenyl)-pyridin-2-yl)-pyrrolidin-3-yl)-acetamide 123 was synthesized according to the following procedure.

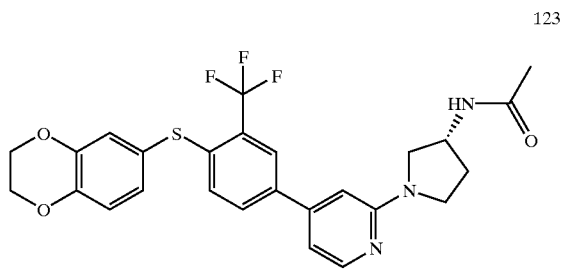

123

The title compound was prepared according to the procedures of Example 38E, substituting compound 76 with compound 118 (0.033 g, 0.0779 mmol) and 3-hydroxypyrrolidine with (3R)-(+)-3-acetamidopyrroli- dine. A yellow solid 123 was obtained (0.0397 g, 78%). $^1$H-NMR (CDCl$_3$, 400 MHz) δ 2.03 (s, 3H), 2.25–2.31 (m, 1H), 2.34–2.42 (m, 1H), 3.80–3.90 (m, 3H), 4.02–4.11 (m, 1H), 4.28–4.34 (m, 4H), 4.63–4.68 (m, 1H), 6.78 (s, 1H), 6.93–6.97 (m, 2H), 7.05 (dd, J=2.2 Hz, 8.4 Hz, 1H), 7.09–7.13 (m, 2H), 7.18 (brs, 1H), 7.53 (d, J=8.4 Hz, 1H), 7.83 (s, 1H), 8.07 (d, J=6.6 Hz, 1H); MS (APCI) m/z 516 (M+H)$^+$.

EXAMPLE 82

N-(1-(4-(4-(2,3-Dihydro-benzo(1,4)dioxin-6-ylsulfanyl)-3-trifluoromethyl-phenyl)-pyridin-2-yl)-pyrrolidin-3-yl)-acetamide 124 was synthesized according to the following procedure.

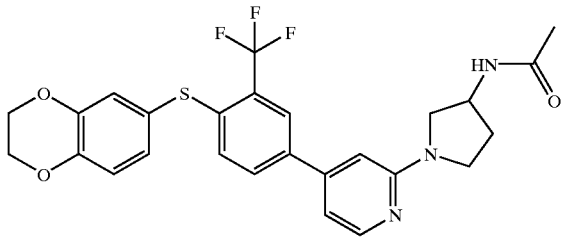

124

The title compound was prepared according to the procedures of Example 38E, substituting compound 76 with compound 118 (0.033 g, 0.0779 mmol) and 3-hydroxypyrrolidine with 3-acetamidopyrrolidine. A yellow solid 124 was obtained (0.0369 g, 72%). $^1$H NMR (CDCl$_3$, 400 MHz) δ 2.01 (s, 3H), 2.24–2.31 (m, 1H), 2.34–2.41 (m, 1H), 3.78–3.90 (m, 3H), 4.01–4.10 (m, 1H), 4.28–4.34 (m, 4H), 4.62–4.68 (m, 1H), 6.78 (s, 1H), 6.93–6.97 (m, 2H), 7.05 (dd, J=2.2 Hz, 8.4 Hz, 1H), 7.09–7.13 (m, 2H), 7.18 (br s, 1H), 7.53 (d, J=8.4 Hz, 1H), 7.83 (s, 1H), 8.07 (d, J=6.6 Hz, 1H), MS (APCI) m/z 516 (M+H)$^+$.

EXAMPLE 83

(1-(4-(4-(2,3-Dihydro-benzo(1,4)dioxin-6-ylsulfanyl)-3-trifluoromethyl-phenyl)-pyridin-2-yl)-piperazin-1-yl)-ethanone 125 was synthesized according to the following procedure.

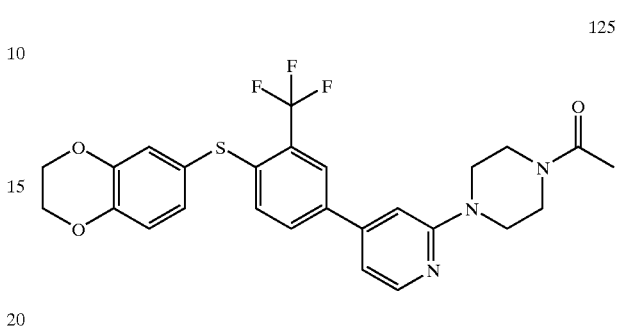

125

The title compound was prepared according to the procedures of Example 38E, substituting compound 76 with compound 118 (0.033 g, 0.0779 mmol) and 3-hydroxypyrrolidine with 1-acetylpiperazine. A yellow solid 125 was obtained (0.010 g, 19%). $^1$H-NMR (CDCl$_3$, 400 MHz) δ 2.17 (s, 3H), 3.67–3.72 (m, 2H), 3.73–3.77 (m, 2H), 3.83–3.88 (m, 2H), 3.94–3.98 (m, 2H), 4.28–4.34 (m, 4H), 6.93 (s, 1H), 6.95 (d, J=8.4 Hz, 1H), 7.02 (d, J=5.8 Hz, 1H), 7.05 (dd, J=2.2 Hz, 8.4 Hz, 1H), 7.09 (d, J=2.2 Hz, 1H), 7.13 (d, J=8.4 Hz, 1H), 7.53 (d, J=8.1 Hz, 1H), 7.83 (s, 1H), 8.29 (d, J=6.2 Hz, 1H); MS (APCI) m/z 516 (M+H)$^+$.

EXAMPLE 84

4'-(4-(2,3-Dihydro-benzo(1,4)dioxin-6-ylsulfanyl)-3-trifluoromethyl-phenyl)-3,4,5,6-tetrahydro-2H-(1,2')bipyridinyl-4-carboxylic acid amide 126 was synthesized according to the following procedure.

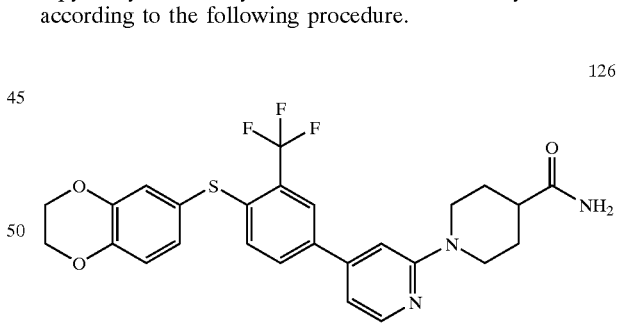

126

The title compound was prepared according to the procedures of Example 38E, substituting compound 76 with compound 118 (0.033 g, 0.0779 mmol) and 3-hydroxypyrrolidine with isonipecotamide. A yellow solid 126 was obtained (0.024 g, 47%). $^1$H-NMR (CDCl$_3$, 400 MHz) δ 1.90–1.99 (m, 2H), 2.08–2.14 (m, 2H), 2.58–2.65 (m, 1H), 3.38–3.45 (m, 2H), 4.28–4.34 (m, 6H), 5.55 (br s, 1H), 5.97 (br s, 1H), 6.93–6.98 (m, 3H), 7.05 (dd, J=2.0 Hz, 8.2 Hz, 1H), 7.09 (d, J=1.8 Hz, 1H), 7.12 (d, J=8.4 Hz, 1H), 7.53 (d, J=8.4 Hz, 1H), 7.82 (s, 1H), 8.21 (d, J=6.6 Hz, 1H); MS (APCI) m/z 516 (M+H)$^+$.

EXAMPLE 85

4'-(4-(2,3-Dihydro-benzo(1,4)dioxin-6-ylsulfanyl)-3-trifluoromethyl-phenyl)-3,4,5,6-tetrahydro-2H-(1,2')bipyridinyl-4-carboxylic acid 127 was synthesized according to the following procedure.

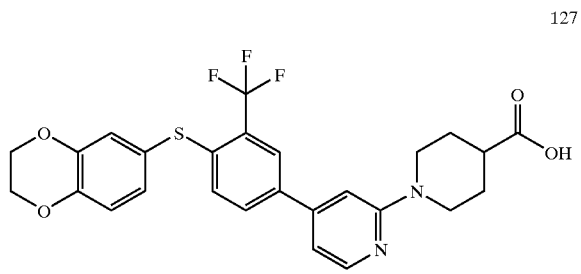

127

The title compound was prepared according to the procedures of Example 38E, substituting compound 76 with compound 118 (0.033 g, 0.0779 mmol) and 3-hydroxypyrrolidine with isonipecotic acid. A yellow solid 127 was obtained (0.014 g, 28%). $^1$H-NMR (CDCl$_3$, 400 MHz) δ 1.89–1.98 (m, 2H), 2.08–2.15 (m, 2H), 2.68–2.76 (m, 1H), 3.40–3.48 (m, 2H), 4.13–4.20 (m, 2H), 4.28–4.34 (m, 4H), 6.91–6.98 (m, 3H), 7.04 (dd, J=1.9 Hz, 8.4 Hz, 1H), 7.09 (d, J=2.2 Hz, 1H), 7.12 (d, J=8.4 Hz, 1H), 7.52 (d, J=8.4 Hz, 1H), 7.82 (s, 1H), 8.20 (d, J=6.2 Hz, 1H); MS (APCI) m/z 517 (M+H)$^+$.

EXAMPLE 86

4'-(4-(2,3-Dihydro-benzo(1,4)dioxin-6-ylsulfanyl)-3-trifluoromethyl-phenyl)-3,4,5,6-tetrahydro-2H-(1,2')bipyridinyl-3-carboxylic acid 128 was synthesized according to the following procedure.

128

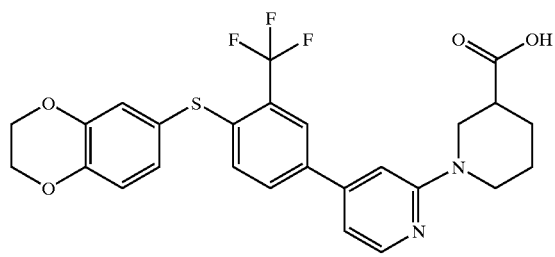

The title compound was prepared according to the procedures of Example 38E, substituting compound 76 with compound 118 (0.033 g, 0.0779 mmol) and 3-hydroxypyrrolidine with nipecotic acid. A yellow solid 128 was obtained (0.034 g, 66%). $^1$H-NMR (CDCl$_3$, 400 MHz) δ 1.64–1.74 (m, 1H), 1.92–1.99 (m, 1H), 2.06–2.13 (m, 2H), 2.88–2.95 (m, 1H), 3.50–3.57 (m, 1H), 3.68–3.74 (m, 2H), 3.90–3.96 (m, 1H), 4.28–4.36 (m, 4H), 6.94–6.98 (m, 2H), 7.03–7.07 (m, 2H), 7.09 (d, J=1.9 Hz, 1H), 7.12 (d, J=8.8 Hz, 1H), 7.52 (d, J=8.5 Hz, 1H), 7.82 (s, 1H), 8.32 (d, J=6.2 Hz, 1H); MS (APCI) m/z 517 (M+H)$^+$.

EXAMPLE 87

2-(4'-(4-(2,3-Dihydro-benzo(1,4)dioxin-6-ylsulfanyl)-3-trifluoromethyl-phenyl)-3,4,5,6-tetrahydro-2H-(1,2')bipyridinyl-4-yl)-ethanol 129 was synthesized according to the following procedure.

129

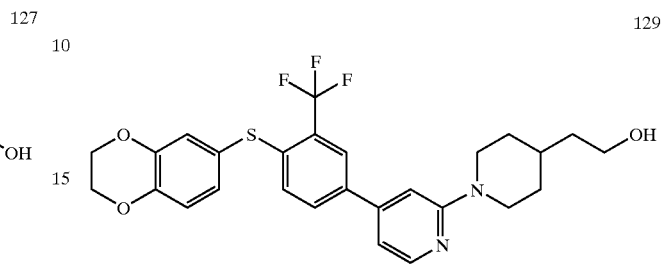

The title compound was prepared according to the procedures of Example 38E, substituting compound 76 with compound 118 (0.033 g, 0.0779 mmol) and 3-hydroxypyrrolidine with 4-(2'-hydroxyethyl)piperidine. A yellow solid 129 was obtained (0.037 g, 73%). $^1$H NMR (CDCl$_3$, 400 MHz) δ 1.35–1.44 (m, 2H), 1.55–1.60 (m, 2H), 1.84–1.93 (m, 1H), 1.97–2.03 (m, 2H), 3.22–3.30 (m, 2H), 3.74 (t, J=6.2 Hz, 2H), 4.28–4.34 (m, 4H), 4.36–4.42 (m, 2H), 6.91 (d, J=6.6 Hz, 1H), 6.93–6.96 (m, 2H), 7.05 (dd, J=2.2 Hz, 8.4 Hz, 1H), 7.09 (d, J=2.2 Hz, 1H), 7.12 (d, J=8.8 Hz, 1H), 7.51 (d, J=8.8 Hz, 1H), 7.81 (s, 1H), 8.24 (d, J=6.6 Hz, 1H); MS (APCI) m/z 517 (M+H)$^+$.

EXAMPLE 88

1-(4-(4-(2,3-Dihydro-benzo(1,4)dioxin-6-ylsulfanyl)-3-trifluoromethyl-phenyl)-pyridin-2-yl)-4-hydroxy-pyrrolidine-2-carboxylic acid 130 was synthesized according to the following procedure.

130

The title compound was prepared according to the procedures of Example 38E, substituting compound 76 with compound 118 (0.033 g, 0.0779 mmol) and 3-hydroxypyrrolidine with cis-4-hydroxy-D-proline. A yellow solid 130 was obtained (0.038 g, 74%). $^1$H-NMR (CDCl$_3$, 400 MHz) δ 2.34–2.42 (m, 1H), 2.64–2.68 (m, 2H), 3.73–3.82 (m, 1H), 3.94–4.00 (m, 1H), 4.28–4.34 (m, 4H), 4.68–4.74 (m, 1H), 6.92–7.12 (m, 6H), 7.52 (br, 1H), 7.80 (s, 1H), 8.04 (br, 1H); MS (APCI) m/z 519 (M+H)$^+$.

EXAMPLE 89

1-(4-(4-(2,3-Dihydro-benzo(1,4)dioxin-6-ylsulfanyl)-3-trifluoromethyl-phenyl)-pyridin-2-yl)-4-hydroxy-pyrrolidine-2-carboxylic acid 131 was synthesized according to the following procedure.

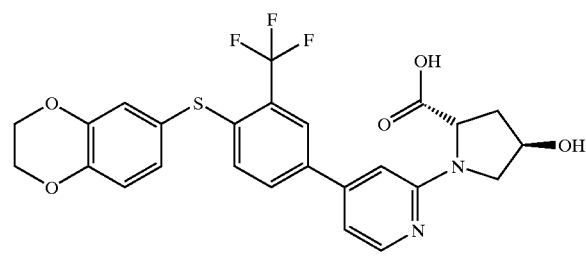

The title compound was prepared according to the procedures of Example 38E, substituting compound 76 with compound 118 (0.033 g, 0.0779 mmol) and 3-hydroxypyrrolidine with trans-4-hydroxy-L-proline. A yellow solid 131 was obtained (0.017 g, 33%). $^1$H-NMR (CDCl$_3$, 400 MHz) δ 2.42–2.51 (m, 1H), 3.66–3.72 (m, 1H), 3.85–3.91 (m, 1H), 4.00–4.06 (m, 1H), 4.28–4.34 (m, 4H), 4.64–4.69 (m, 1H), 4.85–4.95 (m, 1H), 6.81 (s, 1H), 6.92–6.96 (m, 2H), 7.03 (dd, J=1.8 Hz, 8.4 Hz, 1H), 7.06–7.10 (m, 2H), 7.50 (d, J=8.4 Hz, 1H), 7.79 (s, 1H), 7.92–7.96 (m, 1H); MS (APCI) m/z 519 (M+H)$^+$.

EXAMPLE 90

N-1-(4-(4-(2,3-Dihydro-benzo(1,4)dioxin-6-ylsulfanyl)-3-trifluoromethyl-phenyl)-pyridin-2-yl)-pyrrolidin-3-yl)-N-methyl-acetamide 132 was synthesized according to the following procedure.

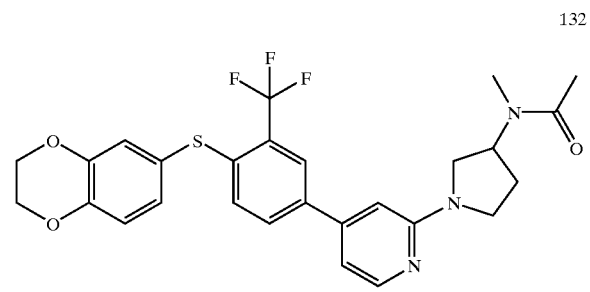

The title compound was prepared according to the procedures of Example 38E, substituting compound 76 with compound 118 (0.033 g, 0.0779 mmol) and 3-hydroxypyrrolidine with 3-(N-acetyl-N-methylamino)pyrrolidine. A yellow solid 132 was obtained (0.022 g, 42%). $^1$H-NMR (CDCl$_3$, 400 MHz) δ 2.15 (s, 3H), 2.20–2.29 (m, 1H), 2.32–2.40 (m, 1H), 3.00 (s, 3H), 3.62–3.70 (m, 1H), 3.71–3.78 (m, 1H), 3.90–3.96 (m, 1H), 3.98–4.06 (m, 1H), 4.28–4.34 (m, 4H), 5.21–5.29 (m, 1H), 6.74 (s, 1H), 6.93–6.97 (m, 2H), 7.05 (dd, J=2.2 Hz, 8.4 Hz, 1H), 7.10 (d, J=1.8 Hz, 1H), 7.12 (d, J=8.4 Hz, 1H), 7.53 (d, J=8.1 Hz, 1H), 7.83 (s, 1H), 8.23 (d, J=6.6 Hz, 1H); MS (APCI) m/z 530 (M+H)$^+$.

EXAMPLE 91

1-(4-(4-(4-(2,3-Dihydro-benzo(1,4)dioxin-6-ylsulfanyl)-3-trifluoromethyl-phenyl)-pyridin-2-yl)-(1,4)diazepan-1-yl)-ethanone 133 was synthesized according to the following procedure.

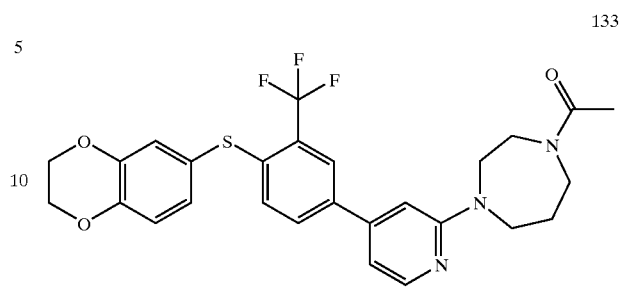

The title compound was prepared according to the procedures of Example 38E, substituting compound 76 with compound 118 (0.033 g, 0.0779 mmol) and 3-hydroxypyrrolidine with N-acetylhomopiperazine. A yellow solid 133 was obtained (0.021 g, 40%). $^1$H-NMR (CDCl$_3$, 400 MHz) δ 2.01–2.10 (m, 2H), 2.08 (s, 3H), 3.52–3.60 (m, 2H), 3.76–3.91 (m, 4H), 4.01–4.06 (m, 1H), 4.11–4.16 (m, 1H), 4.28–4.34 (m, 4H), 6.85 (s, 1/3H), 6.87 (s, 2/3H), 6.95 (d, J=8.4 Hz, 1H), 6.97 (d, J=6.6 Hz, 1H), 7.05 (dd, J=1.4 Hz, 8.4 Hz, 1H), 7.10 (d, J=2.2 Hz, 1H), 7.11–7.14 (m, 1H), 7.50–7.56 (m, 1H), 7.81 (s, 1/3H), 7.82 (s, 2/3H), 8.26–8.30 (m, 1H); MS (APCI) m/z 530 (M+H)$^+$.

EXAMPLE 92

(3-(4-(4-(2,3-Dihydro-benzo(1,4)dioxin-6-ylsulfanyl)-3-trifluoromethyl-phenyl)-pyridin-2-yl)-piperazin-1-yl)-propyl)-dimethyl-amine 134 was synthesized according to the following procedure.

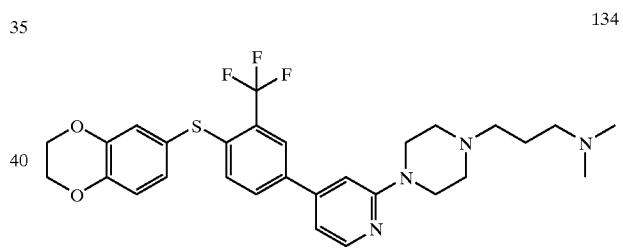

The title compound was prepared according to the procedures of Example 38E, substituting compound 76 with compound 118 (0.033 g, 0.0779 mmol) and 3-hydroxypyrrolidine with 1-(3-dimethylaminopropyl)piperazine. A yellow solid 134 was obtained (0.0401 g, 73%). MS (APCI) m/z 559 (M+H)$^+$.

EXAMPLE 93

1-(4-(4-(2,3-Dihydro-benzo(1,4)dioxin-6-ylsulfanyl)-3-trifluoromethyl-phenyl)-pyridin-2-yl)-4-propyl-piperazine 135 was synthesized according to the following procedure.

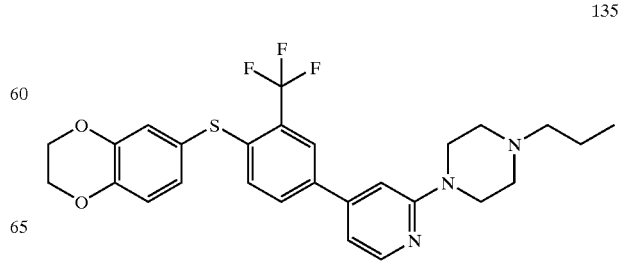

The title compound was prepared according to the procedures of Example 38E, substituting compound 76 with compound 118 (0.033 g, 0.0779 mmol) and 3-hydroxypyrrolidine with 1-propylpiperazine. A yellow solid 135 was obtained (0.033 g, 64%). $^1$H-NMR (CDCl$_3$, 400 MHz) δ 1.03 (t, J=7.3 Hz, 3H), 1.84–1.92 (m, 2H), 2.30–2.52 (br, 8H), 2.98–3.03 (m, 2H), 4.28–4.34 (m, 4H), 6.87 (s, 1H), 6.94 (d, J=1H), 7.01 (d, J=5.8 Hz, 1H), 7.04 (dd, J=2.2 Hz, 8.4 Hz, 1H), 7.09 (d, J=2.2 Hz, 1H), 7.13 (d, J=8.4 Hz, 1H), 7.51 (d, J=8.3 Hz, 1H), 7.82 (s, 1H), 8.26 (d, J=5.9 Hz, 1H); MS (APCI) m/z 516 (M+H)$^+$.

EXAMPLE 94

1-Allyl-4-(4-(4-(2,3-dihydro-benzo(1,4)dioxin-6-ylsulfanyl)-3-trifluoromethyl-phenyl)-pyridin 2-yl)-piperazine 136 was synthesized according to the following procedure.

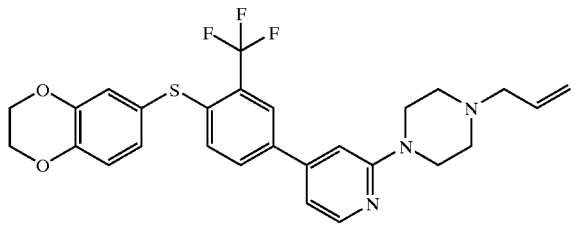

136

The title compound was prepared according to the procedures of Example 38E, substituting compound 76 with compound 118 (0.033 g, 0.0779 mmol) and 3-hydroxypyrrolidine with 1-allylpiperazine. A yellow solid 136 was obtained (0.037 g, 73%). $^1$H-NMR (CDCl$_3$, 400 MHz) δ 2.10–2.55 (br m, 6H), 3.24–3.45 (br m, 2H), 3.7 (d, J=7.0 Hz, 2H), 4.06–4.20 (br, 2H), 4.28–4.34 (m, 4H), 5.54 (d, J=7.2 Hz, 1H), 5.61 (d, J=10.2 Hz, 1H), 6.06 (m, 1H), 6.88 (s, 1H), 6.94 (d, J=8.4 Hz, 1H), 7.02–7.06 (m, 2H), 7.09 (d, J=1.9 Hz, 1H), 7.13 (d, J=8.1 Hz, 1H), 7.52 (d, J=8.1 Hz, 1H), 7.82 (s, 1H), 8.26 (d, J=5.9 Hz, 1H); MS (APCI) m/z 514 (M+H)$^+$.

EXAMPLE 95

2-(4-(4-(4-(2,3-Dihydro-benzo(1,4)dioxin-6-ylsulfanyl)-3-trifluoromethyl-phenyl)-pyridin-2-yl)-piperazin-1-yl)-ethanol 137 was synthesized according to the following procedure.

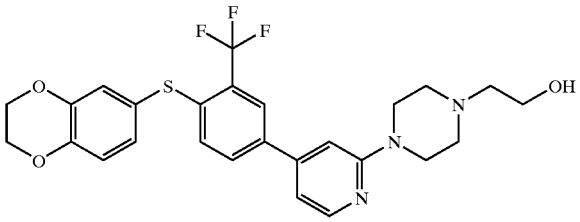

137

The title compound was prepared according to the procedures of Example 38E, substituting compound 76 with compound 118 (0.033 g, 0.0779 mmol) and 3-hydroxypyrrolidine with 1-(2'-hydroxyethyl)piperazine. A yellow solid 137 was obtained (0.034 g, 67%). $^1$H-NMR (CDCl$_3$, 400 MHz) δ 2.65–3.20 (br m, 4H), 3.24 (br m, 2H), 3.42–3.54 (m, 2H), 4.06 (br m, 2H), 4.05–4.18 (br m, 2H), 4.28–4.34 (m, 4H), 6.88 (s, 1H), 6.94 (d, J=8.4 Hz, 1H), 7.02–7.06 (m, 2H), 7.09 (d, J=2.2 Hz, 1H), 7.13 (d, J=8.0 Hz, 1H), 7.52 (d, J=7.7 Hz, 1H), 7.82 (s, 1H), 8.25 (d, J=5.9 Hz, 1H); MS (APCI) m/z 518 (M+H)$^+$.

EXAMPLE 96

(4'-(4-(2,3-Dihydro-benzo(1,4)dioxin-6-ylsulfanyl)-3-trifluoromethyl-phenyl)-3,4,5,6-tetrahydro-2H-(1,2')bipyridnyl-3-yl)-methanol 138 was synthesized according to the following procedure.

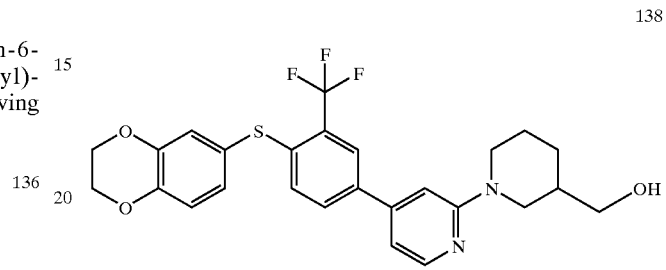

138

The title compound was prepared according to the procedures of Example 38E, substituting compound 76 with compound 118 (0.033 g, 0.0779 mmol) and 3-hydroxypyrrolidine with 3-hydryoxymethylpiperidine. A yellow solid 138 was obtained (0.030 g, 60%). $^1$H-NMR (CDCl$_3$, 400 MHz) δ 1.33–1.42 (m, 1H), 1.65–1.74 (m, 1H), 1.87–1.94 (m, 2H), 2.06–2.14 (m, 1H), 3.20–3.26 (m, 1H), 3.33–3.40 (m, 1H), 3.47–3.53 (m, 1H), 3.70–3.75 (m, 1H), 4.02–4.08 (m, 1H), 4.28–4.34 (m, 4H), 4.50–4.56 (m, 1H), 6.92 (d, J=6.6 Hz, 1H), 6.95 (d, J=8.4 Hz, 1H), 7.01 (s, 1H), 7.05 (dd, J=2.2 Hz, 8.4 Hz, 1H), 7.09 (d, J=1.8 Hz, 1H), 7.12 (d, J=8.4 Hz, 1H), 7.52 (d, J=8.3 Hz, 1H), 7.83 (s, 1H), 8.33 (d, J=6.6 Hz, 1H); MS (APCI) m/z 503 (M+H)$^+$.

EXAMPLE 97

Compounds that antagonize the interaction between ICAM-1 and LFA-1 can be identified, and their activities quantitated, using both biochemical and cell-based adhesion assays. A primary biochemical assay, described below as assay 97A, was utilized to measure the ability of the present compounds to block the interaction between the integrin LFA-1 and its adhesion partner ICAM-1.

97A. ICAM-1/LFA-1 Biochemical Interaction Assay

In the biochemical assay, 100 mL of anti-LFA-1 antibody (ICOS Corporation) at a concentration of 5 mg/ml in Dulbecco's phosphate-buffered saline (D-PBS) is used to coat wells of a 96-well microtiter plate overnight at 4° C. The wells are then washed twice with wash buffer (D-PBS w/o Ca$^{++}$ or Mg$^{++}$, 0.05% Tween 20) and blocked by addition of 200 mL of D-PBS, 5% fish skin gelatin. Recombinant LFA-1 (100 mL of 0.7 mg/ml, ICOS Corporation) in D-PBS is then added to each well. Incubation continues for 1 hour at room temperature and the wells are washed twice with wash buffer. Serial dilutions of compounds being assayed as ICAM-1/LFA-1 antagonists, prepared as 10 mM stock solutions in dimethyl sulfoxide (DMSO), are diluted in D-PBS, 2 mM MgCl$_2$, 1% fish skin gelatin and 50 mL of each dilution added to duplicate wells. This is followed by addition of 50 mL of 0.8 mg/ml biotinylated recombinant ICAM-1/Ig (ICOS Corporation) to the wells and the plates are incubated at room temperature for 1 hour. The wells are then washed twice with wash buffer and 100 mL of Europium-labeled Streptavidin (Wallac Oy) diluted 1:100 in Delfia assay buffer (Wallac Oy) are added to the wells. Incubation proceeds for 1 hour at room temperature. The wells are washed eight times with wash buffer and 100 μL of enhancement solution (Wallac Oy, cat. No. 1244–105) are added to each well. Incubation proceeds for 5 minutes with constant mixing. Time-resolved fluorimetry measurements are made using the Victor 1420 Multilabel Counter (Wallac Oy) and the percent inhibition of each candidate compound is calculated using the following equation:

$$\% \text{ inhibition} = 100 \times \left\{ 1 - \frac{\text{average OD w/compound minus background}}{\text{average OD w/o compound minus background}} \right\}$$

where "background" refers to wells that are not coated with anti-LFA-1 antibody.

The compounds inhibit the binding of ICAM-1 to LFA-1 with an $IC_{50}$ less than 20 micromolar.

Biologically relevant activity of the compounds in this invention was confirmed using a cell-based adhesion assay, (described below as assay 97B) which measured the ability of the present compounds to block the adherence of JY-8 cells (a human EBV-transformed B cell line expressing LFA-1 on its surface) to immobilized ICAM-1.

97B. ICAM-1/JY-8 cell adhesion assay

For measurement of inhibitory activity in the cell-based adhesion assay, 96-well microtiter plates are coated with 70 μL of recombinant ICAM-1/Ig (ICOS Corporation) at a concentration of 5 μg/mL in D-PBS w/o $Ca^{++}$ or $Mg^{++}$ overnight at 4° C. The wells are then washed twice with D-PBS and blocked by addition of 200 μL of D-PBS, 5% fish skin gelatin by incubation for 1 hour at room temperature. Fluorescent tagged JY-8 cells (a human EBV-transformed B cell line expressing LFA-1 on its surface; 50 μL at $2 \times 10^6$ cells/ml in RPMI 1640 (standard cell culture medium) /1% fetal bovine serum) are added to the wells. For fluorescent labeling of JY-8 cells, $5 \times 10^6$ cells washed once in RPMI 1640 are resuspended in 1 mL of RPMI 1640 containing 2 μM Calceiun AM (MolecularProbes), are incubated at 37° C. for 30 minutes and washed once with RPMI-1640/1% fetal bovine serun. Dilutions of compounds to be assayed for ICAM-1/LFA-1 antagonistic activity are prepared in RPMI-1640/ 1% fetal bovine serum from 10 mM stock solutions in DMSO and 50 μL are added to duplicate wells. Microtiter plates are incubated for 45 minutes at room temperature and the wells are washed gently once with RPMI-1640/ 1% fetal bovine serum. Fluorescent intensity is measured in a fluorescent plate reader with an excitation wavelength at 485 nM and an emission wavelength at 530 nM. The percent inhibition of a candidate compound at a given concentration is calculated using the following equation:

$$\% \text{ inhibition} = 100 \times \left\{ 1 - \frac{\text{average OD w/compound}}{\text{average OD w/o compound}} \right\}$$

and these concentration/inhibition data are used to generate dose response curves, from which $IC_{50}$ values are derived.

The ability of the compounds of this invention to treat arthritis can be demonstrated in a murine collagen-induced arthritis model according to the method of Kakimoto, et al., *Cell Immunol* 142: 326–337, 1992, in a rat collagen-induced arthritis model according to the method of Knoerzer, et al., *Toxicol Pathol* 25:13–19, 1997, in a rat adjuvant arthritis model according to the method of Halloran, et al., *Arthritis Rheum* 39: 810–819, 1996, in a rat streptococcal cell wall-induced arthritis model according to the method of Schimmer, et al., *J Immunol* 160: 1466–1477, 1998, or in a SCID-mouse human rheumatoid arthritis model according to the method of Oppenheimer-Marks et al., *J Clin Invest* 101: 1261–1272, 1998.

The ability of the compounds of this invention to treat Lyme arthritis can be demonstrated according to the method of Gross et al., *Science* 281, 703–706, 1998.

The ability of compounds of this invention to treat asthma can be demonstrated in a murine allergic asthma model according to the method of Wegner et al., *Science* 247:456–459, 1990, or in a murine non-allergic asthma model according to the method of Bloemen et al., *Am J Respir Crit Care Med* 153:521–529, 1996.

The ability of compounds of this invention to treat inflammatory lung injury can be demonstrated in a murine oxygen-induced lung injury model according to the method of Wegner et al., *Lung* 170:267–279, 1992, in a murine immune complex-induced lung injury model according to the method of Mulligan et al., *J Immunol* 154:1350–1363, 1995, or in a murine acid-induced lung injury model according to the method of Nagase, et al., *Am J Respir Crit Care Med* 154:504–510, 1996.

The ability of compounds of this invention to treat inflammatory bowel disease can be demonstrated in a rabbit chemical-induced colitis model according to the method of Bennet et al., *J Pharmacol Exp Ther* 280:988–1000, 1997.

The ability of compounds of this invention to treat autoimmune diabetes can be demonstrated in an NOD mouse model according to the method of Hasagawa et al., *Int Immunol* 6:831–838, 1994, or in a murine streptozotocin-induced diabetes model according to the method of Herrold et al., *Cell Immunol* 157:489–500, 1994.

The ability of compounds of this invention to treat inflammatory liver injury can be demonstrated in a murine liver injury model according to the method of Tanaka et al., *J Immunol* 151:5088–5095, 1993.

The ability of compounds of this invention to treat inflammatory glomerular injury can be demonstrated in a rat nephrotoxic serum nephritis model according to the method of Kawasaki, et al., *J Immunol* 150:1074–1083, 1993.

The ability of compounds of this invention to treat radiation-induced enteritis can be demonstrated in a rat abdominal irradiation model according to the method of Panes et al., *Gastroenterology* 108:1761–1769, 1995.

The ability of compounds of this invention to treat radiation pneumonitis can be demonstrated in a murine pulmonary irradiation model according to the method of Hallahan et al., *Proc Natl Acad Sci USA* 94:6432–6437, 1997.

The ability of compounds of this invention to treat reperfusion injury can be demonstrated in the isolated rat heart according to the method of Tamiya et al., *Immunopharmacology* 29(1): 53–63, 1995, or in the anesthetized dog according to the model of Hartman et al., *Cardiovasc Res* 30(1): 47–54, 1995.

The ability of compounds of this invention to treat pulmonary reperfusion injury can be demonstrated in a rat lung allograft reperfusion injury model according to the method of DeMeester et al., *Transplantation* 62(10): 1477–1485, 1996, or in a rabbit pulmonary edema model according to the method of Horgan et al., *Am J Physiol* 261(5): H1578–H1584, 1991.

The ability of compounds of this invention to treat stroke can be demonstrated in a rabbit cerebral embolism stroke model according the method of Bowes et al., *Exp Neurol* 119(2): 215–219, 1993, in a rat middle cerebral artery ischemia-reperfusion model according to the method of Chopp et al., *Stroke* 25(4): 869–875, 1994, or in a rabbit reversible spinal cord ischemia model according to the method of Clark et al., *Neurosurg* 75(4): 623–627, 1991.

The ability of compounds of this invention to treat peripheral artery occlusion can be demonstrated in a rat skeletal muscle ischemia/reperfusion model according to the method of Gute et al., *Mol Cell Biochem* 179: 169–187, 1998.

The ability of compounds of this invention to treat graft rejection can be demonstrated in a murine cardiac allograft rejection model according to the method of Isobe et al., *Science* 255: 1125–1127, 1992, in a murine thyroid gland kidney capsule model according to the method of Talento et al., *Transplantation* 55: 418–422, 1993, in a cynomolgus monkey renal allograft model according to the method of Cosimi et al., *J Immunol* 144: 4604–4612, 1990, in a rat nerve allograft model according to the method of Nakao et al., *Muscle Nerve* 18: 93–102, 1995, in a murine skin allograft model according to the method of Gorczynski and Wojcik, *J Immunol* 152: 2011–2019, 1994, in a murine corneal allograft model according to the method of He et al., *Opthalmol Vis Sci* 35: 3218–3225, 1994, or in a xenogeneic pancreatic islet cell transplantation model according to the method of Zeng et al., *Transplantation* 58:681–689, 1994.

The ability of compounds of this invention to treat graft-vs.-host disease (GVHD) can be demonstrated in a murine lethal GVHD model according to the method of Harning et al., *Transplantation* 52:842–845, 1991.

The ability of compounds of this invention to treat cancers can be demonstrated in a human lymphoma metastasis model (in mice) according to the method of Aoudjit et al., *J Immunol* 161:2333–2338, 1998.

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

What is claimed is:

1. A compound of formula I

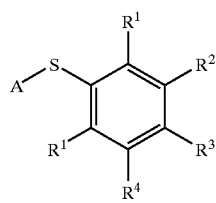

I or a pharmaceutically acceptable salt or prodrug thereof, wherein $R^1$, $R^2$, $R^3$, $R^4$ and $R^5$ are each independently selected from the group consisting of hydrogen, halogen, alkyl, haloalkyl, alkoxy, cyano, nitro, cycloalkyl, carboxaldehyde, a group of formula II defined as

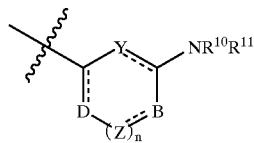

II and wherein at least one of $R^1$ or $R^3$ is a pyrimidine;

subject to the proviso that one or more than one of $R^1$ or $R^3$ is a group of formula II as defined above;

D, B, Y and Z are each independently selected from the group consisting of —$CR^6$=, —$CR^7R^8$—, —C(O)—, —O—, —$SO_2$—, —S—, —N=, and —$NR^9$—;

n is an integer of zero to three;

$R^6$, $R^7$, $R^8$ and $R^9$ are each independently selected from the group consisting of hydrogen, alkyl, carboxy, hydroxyalkyl, alkylaminocarbonylalkyl, dialkylaminocarbonylalkyl and carboxyalkyl; and $R^{10}$ and $R^{11}$ are each independently selected from the group consisting of hydrogen, alkyl, cycloalkyl, alkoxyalkyl, alkoxycarbonylalkyl, carboxyalkyl, hydroxyalkyl, heterocyclyl, heterocyclylalkyl and heterocyclylamino; or $R^{10}$ and $R^{11}$ are taken together with N to form a three to seven membered unsubstituted heterocyclyl, or a three to seven membered substituted heterocyclyl ring, substituted with one or more than one substituent $R^{13}$, wherein $R^{13}$ is independently selected from the group consisting of alkyl, alkylene, alkoxy, alkoxyalkyl, cycloalkyl, aryl, heterocyclyl, heterocyclylalkyl, heterocyclylcarbonyl, heterocyclylalkylaminocarbonyl, hydroxy, hydroxyalkyl, hydroxyalkoxyalkyl, carboxy, carboxyalkyl, carboxycarbonyl, carboxaldehyde, alkoxycarbonyl, arylalkoxycarbonyl, aminoalkyl, aminoalkanoyl, aminocarbonyl, carboxamido, alkoxycarbonylalkyl, carboxamidoalkyl, cyano, tetrazolyl, alkanoyl, hydroxyalkanoyl, alkanoyloxy, alkanoylamino, alkanoyloxyalkyl, alkanoylaminoalkyl, sulfonate, alkylsulfonyl, alkylsulfonylaminocarbonyl, arylsulfonylaminocarbonyl and heterocyclylsulfonylaminocarbonyl;

A is an unsubstituted aryl group, an unsubstituted heterocyclyl group, a substituted aryl group, or a substituted heterocyclyl group, substituted with one or more than one substituent $R^{12}$, wherein $R^{12}$, is independently selected from the group consisting of halogen, alkyl, aryl, haloalkyl, hydroxy, all oxy, alkoxyalkyl, alkoxycarbonyl, alkoxyalkoxy, hydroxyalkyl, aminoalkyl, aminocarbonyl, alkyl(alkoxycarbonylalkyl) aminoalkyl, heterocyclyl, heterocyclylalkyl, carboxaldehyde, carboxaldehyde hydrazone, carboxamido, alkoxycarbonylalkyl, carboxy, carboxyalkyl, carboxyalkoxy, hydroxyalkylaminocarbonyl, cyano, amino, heterocyclylalkylamino, carboxythioalkoxy, carboxycycloalkoxy, thioalkoxy, carboxyalkylamino, trans-cinnamyl and heterocyclylalkylaminocarbonyl; and wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are unsubstituted or substituted with one or more than one electron donating or electron withdrawing group wherein the heterocyclyl is chosen from 3-,4-,5-,6- and 7-membered rings containing 1–3 heteroatoms independently selected from nitrogen, oxygen and sulfur; the 4- and 5-membered rings have zero to two double bonds and the 6- and 7-membered rings have zero to three double bonds, the heterocyclyl being optionally substituted with alkyl, halogen, hydroxy or alkoxy substituents, further wherein the heterocyclyl optionally comprises a group chosen from:
(i) bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring, and another monocyclic heterocyclic ring;
(ii) bridged bicyclic groups where a monocyclic heterocyclic group is bridged by an alkylene group optionally selected from

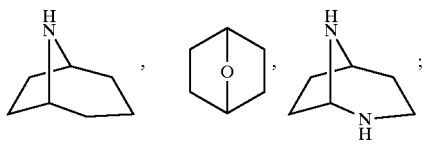

and
(iii) compounds of the formula

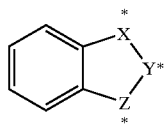

where X* and Z* are each independently selected from —CH$_2$—, —CH$_2$NH—, —CH$_2$O—, —NH— and —O—, with the proviso that at least one of X* and Z* is not —CH$_2$—, and Y* is selected from —C(O)— and —(C(R")$_2$)v -, where R" is hydrogen or alkyl of one to our carbons, and v is 1–3.

2. A compound according to claim 1 wherein R$^3$ is the group of formula II

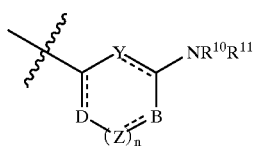

wherein R$^{10}$, R$^{11}$, D, B, Y, Z, and n are defined as in claim 1; and

R$^1$ is defined as in claim 1 with the proviso that if R$^3$ does not define a pyrimidine, then R$^1$ is a pyrimidine.

3. A compound according to claim 1 of formula III

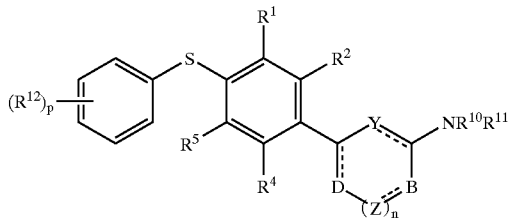

wherein R$^1$, R$^2$, R$^4$, R$^5$, R$^{10}$, R$^{11}$, R$^{12}$, D, B, Y, Z, and n are defined as in claim 1;

and p is an integer of zero to five.

4. A compound according to claim 3 wherein p is one;
R$^4$ and R$^5$ are hydrogen;
R$^{12}$ is selected from the group consisting of halogen, alkyl, alkoxy, carboxyalkoxy, carboxyalkyl and heterocyclyl;
R$^{10}$ and R$^{11}$ are taken together with N to form a three to seven membered unsubstituted heterocyclyl ring, or a three to seven membered substituted heterocyclyl ring, substituted with one or more than one substituent R$^{13}$, wherein R$^{13}$ is defined as in claim 1, and wherein said substituted heterocyclyl, or unsubstituted heterocyclyl ring is selected from the group consisting of piperidine, piperazine, morpholine, pyrrolidine, and azetidine; and
wherein R$^{10}$, R$^{11}$, R$^{12}$ and R$^{13}$ are unsubstituted or substituted with at least one electron donating or electron withdrawing group.

5. A compound according to claim 1 of formula IV

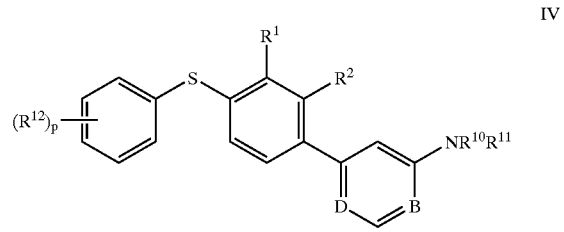

wherein D and B are each independently selected from the group consisting of —N= and —CR$^6$=;
R$^1$ is selected from the group consisting of hydrogen, halogen and haloalkyl, with the proviso that if R$^3$ does not define a pyrimidine, then R$^1$ is a pyrimidine;
R$^2$ is selected from the group consisting of hydrogen, halogen and haloalkyl;
R$^{10}$ and R$^{11}$ are defined as in claim 1;
R$^{12}$, at each occurrence, is independently selected from the group consisting of halogen, alky, haloalkyl, alkoxy, carboxyalkoxy, carboxyalkyl and heterocyclyl, wherein R$^{12}$ is unsubstituted or substituted with at least one electron donating group or electron withdrawing group; and
p is an integer of zero to five.

6. A compound and according to claim 5 wherein p is one; and
R$^{10}$ and R$^{11}$ are taken together with N to form a three to seven membered substituted heterocyclyl ring, or a three to seven membered unsubstituted heterocyclyl ring, substituted with one or more substituents R$^{13}$, wherein R$^{13}$ is defined as in claim 1, and wherein said substituted heterocyclyl ring, or unsubstituted heterocyclyl ring is selected from the group consisting of piperidine, piperazine, morpholine, pyrrolidine, and azetidine.

7. A compound according to claim 1, selected from the group consisting of 1-(6-(4-(2-isopropyl-phenylsulfanyl)-3-trifluoromethyl-phenyl)-pyrimidin-4-yl)-piperidine-3-carboxylic acid 4-(4-(2-isopropyl-phenylsulfanyl)-3-trifluoromethyl-phenyl)-6-(3-(2H-tetrazol-5-yl)-piperidin-1-yl)-pyrimidine, 4-(4-(2-isopropyl-phenylsulfanyl)-3-trifluoromethyl-phenyl)-6-(4-(2H-tetrazol-5-yl)-piperidin-1-yl)-pyrimidine, (1-(6-(4-(2-isopropyl-phenylsulfanyl)-3-trifluoromethyl-phenyl)-pyrimidin-4-yl)-piperidin-3-yl)-methanol, 2-(1-(6-(4-(2-isopropylphenylsulfanyl)-3-trifluoromethyl-phenyl)-pyrimidin-4-yl)-piperidin-4-yl)- ethanol, 4-(6-(4-(2-isopropyl-phenylsulfanyl)-3-trifluoromethyl-phenyl)-pyrimidin-4-yl)-morpholine, 1-(6-(4-(2-isopropyl-phenylsulfanyl)-3-trifluoromethyl-phenyl)-pyrimidin-4-yl)-piperidin-4-ol, 4-(6-(4-(2-isopropyl-phenylsulfanyl)-3-trifluoromethyl-phenyl)-pyrimidin-4-yl)-2,5-dimethyl-morpholine, 1-(6-(4-(2-isopropyl-phenylsulfanyl)-3-trifluoromethyl-phenyl)-pyrimidin-4-yl)-piperidine-3-carboxylic acid amide, 1-(6-(4-(2-isopropyl-phenylsulfanyl)-3-trifluoromethyl-phenyl)-pyrimidin-4-yl)-piperidine-4-carboxylic acid amide, N-Ethyl-N-1-(6-(4-(2-isopropyl-phenylsulfanyl)-3-trifluoromethyl-phenyl)-pyrimidin-4-yl)-pyrrolidin-3-yl)-acetamide, 1-(6-(4-(2-isopropyl-phenylsulfanyl)-3-trifluoromethyl-phenyl)-pyrimidin-4-yl)-piperidine-3-carboxylic acid ethyl ester, 1-(6-(4-(2-isopropyl-phenylsulfanyl)-3-trifluoromethyl-phenyl)-pyrimidin-4-yl)-piperidine-4-carboxylic acid ethyl ester, 4-(6-(4-(2-isopropyl-phenylsulfanyl)-3-trifluoromethyl-phenyl)-pyrimidin-4-yl)-piperazine-1-carboxylic acid ethyl ester, 4-(6-(4-(2-isopropyl-phenylsulfanyl)-3-trifluoromethyl-phenyl)-pyrimidin-4-yl)-piperazin-1-yl-acetic acid ethyl ester, (3-imidazol-1-yl-propyl)-(6-(4-(2-isopropyl-phenylsulfanyl)-3-trifluoromethyl-phenyl)-pyrimidin-4-yl)-amine, 1-(6-(4-(2-isopropyl-phenylsulfanyl)-3-trifluoromethyl-phenyl)-pyrimidin-4-yl)-piperidine-4-carboxylic acid, 4-(4-(2-isopropyl-phenylsulfanyl)-3-trifluoromethyl-phenyl)-pyrimidin-4-yl)-piperidine-3-carboxylic acid, 1-(6-(4-(2-isopropyl phenylsulfanyl)-3-trifluoromethyl-phenyl)-pyrimidin-4-yl)-piperidine-3-carboxylic acid diethyl amide, N-1-(6-(4-(2-isopropyl-phenylsulfanyl)-3-trifluoromethyl-phenyl)-pyrimidin-4-yl)-pyrrolidin-3-yl)-acetamide, 4-(4-(2-isopropyl-phenylsulfanyl)-3-trifluoromethyl-phenyl)-6-(2-methoxymethyl-pyrrolidin-1-yl)-pyrimidine, 1-(6-(4-(2-isopropyl-phenylsulfanyl) 3-trifluoromethyl-phenyl)-pyrimidin-4-yl)-pyrrolidin-3-ol, (1-(6-(4-(2-isopropyl-phenylsulfanyl)-3-trifluoromethyl-phenyl)-pyrimidin-4-yl)-pyrrolidin-3-yl)-carbamic acid tert-butyl ester, isopropyl-(6-(4-(2-isopropyl-phenylsulfanyl)-3-trifluoromethyl-phenyl)-pyrimidin-4-yl)-methyl amine, and ethyl-(6-(4-(2-isopropyl-phenylsulfanyl)-3-trifluoromethyl-phenyl)-pyrimidin-4-yl)-methyl-amine.

8. A composition comprising:
a compound according to claim 1
and a pharmaceutically-acceptable carrier.

9. A method of inhibiting inflammation or suppressing immune response in a mammal comprising administering to said mammal a therapeutic amount of a compound according to calm 1.

10. A compound according to claim 1 wherein A is
(i) an unsubstituted or substituted aryl group, substituted by one or more than one substituent $R^{12}$, wherein $R^{12}$ is defined as in claim 1, or
(ii) an unsubstituted or substituted heterocyclyl group of the formula

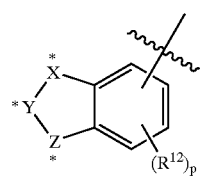

wherein
$R^{12}$ and is defined as in claim 1;
p is an integer of 0 to 5;

X* and Z* are each independently selected from the group consisting of —CH$_2$—, —CH$_2$NH, —CH$_2$O—, —NH—, and —O—, with the proviso that at least one of X* md Z* is not —CH$_2$—; and
Y* is —(C(R")$_2$)$_v$-wherein
R" is hydrogen alkyl; and
V is 1, 2, or 3.

11. A compound according to claim 1 or 10 wherein A is an unsubstituted or substituted aryl group, wherein the aryl group is
(i) a mono- or a bicyclic carbocyclic ring system having one or two aromatic rings, or
(ii) a mono- or a bicyclic carbocyclic ring system having one or two aromatic rings,
wherein one or more then one of the aromatic rings is fused to a ring selected from the group consisting of cyclohexane, cyclohexene, cyclopentane, and cyclopentene.

12. A compound according to claim 1 wherein A is an unsubstituted or substituted aryl group of the formula

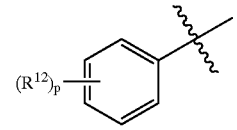

wherein $R^{12}$ is defined as in claim 1; and p is an integer of 0 to 5.

13. A compound according to claim 1 wherein
D is CR$_6$= or —N=,
B is —S—, —O—, —CR$^6$= or —N=,
Y is —CR$^6$= or —N=,
Z is —CR$^6$= or —N—; and
n is zero or one.

14. A compound according to claim 1 wherein $R^3$ is selected from the group consisting of

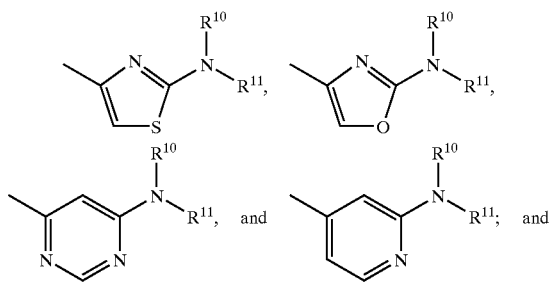

$R^1$ is defined as in claim 1 with the proviso that if $R^3$ does not define a pyrimidine, then $R^1$ is a pyrimidine.

15. A compound according to claim 1 wherein,
D is —CR$^6$=;
B is —O—or —S—;
Y is —N=; and
n is zero.

16. A compound according to claim 1 wherein
D is —CR$^6$= or —N=;
B is —N=;
Y is CR$^6$=; and
n is 1.

17. A compound according to claim 1 wherein $R^1$ is selected from the group consisting of hydrogen, halogen, alkyl, nitro, and

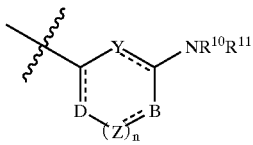

wherein $R^{10}$, $R^{11}$, D, B, Y, Z, and n are defined as in claim 1, with the proviso that if $R^3$ does not define a pyrimidine, then $R^1$ is a pyrimidine;

$R^2$ is selected from the group consisting of hydrogen, halogen, alkyl, and nitro;

$R^4$ and $R^5$ are each independently selected from the group consisting of hydrogen and alkyl; and $R^3$ is

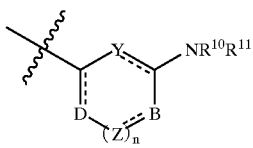

wherein

D is —$CR^6$= or —N=,

B is —S—, —O—, —$CR^6$= or —N=,

Y is —$CR^6$= or —N=,

Z is —$CR^6$= or —N=; and n is zero or one.

18. A compound according to claim 1 wherein $R^1$ and $R^2$ are each independently selected from the group consisting of hydrogen, hydrogen, and haloalkyl;

$R^3$ is a pyrimidine; and $R^4$ and $R^5$ are each independently hydrogen.

19. A compound according to claim 1 wherein $R^1$ is selected from the group consisting of hydrogen, halogen, haloalkyl, and

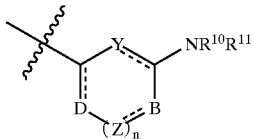

wherein $R^{10}$, $R^{11}$, D, B, Y, Z, and n are defined as in claim 1, with the proviso that if $R^3$ does not define a pyrimidine, then $R^1$ is a pyrimidine;

$R^2$ is selected from the group consisting of hydrogen, halogen, and haloalkyl;

$R^4$ and $R^5$ are each independently hydrogen; and $R^3$ is

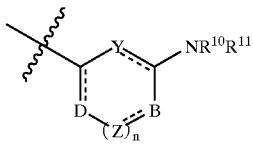

wherein

D is —$CR^6$= or —N=,

B is —S—, —O—, —$CR^6$= or —N=,

Y is —$CR^6$= or —N=,

Z is —$CR^6$= or —N=; and n is zero one.

20. A compound according to claim 1 wherein $R^1$ is selected from the group consisting of hydrogen, halogen, haloalkyl, and

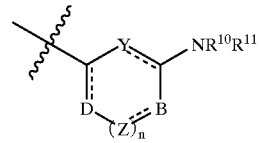

wherein $R^{10}$, $R^{11}$, D, B, Y, Z, and n are d fin d as in claim 1, with the proviso that if $R^3$ does not define a pyrimdine, then $R^1$ is a pyrimdine;

$R^2$ is selected from the group consisting of hydrogen, chloro, and trifluoromethyl;

$R^4$ and $R^5$ are each independently hydrogen; and $R^3$ is selected from the group consisting of

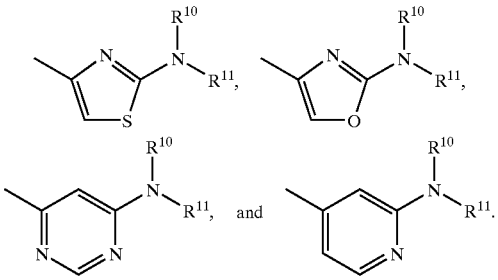

21. A compound according to claim 1 wherein $R^6$ is hydrogen.

22. A compound according to claim 1 wherein $R^1$ is selected from the group consisting of hydrogen, halogen and haloalkyl, $R^2$ is selected from the group consisting of hydrogen and halogen, $R^3$ is a pyrimidine, and $R^4$ and $R^5$ are each hydrogen.

23. A compound according to claim 22 wherein $R^1$ is trifluoromethyl, $R^2$ is hydrogen, and $R^3$ is a pyrimidine.

24. A compound according to claim 22 wherein $R^1$ and $R^2$ are each chloro, and $R^3$ is a pyrimidine.

25. A compound according to claim 1 which has an $IC_{50}$ of less than 20 μM when tested in one or both of (i) an ICAM-1/LFA-1 Biochemical Interaction Assay, or (ii) an ICAM-1/JY-8 Cell Adhesion Assay.

26. A method for ameliorating a pathology in a mammal arising from the interaction of LFA-1 with ICAM-1 or ICAM-3 comprising administering to said mammal a therapeutic amount of a compound according to claim 1.

27. A method according to claim 26 wherein the pathology is selected from an inflammatory disease, an autoimmune disease, tumor metastasis, allograft rejection and reperfusion injury.

* * * * *

UNITED STATES PATENT AND TRADEMARK OFFICE
CERTIFICATE OF CORRECTION

PATENT NO. : 6,787,542 B2
DATED : September 7, 2004
INVENTOR(S) : Gary T. Wang, Sheldon Wang and Robert Gentles It is certified that error appears in the above-identified patent and that said Letters Patent is hereby corrected as shown below:

Column 74,
Line 50, "all oxy" should read -- alkoxy --.

Column 75,
Line 39, "our" should read -- four --.

Column 77,
Line 34, insert -- - -- before "3-trifluoromethyl-phenyl) --.

Column 78,
Line 4, "md" should read -- and --.
Line 6, insert -- or -- before "alkyl".
Line 7, "V" should read -- v --.
Line 16, "then" should read -- than --.

Column 80,
Line 18, "d fn d" should read -- defined --.

Signed and Sealed this

Twenty-eighth Day of December, 2004

JON W. DUDAS
*Director of the United States Patent and Trademark Office*